(12) United States Patent
Carson et al.

(10) Patent No.: US 9,050,376 B2
(45) Date of Patent: *Jun. 9, 2015

(54) CONJUGATES OF SYNTHETIC TLR AGONISTS AND USES THEREFOR

(71) Applicant: The Regents of The University of California, Oakland, CA (US)

(72) Inventors: Dennis A. Carson, La Jolla, CA (US); Howard B. Cottam, Escondido, CA (US); Wolfgang Wrasidlo, La Jolla, CA (US); Christina C. N. Wu, Escondido, CA (US); Gregory A. Daniels, San Diego, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/309,245

(22) Filed: Jun. 19, 2014

(65) Prior Publication Data

US 2014/0302120 A1    Oct. 9, 2014

Related U.S. Application Data

(60) Continuation of application No. 13/736,545, filed on Jan. 8, 2013, now Pat. No. 8,790,655, which is a division of application No. 12/027,960, filed on Feb. 7, 2008, now Pat. No. 8,357,374.

(60) Provisional application No. 60/888,699, filed on Feb. 7, 2007.

(51) Int. Cl.
| | | |
|---|---|---|
| *A61K 39/385* | (2006.01) | |
| *A61K 45/00* | (2006.01) | |
| *A61K 47/00* | (2006.01) | |
| *A61K 9/127* | (2006.01) | |
| *A01N 43/90* | (2006.01) | |
| *A61K 31/522* | (2006.01) | |

(Continued)

(52) U.S. Cl.
CPC ........... *A61K 47/48815* (2013.01); *A61K 31/52* (2013.01); *A61K 39/085* (2013.01); *A61K 39/39* (2013.01); *A61K 2039/55511* (2013.01); *C07D 487/04* (2013.01); *A61K 39/07* (2013.01); *C07F 9/65616* (2013.01); *A61K 2039/55555* (2013.01)

(58) Field of Classification Search
None
See application file for complete search history.

(56) References Cited

U.S. PATENT DOCUMENTS

| | | |
|---|---|---|
| 4,689,338 A | 8/1987 | Gerster |
| 4,929,624 A | 5/1990 | Gerster et al. |

(Continued)

FOREIGN PATENT DOCUMENTS

| | | |
|---|---|---|
| AU | 2007257423 | 5/2012 |
| AU | 2008227128 B2 | 3/2013 |

(Continued)

OTHER PUBLICATIONS

"U.S. Appl. No. 12/027,960, Amendment Under 37 C.F.R. Sec. 1.312 filed Nov. 1, 2012", 7 pgs.

(Continued)

*Primary Examiner* — Bong-Sook Baek
(74) *Attorney, Agent, or Firm* — Schwegman Lundberg & Woessner, P.A.

(57) ABSTRACT

The invention provides TLR agonists and conjugates thereof useful in vaccines and to prevent, inhibit or treat a variety of disorders including pathogen infection and asthma.

11 Claims, 34 Drawing Sheets

(51) Int. Cl.

| | |
|---|---|
| *C07D 473/00* | (2006.01) |
| *A61K 47/48* | (2006.01) |
| *A61K 31/52* | (2006.01) |
| *A61K 39/085* | (2006.01) |
| *A61K 39/39* | (2006.01) |
| *C07D 487/04* | (2006.01) |
| *A61K 39/07* | (2006.01) |
| *C07F 9/6561* | (2006.01) |
| *A61K 39/00* | (2006.01) |

(56) References Cited

U.S. PATENT DOCUMENTS

| | | |
|---|---|---|
| 4,938,949 A | 7/1990 | Borch et al. |
| 5,037,986 A | 8/1991 | Gerster |
| 5,175,296 A | 12/1992 | Gerster |
| 5,238,944 A | 8/1993 | Wick et al. |
| 5,352,784 A | 10/1994 | Nikolaides et al. |
| 5,367,076 A | 11/1994 | Gerster |
| 5,395,937 A | 3/1995 | Nikolaides et al. |
| 5,444,065 A | 8/1995 | Nikolaides et al. |
| 5,624,677 A | 4/1997 | El-Rashidy et al. |
| 5,627,281 A | 5/1997 | Nikolaides et al. |
| 5,648,516 A | 7/1997 | Nikolaides et al. |
| 5,693,811 A | 12/1997 | Lindstrom |
| 5,736,553 A | 4/1998 | Wick et al. |
| 5,741,908 A | 4/1998 | Gerster et al. |
| 5,998,619 A | 12/1999 | Gerster et al. |
| 6,038,505 A | 3/2000 | Probst et al. |
| 6,039,969 A | 3/2000 | Tomai et al. |
| 6,083,505 A | 7/2000 | Miller et al. |
| 6,150,523 A | 11/2000 | Gerster et al. |
| 6,200,592 B1 | 3/2001 | Tomai et al. |
| 6,245,776 B1 | 6/2001 | Skwierczynski et al. |
| 6,329,381 B1 | 12/2001 | Kurimoto et al. |
| 6,333,331 B1 | 12/2001 | Moschel et al. |
| 6,372,725 B1 | 4/2002 | Zilch et al. |
| 6,437,131 B1 | 8/2002 | Gerster et al. |
| 6,486,168 B1 | 11/2002 | Skwierczynski et al. |
| 6,534,654 B2 | 3/2003 | Gerster et al. |
| 6,552,192 B1 | 4/2003 | Hanus et al. |
| 6,610,319 B2 | 8/2003 | Tomai et al. |
| 6,613,902 B2 | 9/2003 | Gerster et al. |
| 6,624,305 B2 | 9/2003 | Gerster |
| 6,696,076 B2 | 2/2004 | Tomai et al. |
| 6,706,728 B2 | 3/2004 | Hedenstrom et al. |
| 6,716,840 B2 | 4/2004 | Chu et al. |
| 6,733,764 B2 | 5/2004 | Martin |
| 6,734,187 B1 | 5/2004 | Tanaka et al. |
| 6,897,314 B2 | 5/2005 | Gerster et al. |
| 6,960,582 B2 | 11/2005 | Boyce et al. |
| 7,001,609 B1 | 2/2006 | Matson et al. |
| 7,157,465 B2 | 1/2007 | Isobe et al. |
| 7,189,727 B2 | 3/2007 | Boyce |
| 7,238,700 B2 | 7/2007 | Palle et al. |
| 7,241,890 B2 | 7/2007 | Kasibhatla et al. |
| 7,521,454 B2 | 4/2009 | Isobe et al. |
| 7,576,068 B2 | 8/2009 | Averett |
| 7,754,728 B2 | 7/2010 | Isobe et al. |
| 7,968,544 B2 | 6/2011 | Graupe et al. |
| 8,211,863 B2 | 7/2012 | Averett |
| 8,357,374 B2 | 1/2013 | Carson et al. |
| 8,729,088 B2 | 5/2014 | Carson et al. |
| 8,790,655 B2 | 7/2014 | Carson |
| 8,846,697 B2 | 9/2014 | Carson et al. |
| 2002/0127224 A1 | 9/2002 | Chen |
| 2002/0193595 A1 | 12/2002 | Chu et al. |
| 2003/0187261 A1 | 10/2003 | Havlicek et al. |
| 2003/0191086 A1 | 10/2003 | Hanus et al. |
| 2004/0023211 A1 | 2/2004 | Groen et al. |
| 2004/0091491 A1 | 5/2004 | Kedl et al. |
| 2004/0132748 A1 | 7/2004 | Isobe et al. |
| 2004/0202663 A1 | 10/2004 | Hu et al. |
| 2004/0209899 A1 | 10/2004 | Palle et al. |
| 2004/0248895 A1 | 12/2004 | Chu et al. |
| 2004/0265351 A1 | 12/2004 | Miller et al. |
| 2005/0004144 A1 | 1/2005 | Carson et al. |
| 2005/0038027 A1 | 2/2005 | Boyce |
| 2005/0049263 A1 | 3/2005 | Kasibhatla et al. |
| 2005/0054590 A1 | 3/2005 | Averett |
| 2005/0059613 A1 | 3/2005 | Memarzadeh et al. |
| 2005/0266067 A1 | 12/2005 | Sengupta et al. |
| 2006/0052403 A1 | 3/2006 | Isobe et al. |
| 2006/0110746 A1 | 5/2006 | Andre et al. |
| 2007/0037832 A1 | 2/2007 | Isobe et al. |
| 2007/0087009 A1 | 4/2007 | Burdin |
| 2007/0100146 A1 | 5/2007 | Dzwiniel |
| 2007/0161582 A1 | 7/2007 | Mijikovic et al. |
| 2007/0173483 A1 | 7/2007 | Kasibhatla et al. |
| 2007/0190071 A1 | 8/2007 | Kurimoto et al. |
| 2007/0292418 A1 | 12/2007 | Fields et al. |
| 2008/0008682 A1 | 1/2008 | Chong et al. |
| 2008/0125446 A1 | 5/2008 | Kasibhatla et al. |
| 2008/0214580 A1 | 9/2008 | Neagu et al. |
| 2009/0047249 A1 | 2/2009 | Graupe et al. |
| 2009/0053186 A1 | 2/2009 | Hu et al. |
| 2009/0069289 A1 | 3/2009 | Neagu et al. |
| 2009/0099212 A1 | 4/2009 | Zablocki et al. |
| 2009/0105212 A1 | 4/2009 | Isobe et al. |
| 2009/0118263 A1 | 5/2009 | Hashimoto et al. |
| 2009/0202484 A1 | 8/2009 | Chong et al. |
| 2009/0202626 A1 | 8/2009 | Carson et al. |
| 2009/0324551 A1 | 12/2009 | Carson et al. |
| 2010/0210598 A1 | 8/2010 | Carson et al. |
| 2011/0098248 A1 | 4/2011 | Halcomb et al. |
| 2011/0098294 A1 | 4/2011 | Carson et al. |
| 2011/0319442 A1 | 12/2011 | Leoni et al. |
| 2012/0003298 A1 | 1/2012 | Barberis et al. |
| 2012/0009247 A1 | 1/2012 | Maj et al. |
| 2012/0083473 A1 | 4/2012 | Holldack et al. |
| 2012/0148660 A1 | 6/2012 | Carson et al. |
| 2012/0177681 A1 | 7/2012 | Singh et al. |
| 2013/0156807 A1 | 6/2013 | Carson et al. |
| 2013/0165455 A1 | 6/2013 | Carson et al. |
| 2013/0190494 A1 | 7/2013 | Carson et al. |

FOREIGN PATENT DOCUMENTS

| | | |
|---|---|---|
| AU | 2009210655 B2 | 8/2013 |
| CN | 101304748 A | 11/2008 |
| EP | 0145340 A2 | 6/1985 |
| EP | 0310950 A1 | 4/1989 |
| EP | 0389302 A1 | 9/1990 |
| EP | 0394026 A1 | 10/1990 |
| EP | 0553202 A1 | 8/1993 |
| EP | 0575549 A1 | 12/1993 |
| EP | 0636031 A1 | 2/1995 |
| EP | 0681570 A1 | 11/1995 |
| EP | 0708773 A1 | 5/1996 |
| EP | 0912564 A1 | 5/1999 |
| EP | 0912565 A1 | 5/1999 |
| EP | 0938315 A1 | 9/1999 |
| EP | 1035123 A1 | 9/2000 |
| EP | 1035123 B1 | 8/2003 |
| EP | 1386923 A1 | 2/2004 |
| EP | 1550662 A1 | 7/2005 |
| EP | 1939202 A1 | 7/2008 |
| EP | 2396328 | 12/2011 |
| HK | 1170226 A | 2/2013 |
| HK | 1138767 B | 5/2014 |
| JP | 11193282 A | 7/1999 |
| JP | 2004137157 A | 5/2004 |
| JP | 2005046160 A | 2/2005 |
| JP | 2005505504 A | 2/2005 |
| JP | 200589334 A | 4/2005 |
| JP | 2005089334 A | 4/2005 |
| JP | 2006519784 A | 8/2006 |
| JP | 2007504232 A | 3/2007 |
| JP | 2009504803 A | 2/2009 |
| JP | 2009510096 A | 3/2009 |
| JP | 2012517428 A | 8/2012 |
| JP | 2013525431 A | 6/2013 |
| JP | 2014129425 A | 7/2014 |
| WO | WO-9215581 A1 | 9/1992 |

(56) References Cited

FOREIGN PATENT DOCUMENTS

| WO | WO-9320847 A1 | 10/1993 |
|---|---|---|
| WO | WO-9817279 A1 | 4/1998 |
| WO | WO-9848805 A1 | 11/1998 |
| WO | WO-9928321 A1 | 6/1999 |
| WO | WO-0043394 A1 | 7/2000 |
| WO | WO-0144259 A1 | 6/2001 |
| WO | WO-0144260 A2 | 6/2001 |
| WO | WO-0149688 A1 | 7/2001 |
| WO | WO-0224225 A1 | 3/2002 |
| WO | WO-0230399 A2 | 4/2002 |
| WO | WO-03077944 A1 | 9/2003 |
| WO | WO-2004029054 A1 | 4/2004 |
| WO | WO-2004066947 A2 | 8/2004 |
| WO | WO-2005025583 A2 | 3/2005 |
| WO | WO-2005060966 A1 | 7/2005 |
| WO | WO-2005092892 A1 | 10/2005 |
| WO | WO-2006062945 A2 | 6/2006 |
| WO | WO-2006100226 A1 | 9/2006 |
| WO | WO-2007024707 A2 | 3/2007 |
| WO | WO-2007024707 A3 | 3/2007 |
| WO | WO-2007034817 A1 | 3/2007 |
| WO | WO-2007034917 A1 | 3/2007 |
| WO | WO-2007038720 A2 | 4/2007 |
| WO | WO-2007142755 A2 | 12/2007 |
| WO | WO-2007142755 A3 | 12/2007 |
| WO | WO-2008115319 A2 | 9/2008 |
| WO | WO-2008115319 A3 | 9/2008 |
| WO | WO-2009005687 A1 | 1/2009 |
| WO | WO-2009099650 A2 | 8/2009 |
| WO | WO-2009099650 A3 | 8/2009 |
| WO | WO-2009099650 A4 | 8/2009 |
| WO | WO-2010093436 A2 | 8/2010 |
| WO | WO-2011139348 A2 | 11/2011 |

OTHER PUBLICATIONS

"U.S. Appl. No. 12/027,960, Non Final Office Action mailed Apr. 10, 2012", 16 pgs.
"U.S. Appl. No. 12/027,960, Notice of Allowance mailed Aug. 1, 2012", 10 pgs.
"U.S. Appl. No. 12/027,960, Preliminary Amendment mailed Dec. 8, 2010", 21 pgs.
"U.S. Appl. No. 12/027,960, PTO Response to 312 Amendment mailed Nov. 14, 2012", 2 pgs.
"U.S. Appl. No. 12/027,960, Response filed Jul. 10, 2012 to Non Final Office Action mailed Apr. 10, 2012", 8 pgs.
"U.S. Appl. No. 12/027,960, Response filed Oct. 24, 2011 to Restriction Requirement mailed Sep. 23, 2011", 21 pgs.
"U.S. Appl. No. 12/027,960, Restriction Requirement mailed Sep. 23, 2011", 9 pgs.
"U.S. Appl. No. 12/064,529, Non Final Office Action mailed Apr. 9, 2012", 15 pgs.
"U.S. Appl. No. 12/064,529, Preliminary Amendment filed Feb. 22, 2008", 11 pgs.
"U.S. Appl. No. 12/064,529, Response filed Jul. 9, 2012 to Non Final Office Action mailed Apr. 9, 2012", 11 pgs.
"U.S. Appl. No. 12/064,529, Response filed Oct. 24, 2011 to Restriction Requirement mailed Aug. 24, 2011", 9 pgs.
"U.S. Appl. No. 12/064,529, Restriction Requirement mailed Aug. 24, 2011", 9 pgs.
"U.S. Appl. No. 12/302,738, Final Office Action mailed Oct. 3, 2013", 11 pgs.
"U.S. Appl. No. 12/302,738, Notice of Allowance mailed Apr. 22, 2014", 7 pgs.
"U.S. Appl. No. 12/302,738, Notice of Allowance mailed Dec. 27, 2013", 9 pgs.
"U.S. Appl. No. 12/302,738, Preliminary Amendment mailed Nov. 26, 2008", 8 pgs.
"U.S. Appl. No. 12/302,738, Response filed Jun. 26, 2013 to Non Final Office Action mailed Jan. 2, 2013", 10 pgs.
"U.S. Appl. No. 12/302,738, Response filed Dec. 3, 2013 to Final Office Action mailed Oct. 3, 2013", 8 pgs.
"U.S. Appl. No. 12/367,172, Final Office Action mailed Jan. 18, 2012", 15 pgs.
"U.S. Appl. No. 12/367,172, Final Office Action mailed Apr. 13, 2012", 21 pgs.
"U.S. Appl. No. 12/367,172, Non Final Office Action mailed May 27, 2011", 20 pgs.
"U.S. Appl. No. 12/367,172, Response filed Mar. 8, 2011 to Restriction Requirement mailed Dec. 8, 2010", 11 pgs.
"U.S. Appl. No. 12/367,172, Response filed Nov. 16, 2011 to Non Final Office Action mailed May 27, 2011", 6 pgs.
"U.S. Appl. No. 12/367,172, Restriction Requirement mailed Dec. 8, 2010", 6 pgs.
"U.S. Appl. No. 12/704,343, Advisory Action mailed Apr. 5, 2013", 3 pgs.
"U.S. Appl. No. 12/704,343, Final Office Action mailed May 10, 2013", 7 pgs.
"U.S. Appl. No. 12/704,343, Non Final Office Action mailed Jul. 16, 2012", 14 pgs.
"U.S. Appl. No. 12/704,343, Notice of Allowance mailed Jan. 3, 2014", 11 pgs.
"U.S. Appl. No. 12/704,343, Notice of Allowance mailed Aug. 2, 2013", 10 pgs.
"U.S. Appl. No. 12/704,343, Response filed Jun. 5, 2012 to Restriction Requirement mailed May 7, 2012", 7 pgs.
"U.S. Appl. No. 12/704,343, Response filed Jul. 10, 2013 to Final Office Action mailed May 10, 2013", 8 pgs.
"U.S. Appl. No. 12/704,343, Restriction Requirement mailed May 7, 2012", 7 pgs.
"U.S. Appl. No. 13/682,208, Final Office Action mailed May 23, 2014", 17 pgs.
"U.S. Appl. No. 13/682,208, Non Final Office Action mailed Nov. 7, 2013", 13 pgs.
"U.S. Appl. No. 13/682,208, Preliminary Amendment filed Nov. 20, 2012", 7 pgs.
"U.S. Appl. No. 13/682,208, Response filed Feb. 7, 2014 to Non Final Office Action mailed Nov. 7, 2013", 9 pgs.
"U.S. Appl. No. 13/682,208, Response filed Aug. 7, 2013 to Restriction Requirement mailed Jun. 6, 2013", 8 pgs.
"U.S. Appl. No. 13/682,208, Restriction Requirement mailed Jun. 6, 2013", 9 pgs.
"U.S. Appl. No. 13/736,545, Notice of Allowance mailed Mar. 18, 2014", 6 pgs.
"U.S. Appl. No. 13/736,545, Notice of Allowance mailed Aug. 2, 2013", 9 pgs.
"U.S. Appl. No. 13/736,545, Preliminary Amendment filed Mar. 6, 2013", 3 pgs.
"U.S. Appl. No. 13/791,175, Final Office Action mailed Dec. 26, 2013", 12 pgs.
"U.S. Appl. No. 13/791,175, Non Final Office Action mailed Jun. 7, 2013", 10 pgs.
"U.S. Appl. No. 13/791,175, Preliminary Amendment filed Mar. 8, 2013", 4 pgs.
"U.S. Appl. No. 13/791,175, Response filed Nov. 1, 2013 to Non Final Office Action mailed Jun. 7, 2013", 8 pgs.
"Australia Application Serial No. 2008227128, First Examiner Report mailed Jul. 6, 2012", 2 pgs.
"Australian Application Serial No. 2006283524, Office Action mailed Mar. 27, 2008", 1 pg.
"Australian Application Serial No. 2006283524, Office Action mailed Aug. 3, 2011", 4 pgs.
"Australian Application Serial No. 2006283524, Preliminary Amendment mailed Mar. 3, 2008", 18 pgs.
"Australian Application Serial No. 2006283524, Response filed May 19, 2008 to Office Action mailed Mar. 27, 2008", 10 pgs.
"Australian Application Serial No. 2007257423, Examiner Report mailed Jun. 6, 2011", 2 pgs.
"Australian Application Serial No. 2007257423, First Examiner Report mailed Sep. 22, 2010", 4 Pgs.
"Australian Application Serial No. 2007257423, Office Action mailed Oct. 20, 2011", 2 pgs.
"Australian Application Serial No. 2007257423, Response filed May 31, 2011 to First Examiner Report mailed Sep. 22, 2010", 16 pgs.

(56) References Cited

OTHER PUBLICATIONS

"Australian Application Serial No. 2007257423, Response filed Sep. 13, 2011 to Examination Report mailed Jun. 6, 2011", 12 pgs.
"Australian Application Serial No. 2007257423, Response filed Dec. 19, 2011 to Office Action mailed Oct. 20, 2011", 5 pgs.
"Australian Application Serial No. 2008227128, Preliminary Amendment filed Sep. 7, 2009", 45 pgs.
"Australian Application Serial No. 2009210655, Office Action mailed Apr. 19, 2013", 3 pgs.
"Australian Application Serial No. 2009210655, Response filed Jul. 18, 2013 to First Examiner Report mailed Apr. 19, 2013", 19 pgs.
"Canadian Application Serial No. 2,653,941, Office Action May 10, 2011", 3 pgs.
"Canadian Application Serial No. 2,653,941, Office Action mailed Feb. 8, 2012", 2 pgs.
"Canadian Application Serial No. 2,653,941, Office Action mailed Aug. 23, 2010", 5 pgs.
"Canadian Application Serial No. 2,653,941, Response filed Feb. 23, 2011 to Office Action mailed Aug. 23, 2010", 20 pgs.
"Canadian Application Serial No. 2,653,941, Response filed Nov. 9, 2011 to Office Action mailed May 10, 2011", 15 pgs.
"Canadian Application Serial No. 2,677,733, Voluntary Amendment filed Aug. 7, 2009", 45 pgs.
"Chinese Application Serial No. 200680038761.X, Office Action mailed Mar. 22, 2012", (w/ English Translation), 9 pgs.
"Chinese Application Serial No. 200680038761.X, Office Action mailed Apr. 14, 2010", with English translation, 9 pgs.
"Chinese Application Serial No. 200680038761.X, Office Action mailed Jun. 23, 2011", (w/ English Translation), 9 pgs.
"Chinese Application Serial No. 200680038761.X, Response filed Sep. 7, 2011 to Office Action mailed Jun. 23, 2011", (w/ English Translation of Amended Claims), 19 pgs.
"Chinese Application Serial No. 200680038761.X, Response filed Oct. 29, 2010 to Office Action mailed Apr. 14, 2010", (w/ English Translation of Amended Claims), 22 pgs.
"Chinese Application Serial No. 200680038761.X, Response filed Jul. 6, 2012 to Action mailed Mar. 22, 2012", (w/ English Translation), 9 pgs.
"Chinese Application Serial No. 200880011525.8, Office Action mailed Jan. 30, 2012", English Translation Only, 6 pgs.
"Chinese Application Serial No. 200880011525.8, Office Action mailed Jul. 5, 2012", (w/ English Translation), 14 pgs.
"Chinese Application Serial No. 200880011525.8, Response filed Jun. 13, 2012 to Office Action mailed Jan. 30, 2012", (w/ English Translation of Claims), 14 pgs.
"Chinese Application Serial No. 200880011525.8, Voluntary Amendment filed Dec. 2, 2010", (w/ English Translation of Claims), 12 pgs.
"Chinese Application Serial No. 200980112411.7, Rejection Decision mailed Jul. 23, 2013", (w/ English Translation), 14 pgs.
"Chinese Application Serial No. 200980112411.7, Response filed Mar. 19, 2013 to Office Action mailed Nov. 5, 2012", (w/ English Translation), 4 pgs.
"Chinese Application Serial No. 200980112411.7, Voluntary Amendment filed Jan. 31, 2011", (w/ English Translation of Claims), 74 pgs.
"Chinese Application Serial No. 200980112411.7, Office Action Mailed Feb. 2, 2012", w/ English Translation, 9 pgs.
"Eurasian Application Serial No. 200901078, Office Action mailed Jan. 29, 2013", (w/ English Translation), 4 pgs.
"Eurasian Application Serial No. 200901078, Office Action mailed Apr. 2, 2012", w/English Translation, 3 pgs.
"Eurasian Application Serial No. 200901078, Office Action mailed May 26, 2011", (w/ English Translation), 5 pgs.
"Eurasian Application Serial No. 200901078, Office Action mailed Sep. 18, 2012", (w/ English Translation), 4 pgs.
"Eurasian Application Serial No. 200901078, Office Action mailed Sep. 21, 2011", (w/ English Translation), 4 pgs.

"Eurasian Application Serial No. 200901078, Response filed Jul. 29, 2013 to Office Action mailed Jan. 29, 2013", (w/ English Translation of Claims), 138 pgs.
"Eurasian Application Serial No. 200901078, Response filed Sep. 13, 2011 to Office Action mailed May 11, 2011", (w/ English Translation of Claims), 13 pgs.
"Eurasian Application Serial No. 201001264, Office Action mailed Mar. 20, 2013", (w/ English Translation), 3 pgs.
"Eurasian Application Serial No. 201001264, Office Action mailed Sep. 26, 2013", (w/ English Translation), 3 pgs.
"Eurasian Application Serial No. 201001264, Response filed Apr. 24, 2014 to Office Action mailed Sep. 26, 2013", w/English claims, 4 pgs.
"Eurasian Application Serial No. 201001264, Response filed Jun. 5, 2013 to Office Action mailed Mar. 20, 2013", (w/ English Translation of Amended Claims), 11 pgs.
"Eurasian Patent Application Serial No. 200901078, Response filed Mar. 21, 2012 to Office Action mailed Sep. 21, 2011", (w/ English Translation of Claims), 8 pgs.
"European Application Serial No. 12004181.9, European Search Report mailed Sep. 13, 2012", 8 pgs.
"European Application Serial No. 06813535.9, Examination Notification Art. 94(3) mailed Sep. 24, 2013", 4 pgs.
"European Application Serial No. 06813535.9, Extended Search Report mailed Oct. 24, 2011", 6 pgs.
"European Application Serial No. 06813535.9, Response filed May 14, 2012 to Extended Search Report mailed Oct. 24, 2011", 18 pgs.
"European Application Serial No. 06813535.9, Voluntary Amendment filed Apr. 22, 2008", 9 pgs.
"European Application Serial No. 07755916.9, Examination Notification Art. 94(3) mailed Aug. 15, 2013", 4 pgs.
"European Application Serial No. 07755916.9, Office Action mailed Mar. 25, 2014", 1 pg.
"European Application Serial No. 07755916.9, Office Action mailed Nov. 11, 2011", 1 pg.
"European Application Serial No. 07755916.9, Response filed May 18, 2012 to Extended Search Report mailed Oct. 25, 2011", 11 pgs.
"European Application Serial No. 07755916.9, Supplemental Search Report mailed Oct. 25, 2011", 9 pgs.
"European Application Serial No. 08799591.6, Office Action mailed May 21, 2012", 4 pgs.
"European Application Serial No. 08799591.6, Office Action mailed Jun. 4, 2010", 4 pgs.
"European Application Serial No. 08799591.6, Response filed Nov. 22, 2011 to Office Action mailed May 17, 2011", 26 pgs.
"European Application Serial No. 08799591.6, Response filed Dec. 2, 2010 to Office Action mailed Jun. 4, 2010", 20 pgs.
"European Application Serial No. 09709019.5, Examination Notification Art. 94(3) mailed Oct. 9, 2013", 6 pgs.
"European Application Serial No. 09709019.5, Extended European Search Report mailed Feb. 15, 2011", 8 pgs.
"European Application Serial No. 09709019.5, Notification of Loss of Rights mailed Oct. 21, 2011", 2 pgs.
"European Application Serial No. 09709019.5, Office Action mailed Mar. 19, 2013", 5 pgs.
"European Application Serial No. 09709019.5, Response filed Sep. 25, 2013 to Examination Notification Art. 94(3) mailed Mar. 19, 2013", 25 pgs.
"European Application Serial No. 09709019.5, Response filed Dec. 7, 2011 to Communication pursuant to 70(2) and 70a(2) EPC and the Notification of Loss of Rights mailed Oct. 21, 2011", 41 pgs.
"European Application Serial No. 12004181.9, Communication mailed Oct. 22, 2012", 2 pgs.
"European Application Serial No. 12004181.9, Communication pursuant to Rule 112(1) EPC mailed May 31, 2013", 1 pg.
"European Application Serial No. 12004181.9, Examination Notification Art. 94(3) mailed Sep. 2, 2013", 5 pgs.
"European Application Serial No. 12004181.9, Response filed Mar. 7, 2014 to Examination Notification Art. 94(3) mailed Sep. 2, 2013", 10 pgs.
"European Application Serial No. 12004181.9, Response filed Jul. 31, 2013 to Communication pursuant to Rule 112(1) EPC mailed May 31, 2013 and Communication mailed Oct. 22, 2012", 9 pgs.

(56) References Cited

OTHER PUBLICATIONS

"European Application Serial No. 13001957.3, Extended European Search Report mailed Jan. 28, 2014", 17 pgs.
"European Application Serial No. 13001957.3, Office Action mailed Mar. 3, 2014", 2 pgs.
"European Application Serial No. 08799591.6, Examination Notification Art. 94(3) mailed May 17, 2011", 5 pgs.
"I. Pharmaceutical Importance of Crystallin Hydrates", [online]. [retrieved on May 30, 2008]. Retrieved from the Internet: <URL: http://www.netlibrary.com/nlreader.dll?bookid=12783&filename=Page_126.html>, (2008), 126-127.
"Indian Application Serial No. 2064/delnp/2008, Examination Report mailed Aug. 21, 2012", 5 pgs.
"Indian Application Serial No. 5675/DELNP/2009, Voluntary Amendment filed Feb. 18, 2011", 7 pgs.
"International Application Serial No. PCT/US06/32371, International Preliminary Report on Patentability mailed Mar. 6, 2008", 6 pgs.
"International Application Serial No. PCT/US06/32371, International Search Report mailed Jul. 23, 2007", 3 pgs.
"International Application Serial No. PCT/US06/32371, Written Opinion mailed Jul. 23, 2007", 6 pgs.
"International Application Serial No. PCT/US2007/009840, International Preliminary Report on Patentability mailed Dec. 18, 2008", 9 pgs.
"International Application Serial No. PCT/US2007/009840, International Search Report mailed Aug. 5, 2008", 4 pgs.
"International Application Serial No. PCT/US2007/009840, Written Opinion mailed Aug. 5, 2008", 7 pgs.
"International Application Serial No. PCT/US2008/001631, International Preliminary Examination Report mailed Aug. 20, 2009", 12 pgs.
"International Application Serial No. PCT/US2008/001631, International Search Report mailed Jan. 21, 2009", 6 pgs.
"International Application Serial No. PCT/US2008/001631, Written Opinion mailed Jan. 21, 2009", 9 pgs.
"International Application Serial No. PCT/US2009/000771, International Preliminary Report on Patentability mailed Aug. 19, 2010", 8 pgs.
"International Application Serial No. PCT/US2009/000771, International Search Report mailed Aug. 28, 2009", 4 pgs.
"International Application Serial No. PCT/US2009/000771, Written Opinion mailed Aug. 28, 2009", 5 pgs.
"International Application Serial No. PCT/US2010/000369, International Search Report mailed Sep. 21, 2010", 6 pgs.
"International Application Serial No. PCT/US2010/000369, Partial International Search Report mailed Jul. 5, 2010", 6 pgs.
"International Application Serial No. PCT/US2010/000369, Written Opinion mailed Feb. 11, 2010", 9 pgs.
"International Application Serial No. PCT/US2010/000369, Written Opinion mailed Sep. 21, 2010", 9 pgs.
"Israel Application Serial No. 207246, Response filed Jun. 10, 2013 to Office Action mailed Feb. 10, 2013", (w/ English Translation of Claims), 7 pgs.
"Israeli Application Serial No. 200240, Examiner Report mailed Aug. 5, 2013", (English Translation), 3 pgs.
"Israeli Application Serial No. 200240, Response filed Nov. 25, 2013 to Examiner Report mailed Aug. 5, 2013", w/ English translation, 8 pgs.
"Japanese Application Serial No. 2008-528017, Preliminary Amendment filed Aug. 12, 2009", 26 pgs.
"Japanese Application Serial No. 2009-549102, Office Action mailed May 29, 2013", (w/ English Translation), 5 pgs.
"Japanese Application Serial No. 2009-549102, Response filed Mar. 22, 2013 to Office Action mailed Oct. 16, 2012", (w/ English Translation of Amended Claims), 7 pgs.
"Japanese Application Serial No. 2009-549102, Response filed Aug. 20, 2013 to Office Action mailed May 29, 2013", (w/ English Translation of Amended Claims), 5 pgs.
"Japanese Application Serial No. 2009-549102, Voluntary Amendment filed Feb. 7, 2011", (w/ English Translation of Amended Claims), 24 pgs.
"Japanese Application Serial No. 2010-545884, Amendment filed Jan. 23, 2012", (English Translation), 7 pgs.
"Japanese Application Serial No. 2010-545884, Office Action mailed Oct. 9, 2013", (w/ English Translation), 5 pgs.
"Japanese Application Serial No. 2010-545884, Voluntary Amendment filed Oct. 7, 2010", (w/ English Translation), 65 pgs.
"Japanese Application Serial No. 2013-59721, Office Action mailed May 30, 2014", 4 pgs.
"Japanese Patent Application Serial No. 2008-528017, Office Action mailed May 22, 2012", (English Translation), 4 pgs.
"Korean Application Serial No. 10-2010-7019944, Amendment filed Jan. 10, 2014", w/English claims, 31 pgs.
"Mexican Application Serial No. MX/a/2010/008697, Response filed Mar. 28, 2012 to Office Action mailed Nov. 28, 2011", (w/ English Translation of Claims), 22 pgs.
"Mexican Application Serial No. MX/a/2010/008697, Office Action mailed Nov. 28, 2011", (w/ English Translation), 7 pgs.
"Mexican Application Serial No. MX/a/2010/8697, Office Action mailed May 10, 2012", (English Translation), 3 pgs.
"Singapore Application Serial No. 201005638-0, Office Action mailed Jun. 27, 2012", 7 pgs.
"Singapore Application Serial No. 201005638-0, Office Action mailed Nov. 9, 2011", 16 pgs.
"Singapore Application Serial No. 201005638-0, Search Report mailed Oct. 27, 2011", 7 pgs.
"Singapore Application Serial No. 201005638-0, Written Opinion mailed Oct. 27, 2011", 8 pgs.
"Singapore Application Serial No. 201005638-0, Office Action Response filed Mar. 29, 2012 to Office Action mailed Nov. 9, 2011", (English Translation), 91 pgs.
Anders, H.-J., et al., "Molecular mechanisms of autoimmunity triggered by microbial infection", Arthritis Research & Therapy, 7(5), (2005), 215-224.
Baenziger, S., et al., "Triggering TLR7 in mice induces immune activation and lymphoid system disruption, resembling HIV-mediated pathology", Blood, 113(2), (Jan. 8, 2009), 377-388.
Brown, Gordon, "Dectin-1: a signalling non-TLR pattern-recognition receptor", Nature Reviews Immunology, (2006), 33-43.
Bryan, G. T., et al., "Interferon (IFN) and IFN Inducers Protect Mouse Bladder Urothelium Against Carcinogenicity by FANFT", Journal of Cancer Research and Clinical Oncology, 116(Suppl. Part 1), (Abstract A3.106.36), (15th International Cancer Congress, Hamburg, Aug. 16-22, 1990), (1990), p. 308.
Butler, Roslyn S, et al., "Highly fluorescent donor-acceptor purines", J. Mater. Chem., 17(19), (2007), 1863-1865.
Carson, D. A., et al., "TLR Agonists", Provisional U.S. Appl. No. 60/710,337, Application filed Aug. 22, 2005, 52 pgs.
Chan, Michael, et al., "Synthesis and Immunological Characterization of Toll-Lke Receptor 7 Agonistic Conjugates", Bioconjugate Chem., 20(6), (2009), 1194-1200.
Colombo, R., et al., "Combination of intravesical chemotherapy and hyperthermia for the treatment of superficial bladder cancer: preliminary clinical experience", Crit Rev Oncol Hematol., 47(2), (Aug. 2003), 127-39.
Dolan, M. E, et al., "Metabolism of 06-benzylguanine, an inactivator of O6-alkylguanine-DNA alkyltransferase.", Cancer Res., 54(19), (Oct. 1, 1994), 5123-30.
Hayashi, T., et al., "Mast cell-dependent anorexia and hypothermia induced by mucosal activation of Toll-like receptor 7", Am J Physiol Regul Integr Comp Physiol., 295(1), (2008), R123-32.
Jin, G., et al., "Synthesis and immunostimulatory activity of 8-substituted amino 9-benzyladenines as potent Toll-like receptor 7 agonists.", Bioorg Med Chem Lett., 16(17), (Sep. 1, 2006), 4559-4563.
Julien, R. M., "Chapter 2: Pharmacodynamics: How Drugs Act", A Primer of Drug Action (Ninth Edition); Worth Publishers, (2001), 37-57.
Kobayashi, H., et al., "Prepriming: a novel approach to DNA-based vaccination and immunomodulation", Springer Seminars in Immunopathology, 22(Nos. 1-2), (2000), 85-96.

(56) References Cited

OTHER PUBLICATIONS

Kulikov, V. I, et al., "Lipid derivatives of prostaglandins and nonsteroidal antiinflammatory drugs (a review)", Pharmaceutical Chemistry Journal, 31(4), (1997), 173-177.
Kurimoto, A., et al., "Synthesis and structure-activity relationships of 2-amino-8-hydroxyadenines as orally active interferon inducing agents", Bioorg Med Chem., 11(24), (Dec. 1, 2003), 5501-8.
Lee, J., et al., "Molecular basis for the immunostimulatory activity of guanine nucleoside analogs: Activation of Toll-like receptor 7", Proc. Natl. Acad. Sci., 100(11), (2003), 6646-6651.
Lippard, Stephen J, "The Art of chemistry", Nature, 416, (2002), 587.
Liu, H., et al., "Tumour growth inhibition by an imidazoquinoline is associated with c-Myc down-regulation in urothelial cell carcinoma", BJU International, 101(7), (Apr. 2008), 894-901.
Mayer, R., et al., "A randomized controlled trial of intravesical bacillus calmette-guerin for treatment refractory intersitial cystitis", Journal of Urology, 173(4), (Apr. 2005), 1186-1191.
Metzler, David E, "Biosynthesis of triglycerides and phospholipids", Biochemistry: The Chemical Reactions of Living Cells, (1977), 708.
Miller, R L, et al., "Imiquimod applied topically: a novel immune response modifier and new class of drug", Int J Immunopharmacol., 21(1), (Jan. 1999), 1-14.
Mosmann, T. R., et al., "TH1 and TH2 cells: different patterns of lymphokine secretion lead to different functional properties", Annual Review Immunology, 7, (1989), 145-173.
Rohn, S., et al., "Antioxidant activity of protein-bound quercetin", J Agric Food Chem., 52(15), (Jul. 28, 2004), 4725-9.
Schon, M., et al., "Tumor-Selective Induction of Apoptosis and the Small-Molecule Immune Response Modifier Imiquimod", J Natl Cancer Inst, 95(15), (2003), 1138-1149.
Sidky, Y. A., et al., "Curative effectiveness of the interferon inducing imiquimod as a signal agent in mouse bladder tumors", Proceedings, Eighty-Fourth Meeting of the American Association for Cancer Research, vol. 34, (Abstract 2789) (May 19-22, 1993, Orlando, FL), (Mar. 1993), 467.
Sidky, Y. A, et al., "Effects of Treatment with an Oral Interferon Inducer, Imidazoquinolinamine (R-837), on the Growth of Mouse Bladder Carcinoma FCB", Journal of Interferon Research, 10(Supp 1), (Abstract 116-12) (Annual Meeting of the ISIR, San Francisco, CA, Nov. 14-18, 1990), (Nov. 1990), S123.
Sidky, Y. A., et al., "Effects of treatment with the oral interferon inducer, R-837, on the growth of mouse colon carcinoma, MC-26", Proceedings, 81st Annual Meeting of the American Association for Cancer Research, vol. 31, (Abstract 2574), (Mar. 1990), p. 433.
Sidky, Y. A, et al., "Inhibition of murine tumor growth by an interferon-inducing imidazoquinolinamine", Cancer Research, 52(13), (Jul. 1, 1992), 3528-33.
Sidky, Y. A., et al., "Inhibition of tumor-induced angiogenesis by the interferon inducer Imiquimod", Proceedings, Eighty-Third Annual Meeting of the American Association of Cancer Research, vol. 33, (Abstract 458) (May 20-23, 1992, San Diego, CA), (Mar. 1992), p. 77.
Simons, M. P., et al., "Identification of the Mycobacterial Subcomponents Involved in the Release of Tumor Necrosis Factor-Related Apoptosis-Inducing Ligand from Human Neutrophils", Infection and Immunity, 75(3), (2007), 1265-1271.
Smith, E. B., et al., "Effects of Imiquimod, a toll-like receptor-7 agonist, on cell proliferation and cytokine production in bladder cancer in vitro and in vivo", Journal of Urology, 173(4, Suppl. S), (Apr. 2005), 158.
Smith, Eric B., et al., "Antitumor Effects of Imidazoquinolines in Urothelial Cell Carcinoma of the Bladder", The Journal of Urology, 177(6), (Jun. 2007), 2347-2351.
Spohn, R., et al., "Synthetic lipopeptide adjuvants and Toll-like receptor 2-structure-activity relationships", Vaccine, 22(19), (Jun. 23, 2004), 2494-9.
Staros, E. B., et al., "New Approaches to Understanding Its Clinical Significance", Am. J. Clin. Pathol., 123(2), (2005), 305-312.
Takeda, K., et al., "Toll-like receptors in innate immunity", International Immunology, 17(1), (2005), 1-14.
Tyagi, P., et al., "Local drug delivery to bladder using technology innovations", Urol Clin North Am., 33(4), (Nov. 2006), 519-530.
Veronese, F. M., et al., "The impact of PEGylation on biological therapies", BioDrugs, 22(5), (2008), 315-329.
Wille-Reece, U., et al., "HIV Gag protein conjugated to a Toll-like receptor 7/8 agonist improves the magnitude and quality of Th1 and CD8+ T cell responses in nonhuman primates", Proc. Natl. Acad. Sci. USA, 102(42), (Oct. 18, 2005), 15190-15194.
Wu, Christina C. N., et al., "Immunotherapeutic activity of a conjugate of a Toll-like receptor 7 ligand", Proc Natl Acad Sci USA., 104(10), (Mar. 6, 2007), 3990-3995.
Zaks, K, et al., "Efficient Immunization and Cross-Priming by Vaccine Adjuvants Containing TLR3 or TLR9 Agonists Complexed to Cationic Liposomes", Journal of Immunology, 176(12), (Jun. 15, 2006), 7335-7345.
"8H-Purin-8-one, 6-amino-2-(butylthio)-7,9-dihydro-9-(phenylmethyl)-", CAS Registry No. 226906-70-3, (2012), 1 pg.
"8H-Purin-8-one, 6-amino-2-(cyclohexylthio)-7,9-dihydro-9-(phenylmethyl)-", CAS Registry No. 226906-76-9, (2012).
"8H-Purin-8-one, 6-amino-2-(ethylthio)-7,9-dihydro-9-(phenylmethyl)-", CAS Registry No. 226906-67-8, (2012).
"8H-Purin-8-one, 6-amino-7,9-dihydro-2-(methylthio)-9-(phenylmethyl)-", CAS Registry No. 226906-66-7, (2012).
"8H-Purin-8-one, 6-amino-7,9-dihydro-2-(pentylthio)-9-(phenylmethyl)-", CAS Registry No. 226906-73-6, (2012).
"8H-Purin-8-one, 6-amino-7,9-dihydro-2-[(1-methylethyl)thio]-9-(phenylmethyl)-", CAS Registry No. 226906-69-0, (2012).
"8H-Purin-8-one, 6-amino-7,9-dihydro-2-[(1-methylpropyl)thio]-9-(phenylmethyl)-", CAS Registry No. 226906-72-5, (2012).
"8H-Purin-8-one, 6-amino-7,9-dihydro-2-[(2-methylbutyl)thio]-9-(phenylmethyl)-", CAS Registry No. 226906-75-8.
"8H-Purin-8-one, 6-amino-7,9-dihydro-2-[(2-methylpropyl)thio]-9-(phenylmethyl)-", CAS Registry No. 226906-71-4, (2012).
"8H-Purin-8-one, 6-amino-7,9-dihydro-2-[(3-methylbutyl)thio]-9-(phenylmethyl)-", CAS Registry No. 226906-74-7, (2012).
"8H-Purin-8-one, 6-amino-7,9-dihydro-9-(phenylmethyl)-2-(phenylthio)-", CAS Registry No. 226906-77-0, (2012).
"8H-Purin-8-one, 6-amino-7,9-dihydro-9-(phenylmethyl)-2-(propylthio)-", CAS Registry No. 226906-68-9, (2012).
"U.S. Appl. No. 12/064,529, Final Office Action mailed Sep. 20, 2012", 14 pgs.
"U.S. Appl. No. 12/302,738, Non Final Office Action mailed Jan. 2, 2013", 10 pgs.
"U.S. Appl. No. 12/302,738, Response filed Nov. 19, 2012 to Restriction Requirement mailed Oct. 19, 2012", 7 pgs.
"U.S. Appl. No. 12/302,738, Restriction Requirement mailed Oct. 19, 2012", 7 pgs.
"U.S. Appl. No. 12/367,172, Non Final Office Action mailed Jul. 1, 2014", 20 pgs.
"U.S. Appl. No. 12/367,172, Response filed Aug. 13, 2012 to Final Office Action mailed Apr. 13, 2012", 9 pgs.
"U.S. Appl. No. 12/704,343, Examiner Interview Summary mailed Feb. 7, 2013", 3 pgs.
"U.S. Appl. No. 12/704,343, Examiner Interview Summary mailed Feb. 25, 2013", 3 pgs.
"U.S. Appl. No. 12/704,343, Final Office Action mailed Dec. 7, 2012", 9 pgs.
"U.S. Appl. No. 12/704,343, Response filed Feb. 27, 2013 to Final Office Action mailed Dec. 7, 2012", 9 pgs.
"U.S. Appl. No. 12/704,343, Response filed Oct. 16, 2012 to Non Final Office Action mailed Jul. 16, 2012", 12 pgs.
"U.S. Appl. No. 12/704,343, Response filed Dec. 17, 2012 to Final Office Action mailed Dec. 7, 2012", 5 pgs.
"U.S. Appl. No. 13/682,208, Examiner Interview Summary mailed Sep. 11, 2014", 4 pgs.
"U.S. Appl. No. 13/682,208, Non Final Office Action mailed Nov. 5, 2014", 11 pgs.
"U.S. Appl. No. 13/682,208, Response filed Sep. 23, 2014 to Final Office Action mailed May 23, 2014", 9 pgs.
"U.S. Appl. No. 13/791,175, Final Office Action mailed Nov. 20, 2014", 12 pgs.
"U.S. Appl. No. 13/791,175, Non Final Office Action mailed Jul. 21, 2014", 11 pgs.

(56) References Cited

OTHER PUBLICATIONS

"U.S. Appl. No. 13/791,175, Response filed Jun. 26, 2014 to Final Office Action mailed Dec. 26, 2013", 9 pgs.
"U.S. Appl. No. 13/791,175, Response filed Oct. 21, 2014 to Non Final Office Action mailed Jul. 21, 2014", 7 pgs.
"Aromatic Ions (Chemgapedia)", [online]. [retrieved on Dec. 3, 2012]. Retrieved From Internet: <URL: http://www.chemgapedia.de/vsengine/vlu/vsc/en/ch/12/oc/vlu_organik/aromaten/aromaten/aromaten_gesamt.vlu/Page/vsc/en/ch/12/oc/aromaten/aromaten/ar_ionen/ar_ionen.vscml.html>, (2012), 2 pgs.
"Australian Application Serial No. 2006283524, Response filed Aug. 12, 2012 to Examiner Report mailed Aug. 3, 2011", 34 pgs.
"Canadian Application Serial No. 2,620,182, Office Action mailed Aug. 24, 2012", 5 pgs.
"Canadian Application Serial No. 2,653,941, Response filed Aug. 2, 2012 to Office Action mailed Feb. 8, 2012", 7 pgs.
"Canadian Application Serial No. 2,677,733, Office Action mailed Aug. 25, 2014", 2 pgs.
"Chinese Application Serial No. 200880011525.8, Office Action mailed Oct. 16, 2012", (w/ English Translation), 13 pgs.
"Chinese Application Serial No. 200880011525.8, Response filed Feb. 27, 2013 to Office Action mailed Oct. 16, 2012", (w/ English Translation of Amended Claims), 10 pgs.
"Chinese Application Serial No. 200880011525.8, Response filed Sep. 20, 2012 to Office Action mailed Jul. 5, 2012", (w/ English Translation of Claims), 12 pgs.
"Chinese Application Serial No. 200980112411.7, Office Action mailed Nov. 5, 2012", (English Translation), 8 pgs.
"Chinese Application Serial No. 200980112411.7, Office Action mailed Nov. 5, 2012", (w/ English Translation), 15 pgs.
"Chinese Application Serial No. 200980112411.7, Response filed Aug. 15, 2012 to Office Action mailed Feb. 2, 2012", (w/ English Translation of Amended Claims), 70 pgs.
"Chinese Application Serial No. 201080016320.6, Office Action mailed Mar. 20, 2014", w/English translation, 14 pgs.
"Chinese Application Serial No. 201080016320.6, Office Action mailed Jul. 8, 2013", (w/ English Translation), 16 pgs.
"Chinese Application Serial No. 201080016320.6, Response filed Nov. 25, 2013 to Office Action mailed Jul. 8, 2013", (w/ English Translation of Claims), 12 pgs.
"Definition: Micelle", Merriam-Webster, [Online]. Retrieved from the Internet: <URL:http://www.merriam-webster.com/dictionary/micelle>, (Accessed on Jun. 25, 2014), 1 pg.
"Eurasian Application Serial No. 201001264, Office Action mailed Sep. 12, 2012", (w/ English Summary), 2 pgs.
"Eurasian Application Serial No. 201101165, Office Action mailed Dec. 1, 2012", (w/ English Translation), 7 pgs.
"Eurasian Application Serial No. 200901078—Pending Claims", 2 pgs, (2013).
"Eurasian Application Serial No. 200901078, Response filed Jan. 16, 2013 to Office Action mailed Sep. 18, 2012", (w/ English Translation of Claims), 68 pgs.
"Eurasian Application Serial No. 201001264, Office Action mailed Jul. 10, 2014", 3 pgs.
"Eurasian Application Serial No. 201001264, Response filed Dec. 19, 2012 to Office Action mailed Sep. 12, 2012", (w/ English Translation of Amended Claims), 16 pgs.
"Eurasian Application Serial No. 201101165, Office Action mailed Jun. 28, 2013", (w/ English Translation), 3 pgs.
"Eurasian Application Serial No. 201101165, Response filed Apr. 9, 2013 to Office Action mailed Dec. 12, 2012", (w/ English Translation), 11 pgs.
"Eurasian Application Serial No. 201101165, Response filed Oct. 28, 2013 to Office Action mailed Jun. 28, 2013", (w/ English Translation of Amended Claims), 10 pgs.
"Eurasian Patent Application Serial No. 200901078, Response filed Aug. 2, 2012 to Office Action mailed Apr. 2, 2012", (w/ English Translation of Claims), 4 pgs.

"European Application Serial No. 06813535.9, Response filed Apr. 4, 2014 to Examination Notification Art. 94(3) mailed Sep. 24, 2013", 70 pgs.
"European Application Serial No. 07755916.9, Response filed May 23, 2014 to Examination Notification Art. 94(3) mailed Aug. 15, 2013", 13 pgs.
"European Application Serial No. 08799591.6, Response filed Sep. 20, 2012 to Office Action mailed May 21, 2012", 31 pgs.
"European Application Serial No. 09709019.5, Extended European Search Report mailed Feb. 15, 2011", 7 pgs.
"European Application Serial No. 10706399.2, Communication pursuant to Rules 16(1) and 162 EPC mailed Sep. 27, 2011", 2 pgs.
"European Application Serial No. 10706399.2, Examination Notification mailed Apr. 17, 2013", 4 pgs.
"European Application Serial No. 10706399.2, Examination Notification mailed Oct. 2, 2012", 6 pgs.
"European Application Serial No. 10706399.2, Response filed Mar. 21, 2013 to Examination Notification mailed Oct. 2, 2012", 11 pgs.
"European Application Serial No. 10706399.2, Response filed Aug. 13, 2013 to Examination Notification Art. 94(3) mailed Apr. 17, 2013", 12 pgs.
"European Application Serial No. 12004181.9, Examination Notification Art. 94(3) mailed Jul. 18, 2014", 4 pgs.
"European Application Serial No. 13001458.2, Communication pursuant to Rules 70(2) and 70a(2) EPC mailed Jul. 1, 2013", 1 pg.
"European Application Serial No. 13001458.2, Examination Notification Art. 94(3) mailed Apr. 14, 2014", 5 pgs.
"European Application Serial No. 13001458.2, Extended European Search Report mailed Apr. 22, 2013", 5 pgs.
"European Application Serial No. 13001458.2, Response filed Dec. 16, 2013 to Communication pursuant to Rules 70(2) and 70a(2) EPC mailed Jul. 1, 2013", 8 pgs.
"Indian Application Serial No. 5675/DELNP/2009, First Examiner Report mailed Sep. 11, 2014", 2 pgs.
"International Application Serial No. PCT/US2010/000369, International Preliminary Report on Patentability dated Jun. 28, 2011", 13 pgs.
"International Application Serial No. PCT/US2014/051090, International Search Report mailed Nov. 14, 2014", 4 pgs.
"International Application Serial No. PCT/US2014/051090, Written Opinion mailed Nov. 14, 2014", 4 pgs.
"Isolation/Modification/Labeling Product Sheet", Interchim Inc, (Jan. 15, 2000), 1-23.
"Israel Application Serial No. 207246, Office Action mailed May 27, 2014", 2 pgs.
"Israel Application Serial 207246, Office Action mailed Feb. 10, 2013", (English Translation), 2 pgs.
"Israel Application Serial No. 214572, Office Action mailed Jan. 2, 2014", (English Translation), 2 pgs.
"Israel Application Serial No. 214572, Office Action mailed Jul. 9, 2013", (English Translation), 3 pgs.
"Israel Application Serial No. 214572, Response filed Apr. 28, 2014 to Office Action mailed Jan. 2, 2014", English claims, 10 pgs.
"Israeli Application Serial No. 200240, Examiner Report mailed Aug. 28, 2012", (English Translation), 4 pgs.
"Israeli Application Serial No. 200240, Response filed Dec. 17, 2012 to Examiner Report mailed Aug. 28, 2012", (w/ English Translation of Claims), 4 pgs.
"Israeli Application Serial No. 214572, Office Action mailed Nov. 13, 2012", EN Office Action only, 2 pgs.
"Israeli Application Serial No. 214572, Response filed Nov. 3, 2013 to Office Action mailed Jul. 9, 2013", (English Translation of Claims), 5 pgs.
"Japanese Application Serial No. 2008-528017, Office Action mailed May 22, 2012", (w/ English Transation), 7 pgs.
"Japanese Application Serial No. 2008-528017, Response filed Nov. 20, 2012 to Office Action mailed May 22, 2012", (w/ English Translation of Amended Claims), 19 pgs.
"Japanese Application Serial No. 2009-549102, Office Action mailed Oct. 16, 2012", (w/ English Translation), 10 pgs.
"Japanese Application Serial No. 2010-545884, Examiners Decision of Final Refusal mailed Aug. 20, 2014", 6 pgs.

(56) References Cited

OTHER PUBLICATIONS

"Japanese Application Serial No. 2010-545884, Response filed Apr. 8, 2014 to Office Action mailed Oct. 9, 2013", w/English claims, 49 pgs.

"Japanese Application Serial No. 2011-549168, Amendment Filed Dec. 27, 2012", (English Translation of Claims), 6 pgs.

"Japanese Application Serial No. 2011-549168, Office Action mailed Jun. 2, 2014", w/English translation, 13 pgs.

"Korean Application Serial No. 10-2009-7018499, Office Action mailed Sep. 17, 2014", 8 pgs.

"Mexican Application Serial No. MX/a/2010/008697, Response filed Jul. 10, 2012 to Office Action mailed May 4, 2012", (w/ English Translation of Claims), 6 pgs.

"Mexican Application Serial No. MX/a/2011/008500, Office Action mailed Jun. 14, 2013", (English Translation), 1 pg.

"Mexican Application Serial No. MX/a/2011/008500, Response filed Oct. 24, 2013 to Office Action mailed Jun. 14, 2013", (w/ English Translation of Claims), 17 pgs.

"Singapore Application Serial No. 201005638-0, Response filed Aug. 22, 2012 to Office Action mailed Jun. 27, 2012", 2 pgs.

"Singapore Application Serial No. 201005638-0, Examination Report mailed Dec. 6, 2012", (English Translation), 6 pgs.

Jacobson, Kenneth A, et al., "Adenosine analogs with covalently attached lipids have enhanced potency at A1-adenosine receptors", FEBS Letters, 225(1-2), (1987), 97-102.

Kurimoto, A., et al., "Synthesis and evaluation of 2-substituted 8-hydroxyadenines as potent interferon inducers with improved oral bioavailabilities", Bioorg Med Chem., 12(5), (Mar. 1, 2004), 1091-9.

Takeda, K., et al., "Toll-like receptors", Annu Rev Immunol., 21, (2003), 335-76.

Wille-Reece, Ulrike, et al., "HIV Gag protein conjugated to a toll-like receptor 7/8 agonist improves the magnitude and quality of Th1 and CD8(+) T cell responses in nonhuman primates", (Oct. 2005), 15190-15194.

Yang, Victor C., et al., "Bioconjugates for Effective Drug Targeting", Advanced Drug Delivery Reviews 55 (2003), (2002), 169-170.

Zaks, Karen, et al., "Efficient immunization and cross-priming by vaccine adjuvants containing TLR3 or TLR9 agonists complexed to cationic liposomes", J Immunol., 176(12), (Jun. 15, 2006), 7335-45.

"Canadian Application Serial No. 2,677,733 Response filed Feb. 16, 2015 to Office Action mailed Aug. 25, 2014", 6 pgs.

FIG. 13

UC-1V150/MSA as anthrax spore vaccine adjuvant: (I) One immunization 6 days prior to infection $P < 0.0001$ Day post-infection % survival

▽ UC-1V150/MSA + IRS
◇ CT + IRS
● UC-1V150/MSA
✶ PBS

FIG. 15

| Cytokine | Time (h) | Conjugated | | | | | | Unconjugated | | | | | |
|---|---|---|---|---|---|---|---|---|---|---|---|---|---|
| | | BALF | | Serum | | Ratio | | BALF | | Serum | | Ratio | |
| | | ng/ml | SEM | ng/ml | SEM | | | ng/ml | SEM | ng/ml | SEM | | |
| IL-6 | 2 | 0.25 | 0.09 | 0.28 | 0.00 | 0.9 | | 0.73 | 0.40 | 5.00 | 1.14 | 0.1 | |
| | 4 | 1.34 | 0.38 | 0.06 | 0.02 | 22.1 | | 1.09 | 0.64 | 2.93 | 1.53 | 0.4 | |
| | 6 | 3.50 | 1.07 | 0.14 | 0.05 | 24.3 | | 3.00 | 0.76 | 3.95 | 1.24 | 0.8 | |
| | 24 | 4.06 | 0.41 | 0.03 | 0.00 | 117.2 | | 4.39 | 0.84 | 1.08 | 0.31 | 4.1 | |
| IL-12p40 | 2 | 0.06 | 0.00 | 0.23 | 0.03 | 0.2 | | 0.11 | 0.09 | 0.53 | 0.53 | 0.2 | |
| | 4 | 0.11 | 0.00 | 0.50 | 0.39 | 0.2 | | 0.06 | 0.03 | 0.23 | 0.23 | 0.3 | |
| | 6 | 0.29 | 0.04 | 0.25 | 0.06 | 1.1 | | 0.00 | 0.00 | 2.82 | 0.46 | 0.0 | |
| | 24 | 5.05 | 3.70 | 0.11 | 0.00 | 45.1 | | 0.01 | 0.01 | 0.49 | 0.47 | 0.0 | |
| TNF-a | 2 | 1.25 | 1.02 | 0.08 | 0.01 | 16.4 | | 2.62 | 0.83 | 0.52 | 0.21 | 5.0 | |
| | 4 | 9.67 | 1.01 | 0.02 | 0.01 | 580.1 | | 1.53 | 0.73 | 0.32 | 0.16 | 4.8 | |
| | 6 | 8.28 | 1.72 | 0.02 | 0.00 | 427.5 | | 2.03 | 0.67 | 0.39 | 0.15 | 5.2 | |
| | 24 | 4.22 | 2.80 | 0.01 | 0.00 | 551.8 | | 0.93 | 0.47 | 0.15 | 0.04 | 6.2 | |

Resiquimod (R848)

UC-1X105

UC-1V187

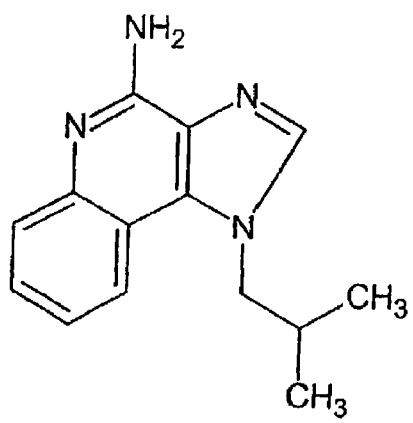
Imiquimod
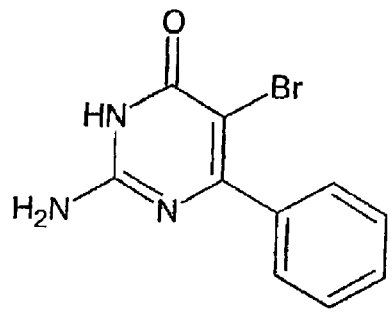
Bropirimine
*FIG. 28B*
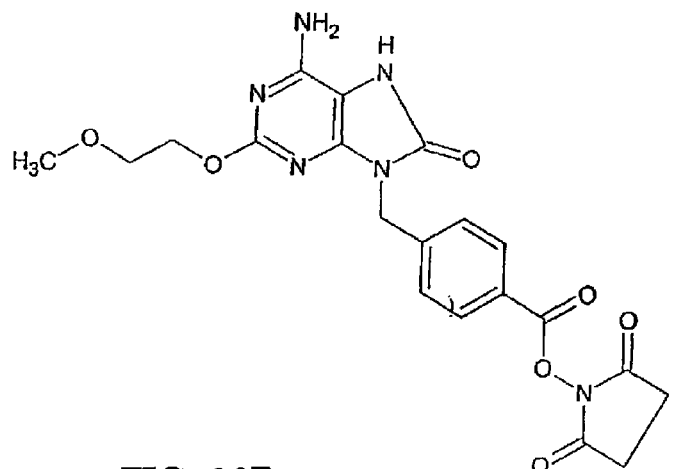
UC-1V199

UC-1W236

UC-1X51

Loxoribine

UC-1W247

UC-1X113

UC-1V186

CONJUGATES OF SYNTHETIC TLR AGONISTS AND USES THEREFOR

CROSS-REFERENCE TO RELATED APPLICATIONS

This application is continuation of and claims priority under 35 U.S.C. §120 to U.S. patent application Ser. No. 13/736,545, filed Jan. 8, 2013, which application is a divisional of and claims the benefit of priority under 35 U.S.C. §120 to U.S. patent application Ser. No. 12/027,960, filed on Feb. 7, 2008, now issued as U.S. Pat. No. 8,357,374, which application claims benefit of the filing date of U.S. application Ser. No. 60/888,699, filed on Feb. 7, 2007, all of which are incorporated by reference herein in their entireties.

STATEMENT OF GOVERNMENT RIGHTS

The invention described herein was made with government support under Grant Number AI056453 awarded by the National Institutes of Health. The United States Government has certain rights in the invention.

BACKGROUND

A great deal has been learned about the molecular basis of innate recognition of microbial pathogens in the last decade. It is generally accepted that many somatic cells express a range of pattern recognition receptors that detect potential pathogens independently of the adaptive immune system (see Janeway et al., *Annu Rev. Immunol.*, 20:197 (2002)). These receptors are believed to interact with microbial components termed pathogen associated molecular patterns (PAMPs). Examples of PAMPs include peptidoglycans, lipotechoic acids from gram-positive cell walls, the sugar mannose (which is common in microbial carbohydrates but rare in humans), bacterial DNA, double-stranded RNA from viruses, and glucans from fungal cell walls. PAMPs generally meet certain criteria that include, (a) their expression by microbes but not their mammalian hosts, (b) conservation of structure across the wide range of pathogens, and (c) the capacity to stimulate innate immunity. Toll-like Receptors (TLRs) have been found to play a central role in the detection of PAMPs and in the early response to microbial infections (see Underhill et al., *Curr. Opin. Immunol.*, 14:103 (2002)). Ten mammalian TLRs and a number of their agonists have been identified. For example, TLR7 and TLR9 recognize and respond to imiquimod and immunostimulatory CpG oligonucleotides (ISS-ODN), respectively. The synthetic immunomodulator R-848 (resiquimod) activates both TLR7 and TLR8. While TLR stimulation initiates a common signaling cascade (involving the adaptor protein MyD88, the transcription factor NF-kB, and pro-inflammatory and effector cytokines), certain cell types tend to produce certain TLRs. For example, TLR7 and TLR9 are found predominantly on the internal faces of endosomes in dendritic cells (DCs) and B lymphocytes (in humans; mouse macrophages express TLR7 and TLR9). TLR8, on the other hand, is found in human blood monocytes (see Hornung et al., *J. Immunol.*, 168:4531 (2002)).

Interferons (INFs) are also involved in the efficient induction of an immune response, especially after viral infection (Brassard et al., *J. Leukoc. Biol.*, 71:568 (2002)). However, many viruses produce a variety of proteins that block interferon production or action at various levels. Antagonism of interferon is believed to be part of a general strategy to evade innate, as well as adaptive immunity (see Levy et al., *Cytokine Growth Factor Rev.*, 12:143 (2001)). While TLR agonists may be sufficiently active for some methods of treatment, in some instances the microbial interferon antagonists could mitigate the adjuvant effects of synthetic TLR agonist.

A more specific response to microbial infections is based on active or passive immunization. If universal immunization is not considered cost-effective (or pharmacoeconomically viable), identification of a population at-risk that would benefit from immunoprophylaxis may be cost-effective, although identifying that population may be not straightforward. Nevertheless, there are some clearly defined at-risk populations for certain bacterial infections, such as staphylococcal infections, including dialysis patients, patients with ventriculoperitoneal shunts, patients at-risk of infective endocarditis, and residents of nursing homes, all of which suffer from chronic conditions that place them at a prolonged increased risk from staphylococcal infections. Many of these patients are also at increased risk for acquiring healthcare-associated methicillin-resistant *Staphylococcus aureus* (HA-MRSA). Blocking colonization of *Staphylococcus*, however, may be more achievable than protecting against infection.

Passive immunoprophylaxis using either polyclonal antibodies (Capparelli et al., *Antimicrob. Agents Chemo.*, 49:4121 (2005)) or monoclonal antibodies (mAbs) (www.biosynexus.com/productcandidates.html) may provide immediate (although short-term) protection for patients who either cannot wait for a vaccine effect to occur or whose immune systems are too compromised to mount a response to a vaccine. One potential indication for passive immunoprophylaxis is a hospital outbreak of MRSA-related infections. In such cases, exposed individuals may benefit from immediate prophylaxis, whereas individuals residing on the same ward or chronic care facility may benefit from active immunization. Moreover, intensive care unit patients are potential beneficiaries of passive immunoprophylaxis, as each of them would likely acquire one or more risk factors for staphylococcal infections.

SUMMARY OF THE INVENTION

The present invention provides for conjugates of a synthetic TLR agonist linked via a stable covalent bond to a macromolecule and compositions having those conjugates, as well as methods of using the conjugates. The conjugates may include macromolecules directly linked to a synthetic TLR agonist, e.g., TLR7 or TLR9 agonists, or linked via a linker to the TLR agonist, for instance, linked via an amino group, a carboxy group or a succinamide group. For instance, the conjugates of the invention include a synthetic TLR agonist (pharmacophore) covalently bound to a macromolecule such as, for instance, a peptide, polypeptide, e.g., an antibody or an antigen binding fragment thereof, lipid, a polymer such as polyethylene glycol, a bead, such as a polystyrene bead, or dendrimer. The conjugates of the invention are broad-spectrum, long-lasting, and non-toxic synthetic immunostimulatory agents, which are useful for activating the immune system of a mammal, e.g., a human. In particular, the conjugates of the invention optimize the immune response while limiting undesirable systemic side effects associated with unconjugated TLR agonists.

The synthetic TLR agonist may help direct the conjugate to TLRs within the endosomes of target cells and enhance delivery of the macromolecule. In one embodiment, the synthetic TLR agonist is specific for endosomal TLRs. In one embodiment, the TLR agonist may be a TLR7, TLR8, TLR3, or TLR9 agonist. Moreover, the synthetic TLR agonist may enhance the response to the macromolecule (e.g., immune response). Likewise, the macromolecule may be useful for activating the immune system and/or may direct the conjugate to particular cells. Thus, the macromolecule, e.g., one with a primary amino group that is linked to a synthetic TLR agonist, may enhance the activity of the synthetic TLR agonist or have a separate desirable activity. For example, the macromolecule may enhance the activity of the TLR agonist by helping to direct the agonist to the TLR within the endosomes of target cells, by enhancing signal transduction induced by the TLR agonist, or by cross-linking the receptor, or any combination thereof. In one embodiment, the macromolecule is a lipid which is spontaneously incorporated into liposomes. In one embodiment, the macromolecule is a nanoparticle which has amine groups on its surface. Once coupled to a TLR agonist, the TLR agonist-nanoparticle conjugate may be of a size, for instance, about 100 nm, that may reside (be present) in endosomes.

Hospital acquired *Staphylococcus aureus* (SA) infections are a major cause of morbidity and mortality. However, vaccines are not used in acute settings because they take too long to act and they are not effective in immunocompromised patients. The invention provides a method for the rapid vaccination of patients at-risk for gram-positive bacterial infections, e.g., SA infections, which employs Toll-like receptor-7 (TLR7) agonists and one or more antigens (immunogens) of a gram-positive bacteria. The use of the vaccines of the invention induces immunity in about 6 days, which provides for applications not amenable to standard vaccination protocol (e.g., acute care settings).

As disclosed herein, a composition comprising a gram-positive bacteria, *Bacillus anthracis* (BA), and a synthetic TLR7 agonist was prepared. The composition induced IL12 and IL6 secretion (indicative of activation of bone marrow derived macrophages (BMDM)) in vitro and protected mice versus subsequent, otherwise lethal intra-pulmonary BA challenge in vivo. In particular, the administration of a composition containing a TLR7 agonist conjugate and an immunogen (UC-IV199-albumin/irradiated BA spores) induced protective immunity to BA within 6 days. In contrast, injection of the animals with BA spores alone, or with BA plus a conventional adjuvant, i.e., cholera toxin (CT), did not protect the animals from a lethal challenger. The rapidity of a protective immune response in a naïve animal was unexpected.

The invention thus provides immunogenic compositions. In one embodiment, an immunogenic composition of the invention includes a synthetic TLR agonist such as a TLR7 agonist, e.g., UC-IV199, coupled to a gram-positive bacterial cell, for instance, coupled to free amino groups on killed *Staphylococcus aureus*; a synthetic TLR agonist such as a TLR7 agonist coupled to a bacterial extract of isolated gram-positive bacterial antigens; a synthetic TLR agonist such as a TLR7 agonist coupled to isolated gram-positive bacterial protein, e.g., recombinant protein; or a synthetic TLR agonist such as a TLR7 agonist coupled to isolated gram-positive bacterial carbohydrates. For example, a synthetic TLR7 agonist may be coupled to bacterial carbohydrates using methods to attach *Staphylococcus aureus* polysaccharides to protein carriers (such as those used for tetanus toxoid). The killed bacterial preparation may be prepared using gamma irradiation, heat or chemical treatment. In another embodiment, an immunogenic composition of the invention includes a synthetic TLR agonist such as a TLR7 agonist coupled to an adjuvant and a preparation comprising killed gram-positive bacterial cells; a synthetic TLR agonist such as a TLR7 agonist coupled to an adjuvant and a preparation comprising a gram-positive bacterial extract; or a synthetic TLR agonist such as a TLR7 agonist coupled to an adjuvant and a preparation comprising an isolated gram-positive bacterial antigen, e.g., recombinant protein. For example, the immunogenic composition may include UC-IV199 coupled to albumin and a preparation with killed gram-positive bacteria, e.g., killed *Staphylococcus aureus*. In one embodiment, an immunogenic composition of the invention includes a synthetic TLR7 agonist coupled to an adjuvant and a preparation comprising a recombinant gram-positive bacterial antigen, such as an isolated gram-positive bacterial protein or a peptide thereof, or isolated gram-positive bacterial carbohydrate. In one embodiment, a single dose of the immunogenic composition may show very potent activity, e.g., provide protective immunity, in a short period of time, e.g., less than about 10 days.

In one embodiment, a sterilized vaccine is administered to a subject from 0 to 7 days prior to hospitalization. In one embodiment, the vaccine is administered intramuscularly. In one embodiment, the vaccine is administered at a dosage between 10 μg and 10 mg.

The use of conjugates of synthetic TLR agonists such as TLR7 agonists of the invention is advantageous as accessible and versatile chemistry permits conjugation to any antigen, and modifiable conjugates have defined stoichiometry. The conjugates are inexpensive to prepare and are potent, and so provide rapid protection, enabling use in acute settings such as trauma, burn, pre-surgery, or bioterrorism.

Accordingly, there is provided a compound of formula (I):

(I)

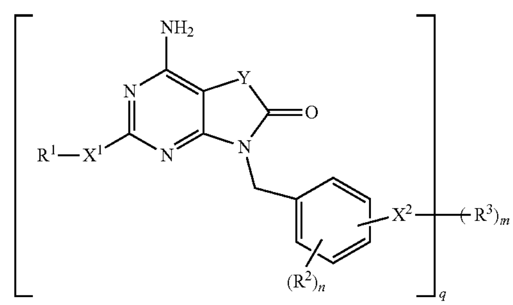

wherein $X^1$ is —O—, —S—, or —$NR^c$—;

wherein Y is S or NH;

wherein $R^c$ hydrogen, $C_{1-10}$alkyl, or $C_{1-10}$alkyl substituted by $C_{3-6}$cycloalkyl, or $R^c$ and $R^1$ taken together with the nitrogen atom can form a heterocyclic ring or a substituted heterocyclic ring, wherein the substituents are hydroxy, $C_{1-6}$alkyl, hydroxy$C_{1-6}$alkylene, $C_{1-6}$alkoxy, $C_{1-6}$alkoxy$C_{1-6}$alkylene, or cyano;

wherein $R^1$ is ($C_1$-$C_{10}$)alkyl, substituted ($C_1$-$C_{10}$)alkyl, $C_{6-10}$aryl, or substituted $C_{6-10}$aryl, $C_{5-9}$heterocyclic, substituted $C_{5-9}$heterocyclic;

wherein each $R^2$ is independently hydrogen, —OH, ($C_1$-$C_6$)alkyl, substituted ($C_1$-$C_6$)alkyl, ($C_1$-$C_6$)alkoxy, substituted ($C_1$-$C_6$)alkoxy, —C(O)—($C_1$-$C_6$)alkyl(alkanoyl), substituted —C(O)—($C_1$-$C_6$)alkyl, —C(O)—($C_6$-$C_{10}$)aryl (aroyl), substituted —C(O)—($C_6$-$C_{10}$)aryl, —C(O)OH (carboxyl), —C(O)O($C_1$-$C_6$)alkyl(alkoxycarbonyl), substituted —C(O)O($C_1$-$C_6$)alkyl, —$NR^aR^b$, —C(O)$NR^aR^b$ (carbamoyl), substituted —C(O)$NR^aR^b$, halo, nitro, or cyano;

wherein each $R^a$ and $R^b$ is independently hydrogen, ($C_1$-$C_6$)alkyl, ($C_3$-$C_8$)cycloalkyl, ($C_1$-$C_6$)alkoxy, halo($C_1$-$C_6$) alkyl, ($C_3$-$C_8$)cycloalkyl($C_1$-$C_6$)alkyl, ($C_1$-$C_6$)alkanoyl, hydroxy($C_1$-$C_6$)alkyl, aryl, aryl($C_1$-$C_6$)alkyl, Het, Het ($C_1$-$C_6$)alkyl, or ($C_1$-$C_6$)alkoxycarbonyl;

wherein $X^2$ is a bond or a linking group;

wherein R³ is a macromolecule;
wherein n is 1, 2, 3, or 4;
wherein m is 1, 2, 3 or more, e.g., 5, 10, 15, or more;
wherein q is 1, 2, 3 or up to about 1,000, about 10,000 or more, e.g., about 10⁵, about 10⁶ or greater; or a pharmaceutically acceptable salt thereof. In one embodiment, q is 1 and m is from 1 to 20 or any integer in between. In another embodiment, m is 1 and q is >2. In one embodiment, m is 1 and R³ may be a virus, e.g., a lentivirus other than simian immunodeficiency virus (SIV), a retrovirus, an influenza virus, a rhinovirus, a papilloma virus, a herpes virus and the like, a gram-positive bacterium or bacterial spore, a nanoparticle or a bead, e.g., a silica bead, and q is 10², 10³, 10⁴, 10⁵, 10⁶ or more. Thus, the conjugate may include multimers of the TLR agonist, the macromolecule, or both. The multimers may be linear or branched.

In one embodiment, R³ can be a macromolecule comprising a gram-positive bacteria, peptide of a gram-positive bacterium, protein of a gram-positive bacterium, carbohydrate of a gram-positive bacterium, or an adjuvant such as a heterologous protein or peptide, i.e., from a source other than the gram-positive bacteria, such as a host cell protein or peptide, e.g., albumin or ovalbumin, or a heterologous lipid, heterologous nucleic acid, nanoparticle, bead, such as a polystyrene bead, or dendrimer.

Thus, in various embodiments, m can be 1 or 2; and q can be 1 or 2. In some embodiments, m is 1 and the surface of the R³ group is linked to hundreds, thousands, or more, q groups. For example, the reactive sites of a silica particle can be used to link the silica particle to moieties of a formula described herein. For this configuration, the R³ can be any other macromolecule disclosed herein, such as a bead, nanoparticle, dendrimer, lipid, spore, or bacterial cell. In other embodiments, the formula and the group R³ can form an alternating chain of three to about ten repeating groups (e.g., formula-R³-formula-R³-formula-R³—, etc).

The macromolecule in the conjugates of the invention forms a stable bond with the TLR agonist, i.e., the conjugate does not act as a prodrug. The macromolecule can include organic molecules, composed of carbon, oxygen, hydrogen, nitrogen, sulfur, phosphorous, or any combination thereof, so long as the macromolecule is not harmful to body tissues (e.g., it is non-toxic, and/or does not cause inflammation). The macromolecule may permit targeting or enhance the immune response, e.g., the macromolecule may be an antigen such as a melanoma-specific peptide.

In various embodiments, when more than one R³ is present in a molecule of any formula described herein, each R³ may be the same, or the R³ groups may be different from each other. Accordingly, when more than one R³ group is present, each R³ is independently a group as defined for each formula.

In addition, the invention provides a pharmaceutical composition comprising at least one compound of formula (I), or a pharmaceutically acceptable salt thereof, in combination with a pharmaceutically acceptable diluent or carrier.

The invention includes the use of conjugates of a synthetic TLR agonist and a macromolecule, as well as TLR agonist conjugates and another molecule. The conjugate may be useful to prevent, inhibit or treat disorders including, but not limited to, allergic asthma, infectious diseases such as respiratory viral infections, e.g., those associated with influenza virus or respiratory syncytial virus (RSV) infection, lupus and other autoimmune diseases, and as a vaccine, e.g., for cancer or infectious diseases. In one embodiment, a single dose of the conjugate may show very potent activity in stimulating the immune response. Moreover, because of the low toxicity of the conjugates, in some circumstances higher doses may be administered, e.g., systemically, while under other circumstances lower doses may be administered, e.g., due to localization of the conjugate. In one embodiment, when administered at high doses, the synthetic TLR agonist conjugates may elicit an antagonistic response, and so may be useful to inhibit or treat asthma or autoimmune diseases. A first dose may elicit a hyperresponse which, in turn, suppresses the immune response, thereby avoiding inflammation. Thus, the use of higher doses and readministration may result in inhibition of an immune response.

In one embodiment, the invention provides a method to prevent or inhibit a gram-positive bacterial infection in a mammal. The method includes administering to the mammal an effective amount of a composition comprising a bacterial antigen of a gram-positive bacteria and an amount of a compound having formula (IA):

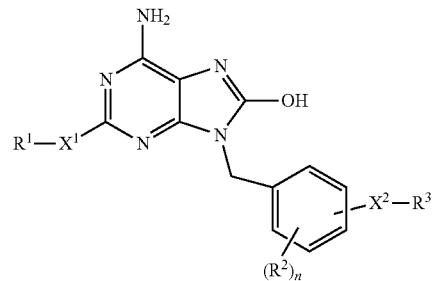

(IA)

wherein X¹ is —O—, —S—, or —NRᶜ—;
wherein Rᶜ is hydrogen, C₁₋₁₀alkyl, or substituted C₁₋₁₀alkyl, or Rᶜ and R¹ taken together with the nitrogen atom can form a heterocyclic ring or a substituted heterocyclic ring, wherein the substituents on the alkyl, aryl or heterocyclic groups are hydroxy, C₁₋₆alkyl, hydroxyC₁₋₆alkylene, C₁₋₆alkoxy, C₃₋₆cycloalkyl, C₁₋₆alkoxyC₁₋₆alkylene, amino, cyano, halogen, or aryl;
R¹ is hydrogen, (C₁-C₁₀)alkyl, substituted (C₁-C₁₀)alkyl, C₆₋₁₀aryl, or substituted C₆₋₁₀aryl, C₅₋₉heterocyclic, substituted C₅₋₉heterocyclic; wherein the substituents on the alkyl, aryl or heterocyclic groups are hydroxy, C₁₋₆alkyl, hydroxyC₁₋₆alkylene, C₁₋₆alkoxy, C₃₋₆cycloalkyl, C₁₋₆alkoxyC₁₋₆alkylene, amino, cyano, halogen, or aryl;
each R² is independently hydrogen, —OH, (C₁-C₆)alkyl, substituted (C₁-C₆)alkyl, (C₁-C₆)alkoxy, substituted (C₁-C₆)alkoxy, —C(O)—(C₁-C₆)alkyl(alkanoyl), substituted —C(O)—(C₁-C₆)alkyl, —C(O)—(C₆-C₁₀)aryl(aroyl), substituted —C(O)—(C₆-C₁₀)aryl, —C(O)OH (carboxyl), —C(O)O(C₁-C₆)alkyl(alkoxycarbonyl), substituted —C(O)O(C₁-C₆)alkyl, —NRᵃRᵇ, —C(O)NRᵃRᵇ (carbamoyl), substituted —C(O)NRᵃRᵇ, halo, nitro, or cyano; wherein the substituents on the alkyl, aryl or heterocyclic groups are hydroxy, C₁₋₆alkyl, hydroxyC₁₋₆alkylene, C₁₋₆alkoxy, C₃₋₆cycloalkyl, C₁₋₆alkoxyC₁₋₆alkylene, amino, cyano, halogen, or aryl;
each Rᵃ and Rᵇ is independently hydrogen, (C₁-C₆)alkyl, (C₃-C₈)cycloalkyl, (C₁-C₆)alkoxy, halo(C₁-C₆)alkyl, (C₃-C₈)cycloalkyl(C₁-C₆)alkyl, (C₁-C₆)alkanoyl, hydroxy (C₁-C₆)alkyl, aryl, aryl(C₁-C₆)alkyl, Het, Het (C₁-C₆) alkyl, or (C₁-C₆)alkoxycarbonyl;
X² is a bond or a linking group; n is 1, 2, 3, or 4; and R³ is a macromolecule comprising a heterologous peptide, heterologous protein, heterologous lipid, bead, such as a polystyrene bead, heterologous nucleic acid molecule or dendrimer;

or a pharmaceutically acceptable salt thereof, including hydrates thereof.

In certain embodiments, the definition of the group $R^1$ can be used interchangeably with the definition of the group $R^1$ for any other formula described herein.

Non-limiting examples of macromolecules or linkers therefore include not only an oxygen atom, a sulfur atom, a nitrogen atom or a carbon atom (and appropriately appended hydrogen atoms when necessary to fill valences) but also macromolecules or linkers with side chains that increase solubility, such as, for example, groups containing morpholino, piperidino, pyrrolidino, or piperazino rings and the like; amino acids, polymers of amino acids (proteins or peptides), e.g., dipeptides or tripeptides, and the like; carbohydrates (polysaccharides), nucleotides such as, for example, PNA, RNA and DNA, and the like; polymers of organic materials, such as, for example, polyethylene glycol, polylactide and the like; monomeric and polymeric lipids; insoluble organic nanoparticles; non-toxic body substances such as, for example, cells, lipids, antigens such as, for example microbes, such as, for example, viruses, bacteria, fungi, and the like. The antigens can include inactivated whole organisms, or sub-components thereof and the like.

Also provided is a method to prevent or inhibit a gram-positive bacterial infection in a mammal. The method includes administering to the mammal an effective amount of a compound having formula (IB):

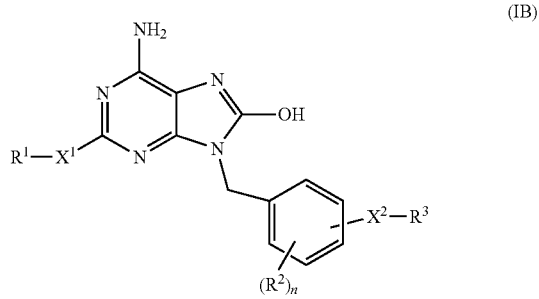

(IB)

wherein $X^1$ is —O—, —S—, or —$NR^c$—;
wherein $R^c$ is hydrogen, $C_{1-10}$alkyl, or substituted $C_{1-10}$alkyl, or $R^c$ and $R^1$ taken together with the nitrogen atom can form a heterocyclic ring or a substituted heterocyclic ring, wherein the substituents on the alkyl, aryl or heterocyclic groups are hydroxy, $C_{1-6}$alkyl, hydroxy$C_{1-6}$alkylene, $C_{1-6}$alkoxy, $C_{3-6}$-cycloalkyl, $C_{1-6}$alkoxy$C_{1-6}$alkylene, amino, cyano, halogen, or aryl;
$R^1$ is hydrogen, $(C_1-C_{10})$alkyl, substituted $(C_1-C_{10})$alkyl, $C_{6-10}$aryl, or substituted $C_{6-10}$aryl, $C_{5-9}$heterocyclic, substituted $C_{5-9}$heterocyclic; wherein the substituents on the alkyl, aryl or heterocyclic groups are hydroxy, $C_{1-6}$alkyl, hydroxy$C_{1-6}$alkylene, $C_{1-6}$alkoxy, $C_{3-6}$cycloalkyl, $C_{1-6}$alkoxy$C_{1-6}$alkylene, amino, cyano, halogen, or aryl;
each $R^2$ is independently hydrogen, —OH, $(C_1-C_6)$alkyl, substituted $(C_1-C_6)$alkyl, $(C_1-C_6)$alkoxy, substituted $(C_1-C_6)$alkoxy, —C(O)—$(C_1-C_6)$alkyl(alkanoyl), substituted —C(O)—$(C_1-C_6)$alkyl, —C(O)—$(C_6-C_{10})$aryl(aroyl), substituted —C(O)—$(C_6-C_{10})$aryl, —C(O)OH (carboxyl), —C(O)O$(C_1-C_6)$alkyl(alkoxycarbonyl), substituted —C(O)O$(C_1-C_6)$alkyl, —$NR^aR^b$, —C(O)$NR^aR^b$ (carbamoyl), substituted —C(O)$NR^aR^b$, halo, nitro, or cyano; wherein the substituents on the alkyl, aryl or heterocyclic groups are hydroxy, $C_{1-6}$alkyl, hydroxy$C_{1-6}$alkylene, $C_{1-6}$alkoxy, $C_{3-6}$cycloalkyl, $C_{1-6}$alkoxy$C_{1-6}$alkylene, amino, cyano, halogen, or aryl;
each $R^a$ and $R^b$ is independently hydrogen, $(C_1-C_6)$alkyl, $(C_3-C_8)$cycloalkyl, $(C_1-C_6)$alkoxy, halo$(C_1-C_6)$alkyl, $(C_3-C_8)$cycloalkyl$(C_1-C_6)$alkyl, $(C_1-C_6)$alkanoyl, hydroxy$(C_1-C_6)$alkyl, aryl, aryl$(C_1-C_6)$alkyl, Het, Het $(C_1-C_6)$alkyl, or $(C_1-C_6)$alkoxycarbonyl;
$X^2$ is a bond or a linking group; n is 1, 2, 3, or 4; and $R^3$ is the gram-positive bacteria, an isolated antigenic protein or peptide of the gram-positive bacteria, or an isolated polysaccharide of the gram-positive bacteria; or a pharmaceutically acceptable salt thereof, including hydrates thereof. In one embodiment, the gram-positive bacteria is a *Staphylococcus*.

In one embodiment, $R^3$ is an isolated antigenic protein or peptide of *Staphylococcus* and that compound is administered with a preparation of killed *Staphylococcus*.

The invention provides a compound of the invention for use in medical therapy (e.g., for prophylaxis of bacterial diseases such as in a vaccine). The compounds of the invention can also be used for biodefense, e., against *B. anthrax*.

Further provided are compositions and a compound of the invention for use in medical therapy, e.g., to treat asthma or viral infections or prevent viral infection, as well as the use of the conjugates for the manufacture of a medicament for the treatment of a TLR associated condition or symptom or one in which an augmented immune response or a suppressed immune response is indicated In addition, the invention also provides a pharmaceutical composition comprising at least one compound of the invention, or a pharmaceutically acceptable salt thereof, in combination with a pharmaceutically acceptable diluent or carrier, optionally in combination with a preparation of a selected gram-positive bacteria, e.g., a killed preparation or an extract, isolated protein of a selected gram-positive bacteria, or isolated carbohydrate (polysaccharide) of a selected gram-positive bacteria.

The invention includes the use of conjugates of TLR7 agonists and a macromolecule, e.g., one with a primary amino group, that enhances the activity of the agonist, e.g., albumin, or has a separate desirable activity, e.g., is an antigen of a gram-positive bacterium. The conjugates may include macromolecules directly linked to a TLR7 agonist, or linked via a linker to the TLR7 agonist. The conjugates may optimize the immune response while limiting undesirable systemic side effects of TLR7 agonists.

In one embodiment, the invention provides a method for preventing or treating a gram-positive bacterial infection in a mammal, such as a human. The method includes administering to a mammal in need of such therapy, an effective amount of a compound of the invention, or a pharmaceutically acceptable salt thereof, conjugated to an adjuvant or to at least one antigen of the gram-positive bacterium.

Also provided is a method to identify conjugates useful to prevent, inhibit or treat a particular condition or symptom, e.g., by identifying the cytokine profile induced by the conjugate in vitro or in vivo or by identifying the endosome, e.g., early, middle or late, having the TLR for the TLR agonist. As different cells have different endosomes, the identification of endosome patterns in cells may allow for targeting of conjugates to specific cell types or improve access of conjugates to endosomes.

BRIEF DESCRIPTION OF FIGURES

Figure 13:
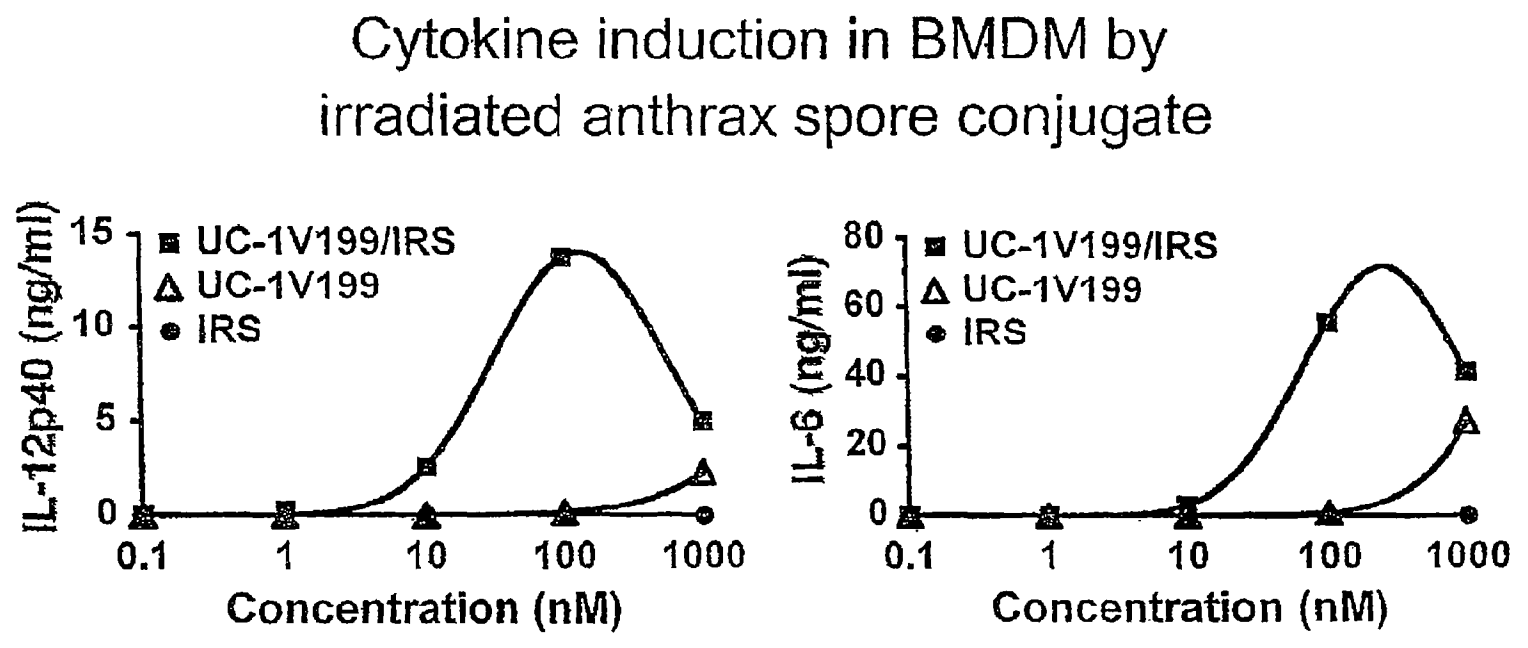

FIG. 13 shows cytokine induction in BMDM by irradiated anthrax spore-TLR7 agonist conjugate.

FIG. 15 provides a graph of percent survival after a single dose of vaccine with TLR7 agonists and conjugates.

FIG. 17 shows a local cytokine profile in mice. C57BL/6 mice were administered i.t. with a UC-1V150/MSA conjugate or unconjugated UC-1V136 at 3 nmole or 500 nmole per mouse, respectively. BALF and sera were collected at the indicated time points and cytokine levels determined by multiplex immunoassay. Mean values from at least 3-5 mice per group are shown ±SEM.

FIGS. 28A-D provide exemplary compounds for preparing conjugates of the invention or for use in the methods of the invention. A) Structures for UC-1V136, resiquimod, UC-1X105, and UC-1V187. B) Structures for imiquimod, bropirimine, and UC-1V199. C) Structures for UC-1W236, UC-1X51 and loxoribine. D) Structures for UC-1W247, UC-1X113 and UC-1V186. Other conjugates include TLR agonists coupled to human serum albumin, e.g., HSA/UC-1V150, or DOPE/UC-1V199. UC-1X-51 increases TNF-alpha levels three fold (110 ng/mL)

DETAILED DESCRIPTION OF INVENTION

Definitions

Figure 1:
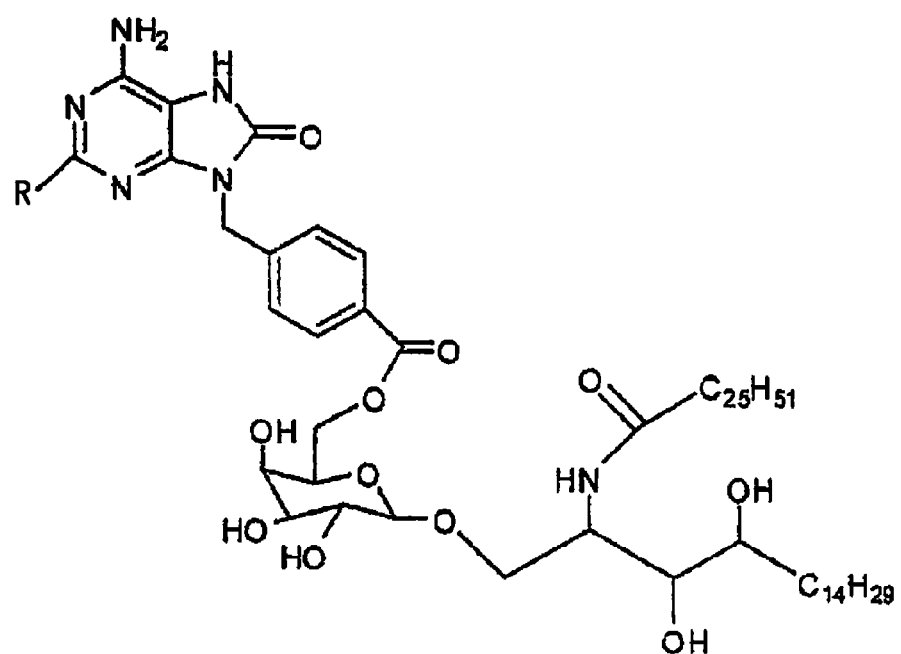
FIG. 1 shows a TLR agonist/alphagalactosyl-ceramide conjugate.
Figure 2:
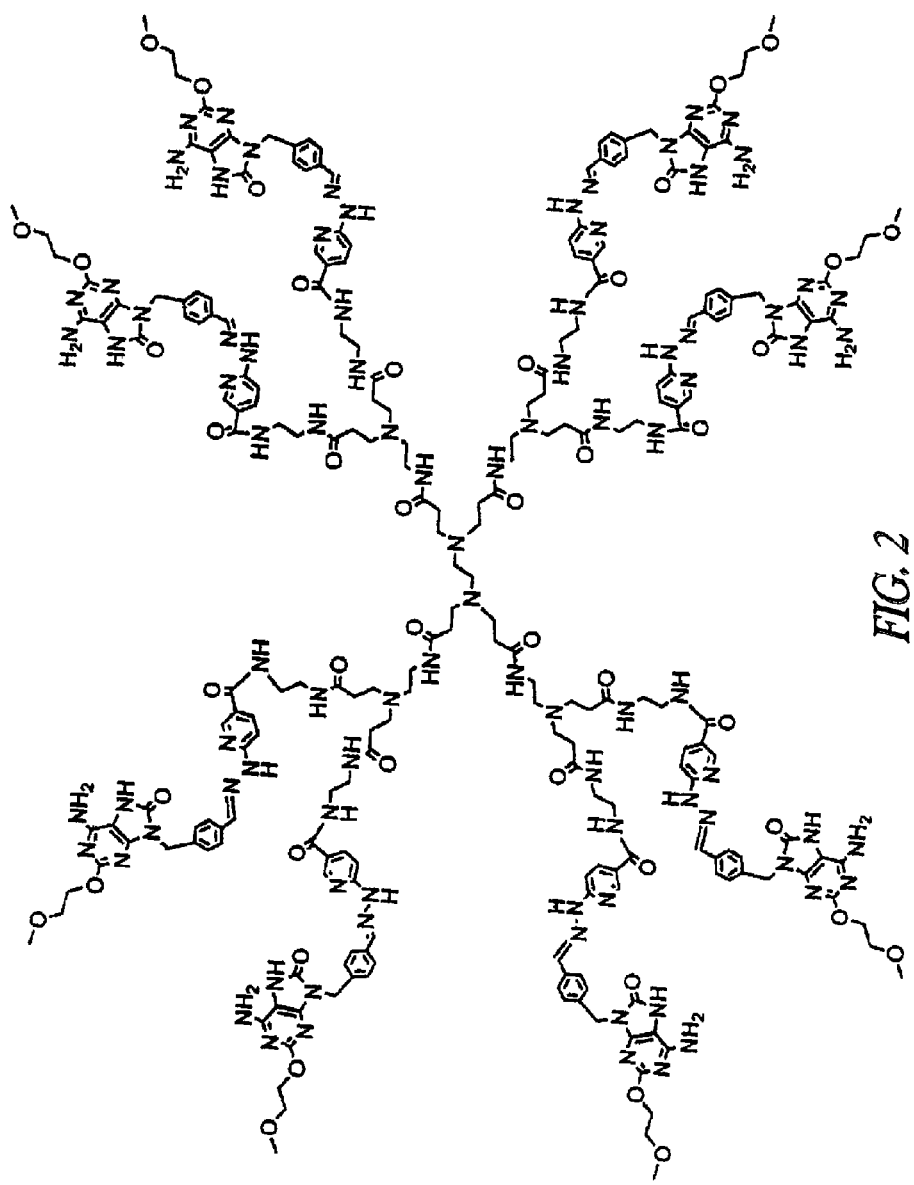
FIG. 2 illustrates a UC-1V150 conjugate of G1 PAMAM with an ethylene diamine core.

As used herein, the term "antibody" refers to a protein having one or more polypeptides substantially encoded by immunoglobulin genes or fragments of immunoglobulin genes. The recognized immunoglobulin genes include the kappa, lambda, alpha, gamma, delta, epsilon and mu constant region genes, as well as the myriad of immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD and IgE, respectively.

The basic immunoglobulin (antibody) structural unit is known to comprise a tetramer. Each tetramer is composed of two identical pairs of polypeptide chains, each pair having one "light" (about 25 kD) and one "heavy" chain (about 50-70 kD). The N-terminus of each chain defines a variable region of about 100 to 110 or more amino acids primarily responsible for antigen recognition. The terms variable light chain ($V_L$) and variable heavy chain ($V_H$) refer to these light and heavy chains respectively.

Antibodies may exist as intact immunoglobulins, or as modifications in a variety of forms including, for example, $FabFc_2$, Fab, Fv, Fd, $(FabN)_2$, an Fv fragment containing only the light and heavy chain variable regions, a Fab or $(Fab)N_2$ fragment containing the variable regions and parts of the constant regions, a single-chain antibody, e.g., scFv, CDR-grafted antibodies and the like. The heavy and light chain of a Fv may be derived from the same antibody or different antibodies thereby producing a chimeric Fv region. The antibody may be of animal (especially mouse or rat) or human origin or may be chimeric or humanized. As used herein the term "antibody" includes these various forms.

A composition is comprised of "substantially all" of a particular compound, or a particular form a compound (e.g., an isomer) when a composition comprises at least about 90%, and preferably at least about 95%, 99%, and 99.9%, of the particular composition on a weight basis. A composition comprises a "mixture" of compounds, or forms of the same compound, when each compound (e.g., isomer) represents at least about 10% of the composition on a weight basis. A purine analog of the invention, or a conjugate thereof, can be prepared as an acid salt or as a base salt, as well as in free acid or free base forms. In solution, certain of the compounds of the invention may exist as zwitterions, wherein counter ions are provided by the solvent molecules themselves, or from other ions dissolved or suspended in the solvent.

As used herein, the term "isolated" refers to in vitro preparation, isolation and/or purification of a nucleic acid molecule, a peptide or protein, or other molecule so that it is not associated with in vivo substances or is present in a form that is different than is found in nature. Thus, the term "isolated" when used in relation to a nucleic acid, as in "isolated oligonucleotide" or "isolated polynucleotide" refers to a nucleic acid sequence that is identified and separated from at least one contaminant with which it is ordinarily associated in its source. An isolated nucleic acid is present in a form or setting that is different from that in which it is found in nature. In contrast, non-isolated nucleic acids (e.g., DNA and RNA) are found in the state they exist in nature. For example, a given DNA sequence (e.g., a gene) is found on the host cell chromosome in proximity to neighboring genes; RNA sequences (e.g., a specific mRNA sequence encoding a specific protein), are found in the cell as a mixture with numerous other mRNAs that encode a multitude of proteins. Hence, with respect to an "isolated nucleic acid molecule", which includes a polynucleotide of genomic, cDNA, or synthetic origin or some combination thereof, the "isolated nucleic acid molecule" (1) is not associated with all or a portion of a polynucleotide in which the "isolated nucleic acid molecule" is found in nature, (2) is operably linked to a polynucleotide which it is not linked to in nature, or (3) does not occur in nature as part of a larger sequence. The isolated nucleic acid molecule may be present in single-stranded or double-stranded form. When a nucleic acid molecule is to be utilized to express a protein, the nucleic acid contains at a minimum, the sense or coding strand (i.e., the nucleic acid may be single-stranded), but may contain both the sense and anti-sense strands (i.e., the nucleic acid may be double-stranded).

The term "amino acid" as used herein, comprises the residues of the natural amino acids (e.g., Ala, Arg, Asn, Asp, Cys, Glu, Gln, Gly, His, Hyl, Hyp, Ile, Leu, Lys, Met, Phe, Pro, Ser, Thr, Trp, Tyr, and Val) in D or L form, as well as unnatural amino acids (e.g., phosphoserine, phosphothreonine, phosphotyrosine, hydroxyproline, gamma-carboxyglutamate; hippuric acid, octahydroindole-2-carboxylic acid, statine, 1,2,3,4,-tetrahydroisoquinoline-3-carboxylic acid, penicillamine, ornithine, citruline, -methyl-alanine, para-benzoylphenylalanine, phenylglycine, propargylglycine, sarcosine, and tert-butylglycine). The term also comprises natural and unnatural amino acids bearing a conventional amino protecting group (e.g., acetyl or benzyloxycarbonyl), as well as natural and unnatural amino acids protected at the carboxy terminus (e.g., as a ($C_1$-$C_6$)alkyl, phenyl or benzyl ester or amide; or as an -methylbenzyl amide). Other suitable amino and carboxy protecting groups are known to those skilled in the art (see for example, T. W. Greene, *Protecting Groups In Organic Synthesis*; Wiley: New York, 1981, and references cited therein). For instance, an amino acid can be linked to the remainder of a compound of formula I through the carboxy terminus, the amino terminus, or through any other convenient point of attachment, such as, for example, through the sulfur of cysteine.

The term "toll-like receptor" (TLR) refers to a member of a family of receptors that bind to pathogen associated molecular patterns (PAMPs) and facilitate an immune response in a mammal. Ten mammalian TLRs are known, e.g., TLR1-10.

The term "toll-like receptor agonist" (TLR agonist) refers to a molecule that binds to a TLR. Synthetic TLR agonists are chemical compounds that are designed to bind to a TLR and activate the receptor. Exemplary synthetic TLR agonists provided herein include "TLR-7 agonist", "TLR8 agonist", "TLR-3 agonist" and "TLR-9 agonist." TLR agonists include imiquimod, resiquimod, broprimine and loxoribine.

The term "nucleic acid" as used herein, refers to DNA, RNA, single-stranded, double-stranded, or more highly aggregated hybridization motifs, and any chemical modifications thereof. Modifications include, but are not limited to, those providing chemical groups that incorporate additional charge, polarizability, hydrogen bonding, electrostatic interaction, and fluxionality to the nucleic acid ligand bases or to the nucleic acid ligand as a whole. Such modifications include, but are not limited to, peptide nucleic acids (PNAs), phosphodiester group modifications (e.g., phosphorothioates, methylphosphonates), 2'-position sugar modifications, 5-position pyrimidine modifications, 7-position purine modifications, 8-position purine modifications, 9-position purine modifications, modifications at exocyclic amines, substitution of 4-thiouridine, substitution of 5-bromo or 5-iodouracil; backbone modifications, methylations, unusual base-pairing combinations such as the isobases, isocytidine and isoguanidine and the like. Nucleic acids can also include non-natural bases, such as, for example, nitroindole. Modifications can also include 3' and 5' modifications such as capping with a BHQ, a fluorophore or another moiety.

As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic residues such as amines; alkali or organic salts of acidic residues such as carboxylic acids; and the like. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic, and the like.

The pharmaceutically acceptable salts of the compounds useful in the present invention can be synthesized from the parent compound, which contains a basic or acidic moiety, by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in *Remington's Pharmaceutical Sciences,* 17th ed., Mack Publishing Company, Easton, Pa., p. 1418 (1985), the disclosure of which is hereby incorporated by reference.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication commensurate with a reasonable benefit/risk ratio.

The following definitions are used, unless otherwise described: halo or halogen is fluoro, chloro, bromo, or iodo. Alkyl, alkoxy, alkenyl, alkynyl, etc. denote both straight and branched groups; but reference to an individual radical such as "propyl" embraces only the straight chain radical, a branched chain isomer such as "isopropyl" being specifically referred to. Aryl denotes a phenyl radical or an ortho-fused bicyclic carbocyclic radical having about nine to ten ring atoms in which at least one ring is aromatic. Het can be heteroaryl, which encompasses a radical attached via a ring carbon of a monocyclic aromatic ring containing five or six ring atoms consisting of carbon and one to four heteroatoms each selected from the group consisting of non-peroxide oxygen, sulfur, and N(X) wherein X is absent or is H, O, $(C_1-C_4)$ alkyl, phenyl or benzyl, as well as a radical of an ortho-fused bicyclic heterocycle of about eight to ten ring atoms derived therefrom, particularly a benz-derivative or one derived by fusing a propylene, trimethylene, or tetramethylene diradical thereto.

It will be appreciated by those skilled in the art that compounds of the invention having a chiral center may exist in and be isolated in optically active and racemic forms. Some compounds may exhibit polymorphism. It is to be understood that the present invention encompasses any racemic, optically-active, polymorphic, or stereoisomeric form, or mixtures thereof, of a compound of the invention, which possess the useful properties described herein, it being well known in the art how to prepare optically active forms (for example, by resolution of the racemic form by recrystallization techniques, by synthesis from optically-active starting materials, by chiral synthesis, or by chromatographic separation using a chiral stationary phase) and how to determine agonist activity using the standard tests described herein, or using other similar tests which are well known in the art. It is also understood by those of skill in the art that the compounds described herein include their various tautomers, which can exist in various states of equilibrium with each other.

"Therapeutically effective amount" is intended to include an amount of a compound useful in the present invention or an amount of the combination of compounds claimed, e.g., to treat or prevent the disease or disorder, or to treat the symptoms of the disease or disorder, in a host. As used herein, "treating" or "treat" includes (i) preventing a pathologic condition from occurring (e.g. prophylaxis); (ii) inhibiting the pathologic condition or arresting its development; (iii) relieving the pathologic condition; and/or diminishing symptoms associated with the pathologic condition.

As used herein, the term "patient" refers to organisms to be treated by the methods of the present invention. Such organisms include, but are not limited to, mammals such as humans. In the context of the invention, the term "subject" generally refers to an individual who will receive or who has received treatment (e.g., administration of a compound of the invention).

"Stable compound" and "stable structure" are meant to indicate a compound that is sufficiently robust to survive isolation to a useful degree of purity from a reaction mixture, and formulation into an efficacious therapeutic agent. Only stable compounds are contemplated by the present invention.
The TLR Agonists and Conjugates of the Invention and Uses Thereof In one embodiment, the invention provides a therapeutic method for preventing or treating a pathological condition or symptom in a mammal, such as a human, wherein the activity of a TLR agonist is implicated and its action is desired. The method includes administering to a mammal in need of such therapy, an effective amount of a compound of the invention, or a pharmaceutically acceptable salt thereof. Non-limiting examples of pathological conditions or symptoms that are suitable for treatment include cancers, inflammatory diseases of the gastrointestinal tract, brain, skin, joints, and other tissues, bacterial or viral diseases, autoimmune diseases, and treating Crohn's Disease. The compounds of the invention can also be used to prepare vaccines against bacteria, viruses, cancer cells, or cancer-specific peptides, or to enhance anti-cancer monoclonal antibodies, as a CNS stimulant, or for biodefense. The invention thus provides a compound of the invention for use in medical therapy (e.g., for use as an anti-cancer agent, to treat bacterial diseases, to treat for viral diseases, such as hepatitis C and hepatitis B, to treat Crohn's Disease, and generally as therapeutic agents for treating immunologic disease). Furthermore, compounds of the invention may prevent carcinogenesis, e.g., by hepatitis C and hepatitis B viruses, and may be used for the manufacture of a medicament useful for the treatment of cancer, viral or bacterial infection, Crohn's Disease, and immunologic disorders in a mammal, such as a human.

In one embodiment, the present invention provides a method for treating a viral infection in a mammal by administering a TLR agonist conjugate of the invention. The viral infection may be caused by a RNA virus, a product of the RNA virus that acts as a TLR agonist, and/or a DNA virus. An exemplary DNA virus is hepatitis B virus. In one embodiment, the viral infection is caused by a coronavirus that causes Severe Acute Respiratory Syndrome (SARS), a Hepatitis B virus, or a Hepatitis C Virus.

In one embodiment, the present invention provides a method for treating cancer by administering an effective amount of a TLR agonist conjugate of the invention. The cancer may be an interferon sensitive cancer, such as, for example, a leukemia, a lymphoma, a myeloma, a melanoma, or a renal cancer. Specific cancers that can be treated include melanoma, superficial bladder cancer, actinic keratoses, intraepithelial neoplasia, and basal cell skin carcinoma, squamous, and the like. In addition, the method of the invention includes treatment for a precancerous condition such as, for example, actinic keratoses or intraepithelial neoplasia, familial polyposis (polyps), cervical dysplasia, cervical cancers, superficial bladder cancer, and any other cancers associated with infection (e.g., lymphoma Karposi's sarcoma, or leukemia); and the like.

In another embodiment, the present invention provides a method for treating an autoimmune disease by administering a therapeutically effective amount of a TLR agonist conjugate of the invention or a pharmaceutically acceptable salt of such a compound. Exemplary autoimmune diseases are Multiple Sclerosis, lupus, rheumatoid arthritis and the like.

In another embodiment, the present invention provides a method of treating Crohn's Disease by administering a TLR agonist conjugate of the invention.

The TLR agonist conjugates may include a homofunctional TLR agonist polymer, e.g., formed of a TLR7 agonist or a TLR3 agonist. The TLR7 agonist can be a 7-thia-8-oxoguanosinyl (TOG) moiety, a 7-deazaguanosinyl (7DG) moiety, a resiquimod moiety, or an imiquimod moiety. In another embodiment, the TLR agonist conjugate may include a heterofunctional TLR agonist polymer. The heterofunctional TLR agonist polymer may include a TLR7 agonist and a TLR3 agonist or a TLR9 agonist, or all three agonists. The heterofunctional TLR agonist polymer can include a TLR8 agonist and a TLR9 agonist.

The invention includes covalently conjugating a synthetic TLR agonist with selected macromolecules to achieve, for example, a desired molecular shape, size and valence in order to optimize the immunologic properties of the resulting conjugate, and/or to target or deliver the conjugate to desired cells and tissues. As described herein, the conjugates are designed to be useful in a variety of medical applications including, but not limited to, allergic asthma, respiratory viral infections (influenza and RSV), lupus and other autoimmune diseases, and as antigen-adjuvant combinations for vaccines against cancer and infectious diseases. The conjugates provide an optimum immune response while limiting undesirable systemic side effects by tethering the immune activator (the synthetic TLR agonist) to a macromolecule by a strong covalent bond. The macromolecule may serve as a targeting entity and/or an integral part of the immune response, such as the antigen in an adjuvant-antigen conjugate. A major advantage when administering a stable conjugate in a localized environment is that only very small amounts of TLR agonist are released over time into the systemic environment.

In one embodiment, the macromolecule is selected from products, such as proteins, lipids or dendrimers, or polymers having amino groups on their surfaces, such as polystyrene "amino beads," each having primary amino groups available for conjugation to a linker such as SANH, or for direct conjugation to the synthetic TLR7 agonist. For example, following conjugation of the linker and macromolecule, the TLR7 agonist, such as UC-1V150, is reacted with the NHS ester of the SANH-macromolecule conjugate to provide a TLR7 agonist-SANH-macromolecule conjugate.

Vaccines are not generally used in acute settings because (1) they take to long to act and (2) they are not effective in immune compromised patients. For example, *Staphylococcus aureus* (SA) infections are a major cause of morbidity and mortality in hospitalized patients. Groups particularly at risk are those with immune suppression due to burns, trauma, catheter placement, dialysis, or advanced age in nursing homes. Moreover, many strains of hospital acquired SA are resistant to conventional antibiotics.

The present invention overcomes these two barriers to treatment. The use of compositions, including synthetic TLR7 agonists and conjugates with synthetic TLR7 agonists, in combination with gram-positive bacterial antigens is provided herein. TLR7 ligands generally have poor pharmacokinetics, and rapid systemic absorption and excretion. Due to systemic dispersal, they result in cytokine syndrome. Effective adjuvants must create an "immune gradient" of cytokines and chemokines. In one embodiment, conjugation of potent synthetic TLR7 agonists to macromolecules enhances delivery properties, improves pharmacokinetics, and avoids systemic toxicity by localized exposure.

In one embodiment, the invention provides a method to prevent or inhibit a gram-positive bacterial infection in a mammal, comprising administering to the mammal an effective amount of a composition comprising a bacterial antigen of a gram-positive bacteria and an amount of a synthetic TLR7 agonist. In another embodiment, the invention provides a method to prevent or inhibit a gram-positive bacterial infection in a mammal, comprising administering to the mammal an effective amount of a synthetic TLR7 agonist conjugated to a gram-positive bacterial antigen. For example, a 1V150-MSA conjugate retains its TLR7 agonist activity, has enhanced potency and reduced toxicity, causes local activation of innate immunity, and induces T cell dependent immune protection within 6 days after a single vaccination with a bacterial antigen.

In one embodiment, a synthetic TLR7 agonist is administered with or conjugated to one or more antigens of *S. aureus*. Table 1 provides exemplary antigens for *S. aureus* for use with synthetic TLR7 agonists, particularly in acute care settings. The vaccines of the invention may unexpectedly provide a rapid and effective immune response.

TABLE 1

| *Staphylococcus aureus* immunogens |
|---|
| Weapon |
| Exfoliative toxin B |
| Exfoliative toxin A |
| Toxic shock-syndrome toxin |
| Enterotoxin A-E, H-U |
| Bone sialoprotein-binding protein |
| Collagen-binding protein |
| Clumping factor A |
| Clumping factor B |
| α-hemolysin |
| γ-hemolysin |
| Protein A |
| Clumping factor A |
| Fibronectin-binding protein A |
| Fibronectin-binding protein B |
| Collagen-binding protein |
| Lipoteichoic acid |
| Peptidoglycan |
| Protein A |
| Fibronectin-binding protein B |
| α-hemolysin |
| Panton valentine leukocidin |
| Collagen-binding protein |
| Lipoteichoic acid |
| Peptidoglycan |
| Capsular polysaccharide |
| Clumping factor A |
| Protein A |
| Fibronectin-binding proteins |

In one embodiment, the invention provides the following conjugates a compound of formula (II)

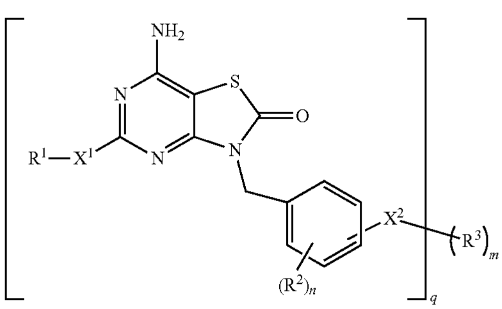

Thiazolopyrimidines

-continued a compound of formula (III)

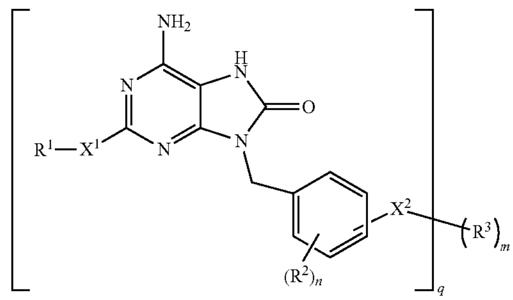

Purines $X^1$=—O—, —S—, or —$NR^c$—, wherein $R^c$ hydrogen, $C_{1-10}$alkyl, or $C_{1-10}$alkyl substituted by $C_{3-6}$ cycloalkyl, or $R^c$ and $R^1$ taken together with the nitrogen atom can form a heterocyclic ring or a substituted heterocyclic ring, wherein the substituents are hydroxy, $C_{1-6}$ alkyl, hydroxy $C_{1-6}$ alkylene, $C_{1-6}$ alkoxy, $C_{1-6}$ alkoxy $C_{1-6}$ alkylene, or cyano;

wherein $R^1$ is $(C_1\text{-}C_{10})$alkyl, substituted $(C_1\text{-}C_{10})$alkyl, $C_{6-10}$ aryl, or substituted $C_{6-10}$ aryl, $C_{5-9}$ heterocyclic, substituted $C_{5-9}$ heterocyclic; wherein the substituents on the alkyl, aryl or heterocyclic groups are hydroxy, $C_{1-6}$ alkyl, hydroxy $C_{1-6}$ alkylene, $C_{1-6}$ alkoxy, $C_{1-6}$ alkoxy $C_{1-6}$ alkylene, amino, cyano, halogen, or aryl;

each $R^2$ is independently hydrogen, —OH, $(C_1\text{-}C_6)$alkyl, substituted $(C_1\text{-}C_6)$alkyl, $(C_1\text{-}C_6)$alkoxy, substituted $(C_1\text{-}C_6)$ alkoxy, —C(O)—$(C_1\text{-}C_6)$alkyl(alkanoyl), substituted —C(O)—$(C_1\text{-}C_6)$alkyl, —C(O)—$(C_6\text{-}C_{10})$aryl(aroyl), substituted —C(O)—$(C_6\text{-}C_{10})$aryl, —C(O)OH (carboxyl), —C(O)O$(C_1\text{-}C_6)$alkyl(alkoxycarbonyl), substituted —C(O)O$(C_1\text{-}C_6)$alkyl, —$NR^aR^b$, —C(O)$NR^aR^b$ (carbamoyl), —O—C(O)$NR^aR^b$, —$(C_1\text{-}C_6)$alkylene-$NR^aR^b$, —$(C_1\text{-}C_6)$alkylene-C(O)$NR^aR^b$, halo, nitro, or cyano;

wherein each $R^a$ and $R^b$ is independently hydrogen, $(C_{1-6})$ alkyl, $(C_3\text{-}C_8)$cycloalky, $(C_{1-6}6)$alkoxy, halo$(C_{1-6})$alkyl, $(C_3\text{-}C_8)$cycloalkyl$(C_{1-6})$alkyl, $(C_{1-6})$alkanoyl, hydroxy$(C_{1-6})$ alkyl, aryl, aryl$(C_{1-6})$alkyl, aryl, aryl$(C_{1-6})$alkyl, Het, Het $(C_{1-6})$alkyl, or $(C_{1-6})$alkoxycarbonyl; wherein $X^2$ is a bond or a linking group; wherein $R^3$ is a macromolecule; wherein n is 1, 2, 3, or 4; wherein m is 1 or 2; wherein q is 1 to 1,000, $10^4$, $10^5$, $10^6$ or more; or a pharmaceutically acceptable salt thereof. The macromolecule groups can include organic molecules, composed of carbon, oxygen, hydrogen, nitrogen, sulfur, phosphorous, or combinations thereof, which are not harmful to body tissues (e.g., they are non-toxic, and/or do not cause inflammation) and may include, but not be limited to, dendrimers, proteins, peptides, lipids and their formulations (e.g., liposome nanoparticles), with or without linkers ($X^2$ groups), and amino-modified polymers, such as polystyrene beads, as well as α-galactosylceramides (see FIG. 1).

The compounds of the invention can be prepared using compounds having formula (IA-1):

(IA-1)

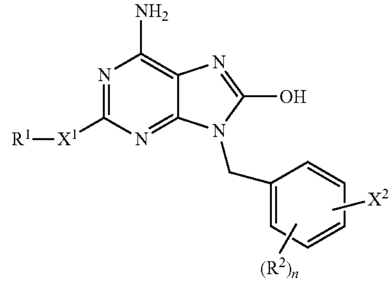

where $X^2$ is a group that can react to a specific group of compounds, e.g., those disclosed in U.S. Pat. No. 6,329,381 (Kurimoto et al.), or form a bond to a linking group or react to form a bond to a macromolecule, and the remaining variables are as defined above for formula (IA). Non-limiting examples of macromolecules include those with side chains that increase solubility, such as, for example, groups containing morpholino, piperidino, pyrrolidino, or piperazino rings and the like; amino acids, polymers of amino acids (proteins or peptides), e.g., dipeptides or tripeptides, and the like; carbohydrates (polysaccharides), nucleotides such as, for example, PNA, RNA and DNA, and the like; polymers of organic materials, such as, for example, polyethylene glycol, polylactide and the like; monomeric and polymeric lipids; insoluble organic nanoparticles; non-toxic body substances such as, for example, cells, lipids, vitamins, co-factors, antigens such as, for example microbes, such as, for example, viruses, bacteria, fungi, and the like. The antigens can include inactivated whole organisms, or sub-components thereof, e.g., cells and the like.

In one embodiment, a compound of the invention has formula (IC):

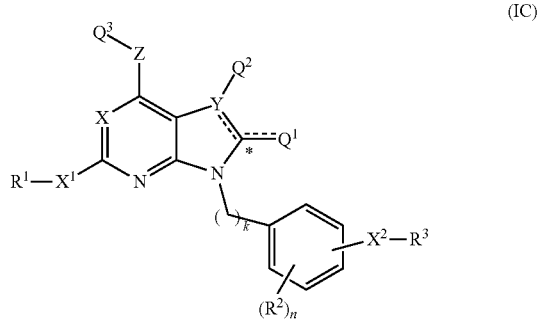

(IC)

wherein

X is N or $CR^x$ wherein $R^x$ is hydrogen, halogen, substituted alkyl, unsubstituted alkyl, substituted heteroalkyl, or unsubstituted heteroalkyl;

Y is S or N;

the dashes (----) indicate optional bonds; wherein:

when the bond between Y and the carbon marked by an asterisk is a double bond, $Q^2$ is not present;

when the bond between $Q^1$ and the carbon marked by an asterisk is a double bond, $Q^1$ is O, S, $NY^1$, or $NNY^2Y^3$; and when the bond between $Q^1$ and the carbon marked by an asterisk is a single bond, $Q^1$ is hydrogen, cyano, nitro, O—$Y^2$, S—$Y^2$, $NY'Y^2$, or $NY^2NY^3Y^4$; wherein $Y^1$ is hydrogen, substituted alkyl, unsubstituted alkyl, substituted cycloalkyl, unsubstituted cycloalkyl, substituted heteroalkyl, unsubstituted heteroalkyl, substituted aryl, unsubstituted aryl, substituted heteroaryl, unsubstituted heteroaryl, —C(=O)— substituted alkyl, —C(=O)— unsubstituted alkyl, —C(=O)O— substituted alkyl, —C(=O)O— unsubstituted alkyl, cyano, nitro, hydroxyl, or O—$Y^2$;

$Y^2$, $Y^3$, and $Y^4$, are each independently hydrogen, substituted alkyl, unsubstituted alkyl, substituted heteroalkyl, unsubstituted heteroalkyl, substituted aryl, unsubstituted aryl, substituted heteroaryl, unsubstituted heteroaryl;

Z is O, S, or $NY^5$ wherein $Y^5$ is hydrogen, substituted alkyl, unsubstituted alkyl, substituted heteroalkyl, unsubstituted heteroalkyl, substituted aryl, unsubstituted aryl, substituted heteroaryl, unsubstituted heteroaryl;

$Q^2$ and $Q^3$ are each independently hydrogen, substituted alkyl, unsubstituted alkyl, substituted heteroalkyl, unsubstituted heteroalkyl, substituted aryl, unsubstituted aryl, substituted heteroaryl, unsubstituted heteroaryl;

$X^1$ is —O—, —S—, or —$NR^c$—;

$R^c$ is hydrogen, $C_{1-10}$alkyl, or substituted $C_{1-10}$alkyl, or $R^c$ and $R^1$ taken together with the nitrogen atom can form a heterocyclic ring or a substituted heterocyclic ring;

$R^1$ is hydrogen, $(C_1-C_{10})$alkyl, substituted $(C_1-C_{10})$alkyl, $C_{6-10}$aryl, or substituted $C_{6-10}$aryl, $C_{5-9}$heterocyclic, or substituted $C_{5-9}$heterocyclic ring;

each $R^2$ is independently hydrogen, —OH, $(C_1-C_6)$alkyl, substituted $(C_1-C_6)$alkyl, $(C_1-C_6)$alkoxy, substituted $(C_1-C_6)$alkoxy, —C(O)—$(C_1-C_6)$alkyl(alkanoyl), substituted —C(O)—$(C_1-C_6)$alkyl, —C(O)—$(C_6-C_{10})$aryl(aroyl), substituted —C(O)—$(C_6-C_{10})$aryl, —C(O)OH (carboxyl), —C(O)O$(C_1-C_6)$alkyl(alkoxycarbonyl), substituted —C(O)O$(C_1-C_6)$alkyl, —$NR^aR^b$, —C(O)$NR^aR^b$ (carbamoyl), —O—C(O)$NR^aR^b$, —$(C_1-C_6)$alkylene-$NR^aR^b$, —$(C_1-C_6)$alkylene-C(O)$NR^aR^b$, halo, nitro, or cyano;

each $R^a$ and $R^b$ is independently hydrogen, $(C_1-C_6)$alkyl, $(C_3-C_8)$cycloalkyl, $(C_1-C_6)$heteroalkyl, $(C_1-C_6)$alkoxy, halo$(C_1-C_6)$alkyl, $(C_3-C_8)$cycloalkyl$(C_1-C_6)$alkyl, $(C_1-C_6)$alkanoyl, hydroxy$(C_1-C_6)$alkyl, aryl, aryl$(C_1-C_6)$alkyl, Het, Het $(C_1-C_6)$alkyl, or $(C_1-C_6)$alkoxycarbonyl;

wherein the substituents on any alkyl, cycloalkyl, heteroalkyl, amino, alkoxy, alkanoyl, aryl, heteroaryl, or heterocyclic groups are one or more (e.g., 1, 2, 3, 4, 5, or 6) hydroxy, $C_{1-6}$alkyl, hydroxy$C_{1-6}$alkylene, $C_{1-6}$alkoxy, $C_{3-6}$cycloalkyl, $C_{1-6}$alkoxy$C_{1-6}$alkylene, amino, cyano, halogen, heterocycle (such as piperidinyl or morpholinyl), or aryl;

$X^2$ is a bond or a linking group;

k is 0, 1, 2, 3, or 4;

n is 0, 1, 2, 3, or 4; and $R^3$ is a macromolecule comprising a cell, virus, vitamin, cofactor, peptide, protein, nucleic acid molecule, lipid, bead or particle, such as a polystyrene bead or nanoparticles, or a dendrimer;

or a pharmaceutically acceptable salt thereof, including hydrates thereof.

In certain embodiments, the groups $X^2$—$R^3$ can form a linker to a second formula (IC) moiety so as to form a dimer. For example, the linker can be any linker as described herein, such as a divalent aryl or heteroaryl, bis-amide aryl, bis-amide heteroaryl, bis-hydrazide aryl, bis-hydrazide heteroaryl, or the like. Alternatively, $Q^1$ can form a linker to a second formula (IC) moiety so as to form a dimer through a disulfide linkage. See for example, FIG. 28.

In cases where compounds are sufficiently basic or acidic to form acid or base salts, use of the compounds as salts may be appropriate. Examples of acceptable salts are organic acid addition salts formed with acids which form a physiological acceptable anion, for example, tosylate, methanesulfonate, acetate, citrate, malonate, tartarate, succinate, benzoate, ascorbate, α-ketoglutarate, and α-glycerophosphate. Suitable inorganic salts may also be formed, including hydrochloride, sulfate, nitrate, bicarbonate, and carbonate salts.

Acceptable salts may be obtained using standard procedures well known in the art, for example by reacting a sufficiently basic compound such as an amine with a suitable acid affording a physiologically acceptable anion. Alkali metal (for example, sodium, potassium or lithium) or alkaline earth metal (for example calcium) salts of carboxylic acids can also be made.

Alkyl includes straight or branched $C_{1-10}$ alkyl groups, e.g., methyl, ethyl, propyl, butyl, pentyl, isopropyl, isobutyl, 1-methylpropyl, 3-methylbutyl, hexyl, and the like.

Lower alkyl includes straight or branched $C_{1-6}$ alkyl groups, e.g., methyl, ethyl, propyl, 1-methylethyl, butyl, 1-methylpropyl, 2-methylpropyl, 1,1-dimethylethyl, pentyl, 1-methylbutyl, 2-methylbutyl, 3-methylbutyl, 1,1-dimethylpropyl, 1,2-dimethylpropyl, 2,2-dimethylpropyl, and the like.

The term "alkylene" refers to a divalent straight or branched hydrocarbon chain (e.g., ethylene: —CH$_2$—CH$_2$—).

$C_{3-7}$ Cycloalkyl includes groups such as, cyclopropyl, cyclopentyl, cyclohexyl, cycloheptyl, and the like, and alkyl-substituted $C_{3-7}$ cycloalkyl group, preferably straight or branched $C_{1-6}$ alkyl group such as methyl, ethyl, propyl, butyl or pentyl, and $C_{5-7}$ cycloalkyl group such as, cyclopentyl or cyclohexyl, and the like.

Lower alkoxy includes $C_{1-6}$ alkoxy groups, such as methoxy, ethoxy or propoxy, and the like.

Lower alkanoyl includes $C_{1-6}$ alkanoyl groups, such as formyl, acetyl, propanoyl, butanoyl, pentanoyl or hexanoyl, and the like.

$C_{7-11}$ aroyl, includes groups such as benzoyl or naphthoyl;

Lower alkoxycarbonyl includes $C_{2-7}$ alkoxycarbonyl groups, such as methoxycarbonyl, ethoxycarbonyl or propoxycarbonyl, and the like.

Lower alkylamino group means amino group substituted by $C_{1-6}$ alkyl group, such as, methylamino, ethylamino, propylamino, butylamino, and the like.

Di(lower alkyl)amino group means amino group substituted by the same or different and $C_{1-6}$ alkyl group (e.g., dimethylamino, diethylamino, ethylmethylamino).

Lower alkylcarbamoyl group means carbamoyl group substituted by $C_{1-6}$ alkyl group (e.g., methylcarbamoyl, ethylcarbamoyl, propylcarbamoyl, butylcarbamoyl).

Di(lower alkyl)carbamoyl group means carbamoyl group substituted by the same or different and $C_{1-6}$ alkyl group (e.g., dimethylcarbamoyl, diethylcarbamoyl, ethylmethylcarbamoyl).

Halogen atom means halogen atom such as fluorine atom, chlorine atom, bromine atom or iodine atom.

Aryl refers to a $C_{6-10}$ monocyclic or fused cyclic aryl group, such as phenyl, indenyl, or naphthyl, and the like.

Heterocyclic or heterocycle refers to monocyclic saturated heterocyclic groups, or unsaturated monocyclic or fused heterocyclic group containing at least one heteroatom, e.g., 0-3 nitrogen atoms (—NR$^d$— where R$^d$ is H, alkyl, or Y$^2$ as defined herein), 0-1 oxygen atom (—O—), and 0-1 sulfur atom (—S—). Non-limiting examples of saturated monocyclic heterocyclic group includes 5 or 6 membered saturated heterocyclic group, such as tetrahydrofuranyl, pyrrolidinyl, morpholinyl, piperidyl, piperazinyl or pyrazolidinyl. Non-limiting examples of unsaturated monocyclic heterocyclic group includes 5 or 6 membered unsaturated heterocyclic group, such as furyl, pyrrolyl, pyrazolyl, imidazolyl, thiazolyl, thienyl, pyridyl or pyrimidinyl. Non-limiting examples of unsaturated fused heterocyclic groups includes unsaturated bicyclic heterocyclic group, such as indolyl, isoindolyl, quinolyl, benzothizolyl, chromanyl, benzofuranyl, and the like. A Het group can be a saturated heterocyclic group or an unsaturated heterocyclic group, such as a heteroaryl group.

R$^c$ and R$^1$ taken together with the nitrogen atom to which they are attached can form a heterocyclic ring. Non-limiting examples of heterocyclic rings include 5 or 6 membered saturated heterocyclic rings, such as 1-pyrrolidinyl, 4-morpholinyl, 1-piperidyl, 1-piperazinyl or 1-pyrazolidinyl, 5 or 6 membered unsaturated heterocyclic rings such as 1-imidazolyl, and the like.

The alkyl, aryl, heterocyclic groups of R$^1$ can be optionally substituted with one or more substituents, wherein the substituents are the same or different, and include lower alkyl; cycloalkyl, hydroxyl; hydroxy $C_{1-6}$ alkylene, such as hydroxymethyl, 2-hydroxyethyl or 3-hydroxypropyl; lower alkoxy; $C_{1-6}$ alkoxy $C_{1-6}$ alkyl, such as 2-methoxyethyl, 2-ethoxyethyl or 3-methoxypropyl; amino; alkylamino; dialkyl amino; cyano; nitro; acyl; carboxyl; lower alkoxycarbonyl; halogen; mercapto; $C_{1-6}$ alkylthio, such as, methylthio, ethylthio, propylthio or butylthio; substituted $C_{1-6}$ alkylthio, such as methoxyethylthio, methylthioethylthio, hydroxyethylthio or chloroethylthio; aryl; substituted $C_{6-10}$ monocyclic or fused-cyclic aryl, such as 4-hydroxyphenyl, 4-methoxyphenyl, 4-fluorophenyl, 4-chlorophenyl or 3,4-dichlorophenyl; 5-6 membered unsaturated heterocyclic, such as furyl, pyrrolyl, pyrazolyl, imidazolyl, thiazolyl, thienyl, pyridyl or pyrimidinyl; and bicyclic unsaturated heterocyclic, such as indolyl, isoindolyl, quinolyl, benzothiazolyl, chromanyl, benzofuranyl or phthalimino. In certain embodiments, one or more of the above groups can be expressly excluded as a substituent of various other groups of the formulas.

In some embodiments, the five-membered ring of the formula is a thiazole ring, e.g., where Y of formula IA above is S and Q$^2$ is absent.

The alkyl, aryl, heterocyclic groups of R$^2$ can be optionally substituted with one or more substituents, wherein the substituents are the same or different, and include hydroxyl; $C_{1-6}$ alkoxy, such as methoxy, ethoxy or propoxy; carboxyl; $C_{2-7}$ alkoxycarbonyl, such as methoxycarbonyl, ethoxycarbonyl or propoxycarbonyl) and halogen.

The alkyl, aryl, heterocyclic groups of R$^c$ can be optionally substituted with one or more substituents, wherein the substituents are the same or different, and include $C_{3-6}$ cycloalkyl; hydroxyl; $C_{1-6}$ alkoxy; amino; cyano; aryl; substituted aryl, such as 4-hydroxyphenyl, 4-methoxyphenyl, 4-chlorophenyl or 3,4-dichlorophenyl; nitro and halogen.

The heterocyclic ring formed together with R$^c$ and R$^1$ and the nitrogen atom to which they are attached can be optionally substituted with one or more substituents, wherein the substituents are the same or different, and include $C_{1-6}$ alkyl; hydroxy $C_{1-6}$ alkylene; $C_{1-6}$ alkoxy $C_{1-6}$ alkylene; hydroxyl; $C_{1-6}$ alkoxy; and cyano.

In some embodiments, when Q$^1$ is O—Y$^2$, Y$^2$ is not hydrogen.

A specific value for X is N.

Another specific value for X is CH.

Of course, only one of the two bonds indicated by dashed lines may be present in one molecule of a compound of the indicated formula. In one embodiment, the bond between Y and the carbon marked by an asterisk is a double bond. In another embodiment, the bond between Q$^1$ and the carbon marked by an asterisk is a double bond.

A specific value for Q$^1$ is O.

Another specific value for Q$^1$ is S.

Another specific value for Q$^1$ is NY$^1$, for example, =NH.

Another specific value for Q$^1$ is NNY$^2$Y$^3$.

In one embodiment, the bond between Q$^1$ and the carbon marked by an asterisk is a single bond.

A specific value for Q$^1$ is hydrogen.

Another specific value for Q$^1$ is NH$_2$.

Another specific value for Q$^1$ is O—Y$^2$.

A specific value for Y$^1$ is hydrogen.

Another specific value for Y$^1$ is alkyl, for example, (C$_1$-C$_6$) alkyl, such as methyl.

Another specific value for Y$^1$ is aryl, such as phenyl.

A specific value for each of Y$^2$, Y$^3$, and Y$^4$ is hydrogen.

Another specific value for each of Y$^2$, Y$^3$, and Y$^4$ (independently) is alkyl, for example, (C$_1$-C$_6$)alkyl, such as methyl.

Another specific value for each of $Y^2$, $Y^3$, and $Y^4$ (independently) is aryl, such as phenyl.

A specific value for Z is O.

Another specific value for Z is S.

Another specific value for Z is $NY^5$ wherein $Y^5$ is hydrogen, methyl, or phenyl.

A specific value for $Q^2$ is hydrogen.

Another specific value for $Q^2$ is methyl, or phenyl.

A specific value for $Q^3$ is hydrogen.

Another specific value for $Q^3$ is methyl, or phenyl.

A specific value for $X^1$ is a sulfur atom, an oxygen atom or —$NR^c$—.

Another specific $X^1$ is a sulfur atom.

Another specific $X^1$ is an oxygen atom.

Another specific $X^1$ is —$NR^c$—.

Another specific $X^1$ is —NH—.

A specific value for Y is N.

Another specific value for Y is S.

A specific value for $R^c$ is hydrogen, $C_{1-4}$ alkyl or substituted $C_{1-4}$ alkyl.

A specific value for $R^1$ and $R^c$ taken together is when they form a heterocyclic ring or a substituted heterocyclic ring.

Another specific value for $R^1$ and $R^c$ taken together is substituted or unsubstituted morpholino, piperidino, pyrrolidino, or piperazino ring A specific value for $R^1$ is hydrogen, $C_{1-4}$alkyl, or substituted $C_{1-4}$alkyl.

Another specific $R^1$ is 2-hydroxyethyl, 3-hydroxypropyl, 4-hydroxybutyl, 2-aminoethyl, 3-aminopropyl, 4-aminobutyl, methoxymethyl, 2-methoxyethyl, 3-methoxypropyl, ethoxymethyl, 2-ethoxyethyl, methylthiomethyl, 2-methylthioethyl, 3-methylthiopropyl, 2-fluoroethyl, 3-fluoropropyl, 2,2,2-trifluoroethyl, cyanomethyl, 2-cyanoethyl, 3-cyanopropyl, methoxycarbonylmethyl, 2-methoxycarbonylethyl, 3-methoxycarbonylpropyl, benzyl, phenethyl, 4-pyridylmethyl, cyclohexylmethyl, 2-thienylmethyl, 4-methoxyphenylmethyl, 4-hydroxyphenylmethyl, 4-fluorophenylmethyl, or 4-chlorophenylmethyl.

Another specific $R^1$ is hydrogen, $CH_3$—, $CH_3$—$CH_2$—, $CH_3CH_2CH_2$—, hydroxy$C_{1-4}$alkylene, or $C_{1-4}$alkoxy$C_{1-4}$alkylene.

Another specific value for $R^1$ is hydrogen, $CH_3$—, $CH_3$—$CH_2$—, $CH_3$—O—$CH_2CH_2$— or $CH_3$—$CH_2$—O—$CH_2CH_2$—.

A specific value for $R^2$ is hydrogen, halogen, or $C_{1-4}$alkyl.

Another specific value for $R^2$ is hydrogen, chloro, bromo, $CH_3$—, or $CH_3$—$CH_2$—.

Specific substituents for substitution on the alkyl, aryl or heterocyclic groups are hydroxy, $C_{1-6}$alkyl, hydroxy$C_{1-6}$alkylene, $C_{1-6}$alkoxy, $C_{1-6}$alkoxy$C_{1-6}$alkylene, $C_{3-6}$cycloalkyl, amino, cyano, halogen, or aryl.

A specific value for $X^2$ is a bond or a chain having up to about 24 atoms; wherein the atoms are selected from the group consisting of carbon, nitrogen, sulfur, non-peroxide oxygen, and phosphorous.

Another specific value for $X^2$ is a bond or a chain having from about 4 to about 12 atoms.

Another specific value for $X^2$ is a bond or a chain having from about 6 to about 9 atoms.

Another specific value for $X^2$ is

[chemical structures]

Another specific value for $X^2$ is

[chemical structure]

In certain embodiments, the linker or the group $X^2$ is not a linker disclosed in PCT Application Publication No. WO 2007/024707. Additionally, in some embodiments, $R^3$ is not an auxiliary disclosed in PCT Application Publication No. WO 2007/024707.

A specific macromolecule is an amino acid, a carbohydrate, a peptide, a protein, an antigen, a nucleic acid, a lipid, a dendrimer, a body substance, or a cell such as a microbe.

A specific peptide, has from 2 to about 20 amino acid residues.

Another specific peptide, has from 10 to about 20 amino acid residues.

A specific macromolecule includes a carbohydrate.

A specific nucleic acid is DNA, RNA or PNA.

A specific macromolecule is a cell, lipid, vitamin, lipid, or co-factor.

A specific antigen is a microbe.

A specific microbe is a virus, bacteria, or fungi.

Another specific microbe is a virus or a bacteria.

Specific bacteria are *Bacillus anthracis, Listeria monocytogenes, Francisella tularensis, Salmonella,* or *Staphylococcus.*

Specific *Salmonella* are *S. typhimurium* or *S. enteritidis.*

Specific *Staphylococcus* include *S. aureus.*

Specific viruses are RNA viruses, including RSV and influenza virus, a product of the RNA virus, or a DNA virus, including herpes virus.

A specific DNA virus is hepatitis B virus.

In other embodiments, the macromolecule is not an amino acid, a carbohydrate, a peptide, an antigen such as a microbe, for example, a virus (for example, RNA viruses, e.g., SIV, hepatitis C virus or a coronavirus, a product of the RNA virus, or a DNA virus, such as Hepatitis B virus, fungi, or bacteria such as *Bacillus anthracis* (anthrax), *Listeria monocytogenes, Francisella tularensis,* or *Salmonella* (e.g., *typhimurium* or *enteritidis*), a nucleic acid such as DNA, RNA, PNA, or a body substance such as a cell or lipid.

A specific value for k is 0. Another specific value for k is 1. Another specific value for k is 2. In some embodiments, k is not 1.

Specific compounds of the invention have the general formula

IA-L-A$^1$;

IA-L-(A$^1$)$_2$;

IA-L-A$^1$-A$^1$;

IA-L-A$^1$-L-A$^1$;

(IA)$_2$-L-A$^1$-A$^1$;

(IA)$_2$-L-A$^1$-L-A$^1$;

(IA)$_2$-L-A$^1$; or (IA)$_2$-L-(A$^1$)$_2$;

wherein IA is as disclosed herein; L is absent or is a linking group; and each A$^1$ group independently represents a macromolecule.

The invention includes compositions of a compound of the invention optionally in combination with other active agents, e.g., ribavirin, mizoribine, and mycophenolate mofetil. Other non-limiting examples are known and are disclosed in U.S. published patent application No. 20050004144.

Processes for preparing compounds of the invention for preparing intermediates useful for preparing compounds of the invention are provided as further embodiments of the invention. Intermediates useful for preparing compounds of the invention are also provided as further embodiments of the invention.

For example, the compounds (conjugates) of the invention can be prepared using standard synthetic methods known in the art. A general ester and aldehyde synthesis is illustrated below. UC-1V150 was synthesized in seven steps from 2,6-dichloropurine. The free aldehyde group on the benzyl moiety of UC-1V150 enabled us to couple the agonist to many different auxiliary chemical entities, including proteins, oligonucleotides, aromatic molecules, lipids, viruses, and cells, through a linker molecule that contained a hydrazine or amino group.

General Synthesis

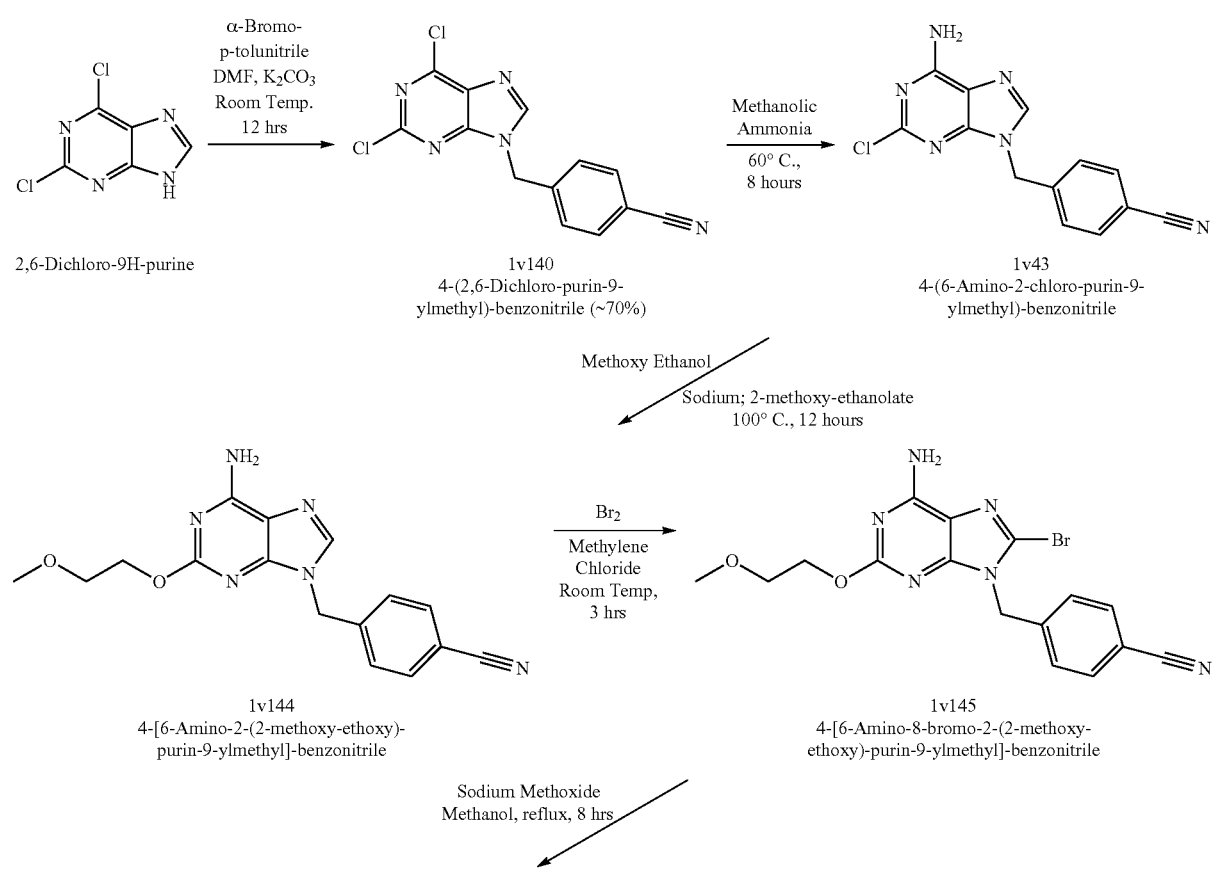

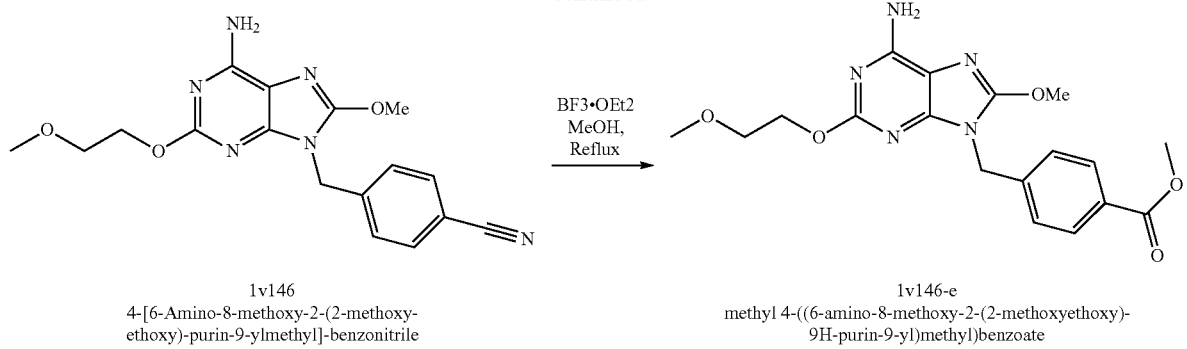

NHS Ester Synthesis

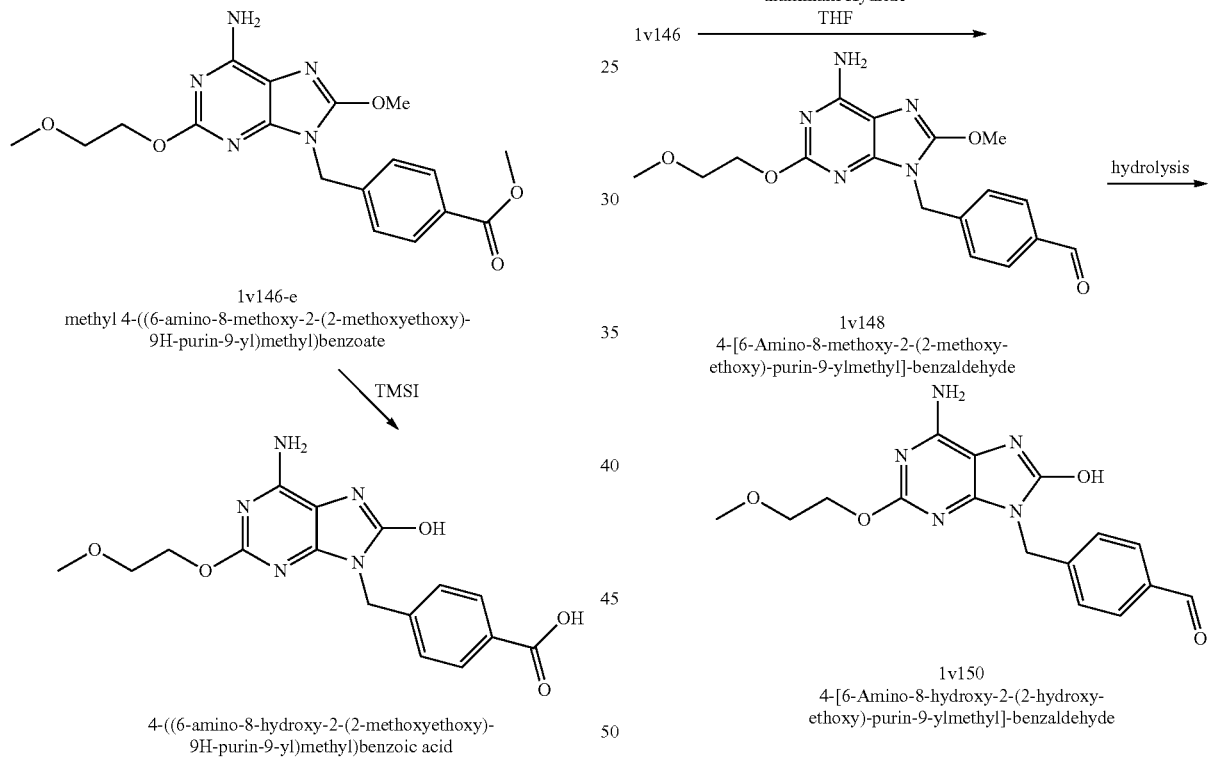

Aldehyde Synthesis

Chemistry of UC-1V150.

The synthesis of UC-1V150 and the preparation of the indicated compounds 2-8 was as follows. Compound 2: 4-(2, 6-dichloropurin-9-ylmethyl)benzonitrile. 2,6-dichloro-9H-purine (1, 16 mmol) was dissolved in DMF (50 mL) with potassium carbonate (50 mmol) added, and the mixture was stirred at ambient temperature for 16 hours after adding α-Bromo-p-tolunitrile (22 mmol). After filtration to remove insoluble inorganic salts, the filtrate was poured into water (1500 mL) and extracted with ethyl acetate (2×400 mL), dried over magnesium sulfate and evaporated to yield a residue which was subjected to flash silica gel chromatography using 1:2:10 ethyl acetate/acetone/hexanes. Yield 3.33 g (69%). UV, NMR and MS were consistent with structure assignment. Compound 3: 4-(6-amino-2-chloropurin-9-ylmethylben-zonitrile. Compound 2 (1.9 g) was placed in a steel reaction vessel and methanolic ammonia (80 mL, 7 N) was added. The sealed vessel was heated at 60° C. for 12 hours, cooled in ice and the solid product filtered off. Yield 1.09 g. UV, NMR and MS were consistent with assigned structure. Compound 4: 4-[6-amino-2-(2-methoxyethoxy)purin-9-ylmethyl]benzonitrile. The sodium salt of 2-methoxyethanol was first generated by dissolving sodium metal (81 mg) in 2-methoxyethanol (30 mL) with heat, and then compound 3 (1.0 g) dissolved in methoxyethanol was added (300 mL, with heat). The reaction mixture was heated for 8 hours at 115° C. bath temperature, concentrated in vacuo to near dryness and the residue partitioned between ethyl acetate and water. Flash silica gel chromatography of the organic layer using 5% methanol in dichloromethane gave 763 mg product. NMR was consistent with structure assignment. Compound 5: 4-[6-amino-8-bromo-2-(2-methoxyethoxy)purin-9-ylmethyl]benzonitrile. Compound 4 (700 mg) was dissolved in dichloromethane (400 mL) and bromine (7 mL) was added dropwise. The mixture was stirred overnight at room temperature and extracted first with aqueous sodium thiosulfate (2 L of 0.1 M) solution, then with aqueous sodium bicarbonate (500 mL, saturated). The residue from the organic layer was chromatographed on silica gel using 3% methanol in dichloromethane to yield 460 mg of bromo product. NMR, W and MS were consistent with structure assignment. Compound 6: 4-[6-amino-8-methoxy-2-(2-methoxyethoxy)purin-9-ylmethyl]benzonitrile. Sodium methoxide was generated by reaction of sodium metal (81 mg) in dry methanol (30 mL) and combined with a solution of compound 5 (700 mg) dissolved in dry dimethoxyethane and the temperature raised to 100° C. After overnight reaction, the mixture was concentrated in vacuo and the residue was chromatographed on silica using 5% methanol in dichloromethane. Yield 120 mg. NMR was consistent with structure assignment. Compound 7: 4-[6-amino-8-methoxy-2-(2-methoxyethoxy)purin-9-ylmethyl]benzaldehyde. Compound 6 (100 mg) was dissolved in dry THF (3 mL) and cooled to 0° C. under argon. The reducing agent, lithium N,N'-(dimethylethylenediamino)aluminum hydride, used to convert the nitrile to the aldehyde function. A 0.5 M solution in dry THF was prepared and 0.72 mL of such was added to the reaction flask. The mixture was stirred at 0-5° C. for 1 hour, quenched by addition of 3 M HCl, extracted with ethyl acetate followed by dichloromethane, and then concentrated in vacuo to yield 85 mg. NMR was consistent with structure assignment. Compound 8: 4-[6-amino-8-hydroxy-2-(2-methoxyethoxy)purin-9-ylmethyl]benzaldehyde (UC-1V150). Compound 7 (800 mg) was combined with sodium iodide (504 mg) and acetonitrile (40 mL), and chlorotrimethylsilane (0.5 mL) was slowly added. The mixture was heated at 70° C. for 3.5 hours, cooled and filtered. The solid product was washed with water, then ether, to yield 406 mg. NMR, UV, and MS were consistent with structure assignment.

Additional examples for preparing specific compounds are included herein.

As described in the examples herein, a soluble TLR7 agonist capable of covalent coupling to primary amines under physiologic conditions was prepared. The in vitro activity of several compounds and antigen-adjuvant complexes was then tested utilizing bone marrow-derived murine or peripheral blood mononuclear cell-derived dendritic cells (DC) to characterize DC maturation and cytokine secretion (e.g., IL-12, IL-6, TGF-beta, and IFN-gamma). Immunocompetent syngeneic C57/B1 mice were prophylactically vaccinated with intradermal antigen-TLR7 agonist complexes and challenged with B16 melanoma tumor cells expressing the cOVA transgene.

The effective concentration ($EC_{50}$) for each compound generally followed a bell shaped distribution with higher doses being inhibitory. Maximal stimulation occurred between 10 and 1000 nM. Covalently coupled adjuvant molecules to TLR agonist retained activity but with generally lower $EC_{50}$ values. Coupling UC-1V199 to chicken ovalbumin nearly doubled median survival from 22 to 35 days following subcutaneous tumor challenge compared with chicken ovalbumin alone.

Thus, covalent linkage of a TLR7 agonist to a tumor antigen stimulated DC cytokine production and protected mice from tumor challenge. The use of a suitable TLR7 agonist which retains its immune stimulating properties under physiologic conditions following coupling to a macromolecule, such as an antigen, may be useful in the development of an in situ vaccine in solid tumor therapy.

Various purines, pyridines, and imidazoquinolines, with molecular weights of 200-400 kD, have been shown to activate TLR7 and compounds that were specific TLR7 ligands were 100-1000 fold more powerful than imiquimod on a molar basis (Lee et al., infra). Because these TLR agonists are structurally very similar to normal component of nucleotides, they are very unlikely to induce a haptenic immune reaction after repeated administration.

Figure 3A:
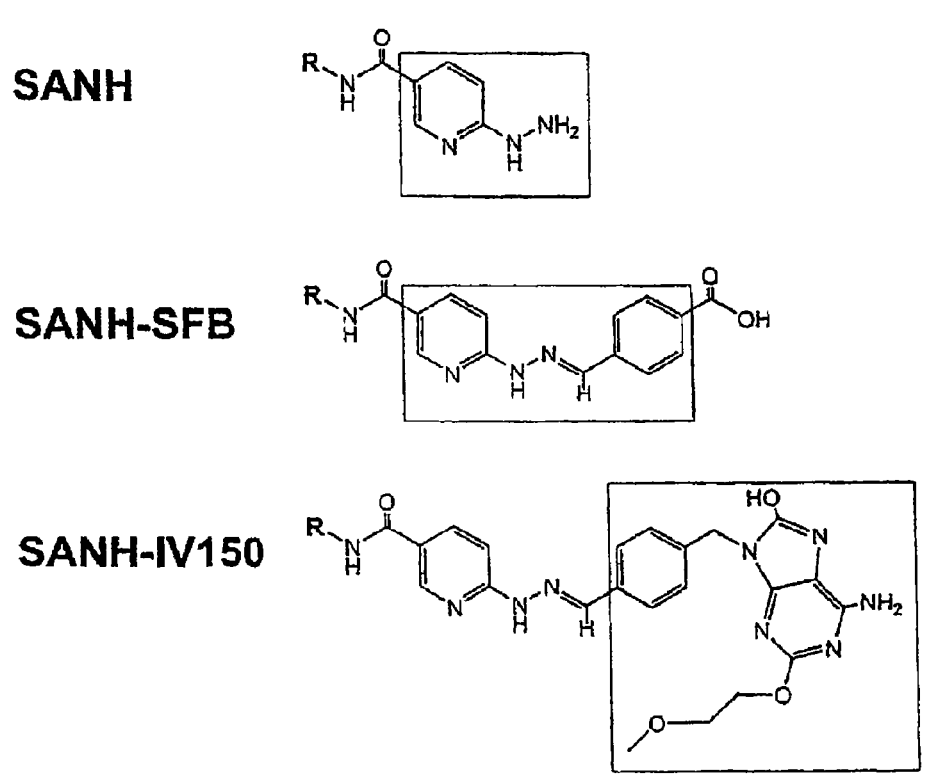
FIG. 3A illustrates a linker (SANH) for conjugating a macromolecule and a synthetic TLR agonist.
Figure 3B:
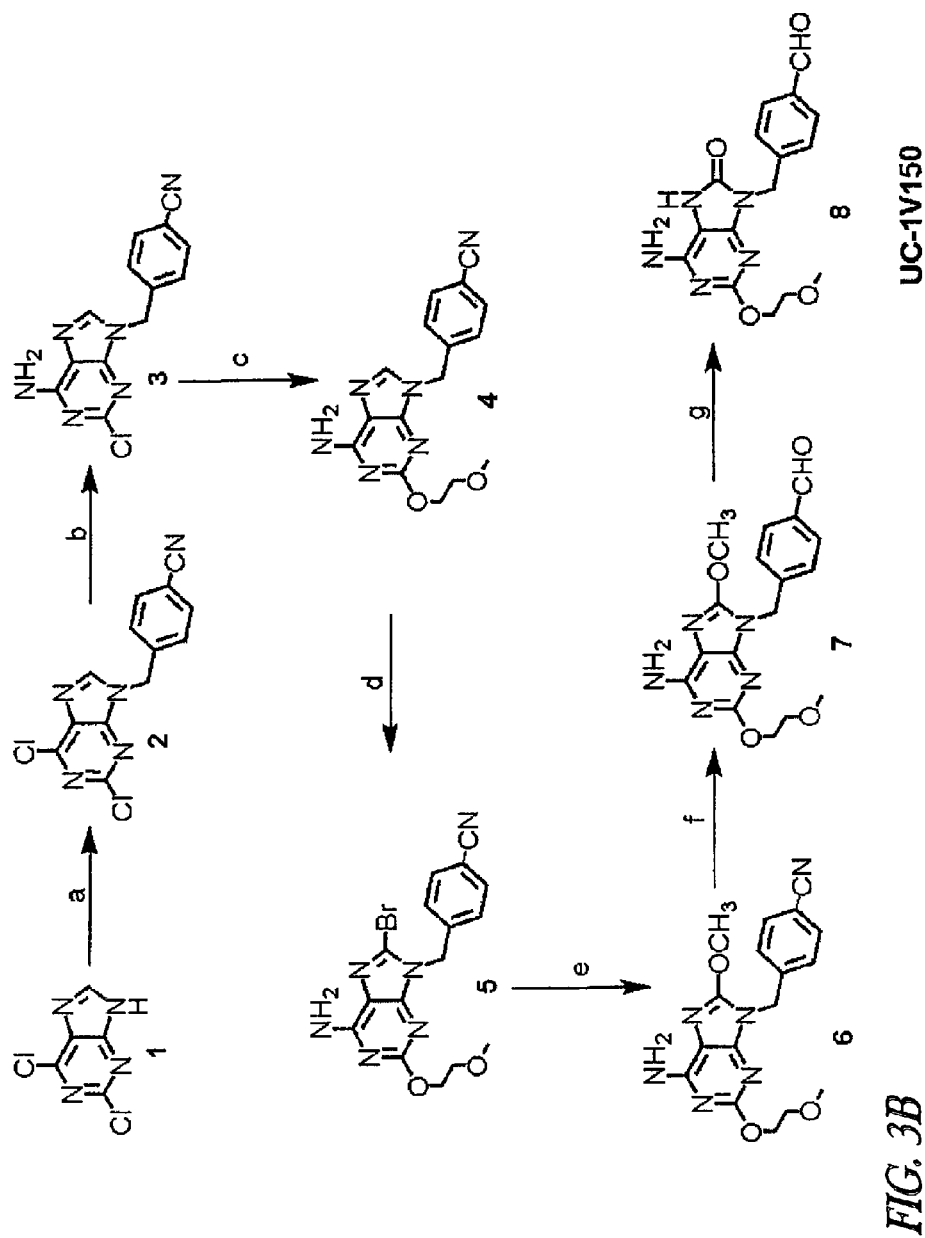
FIG. 3B illustrates synthesis of UC-1V150.
Figure 3C:
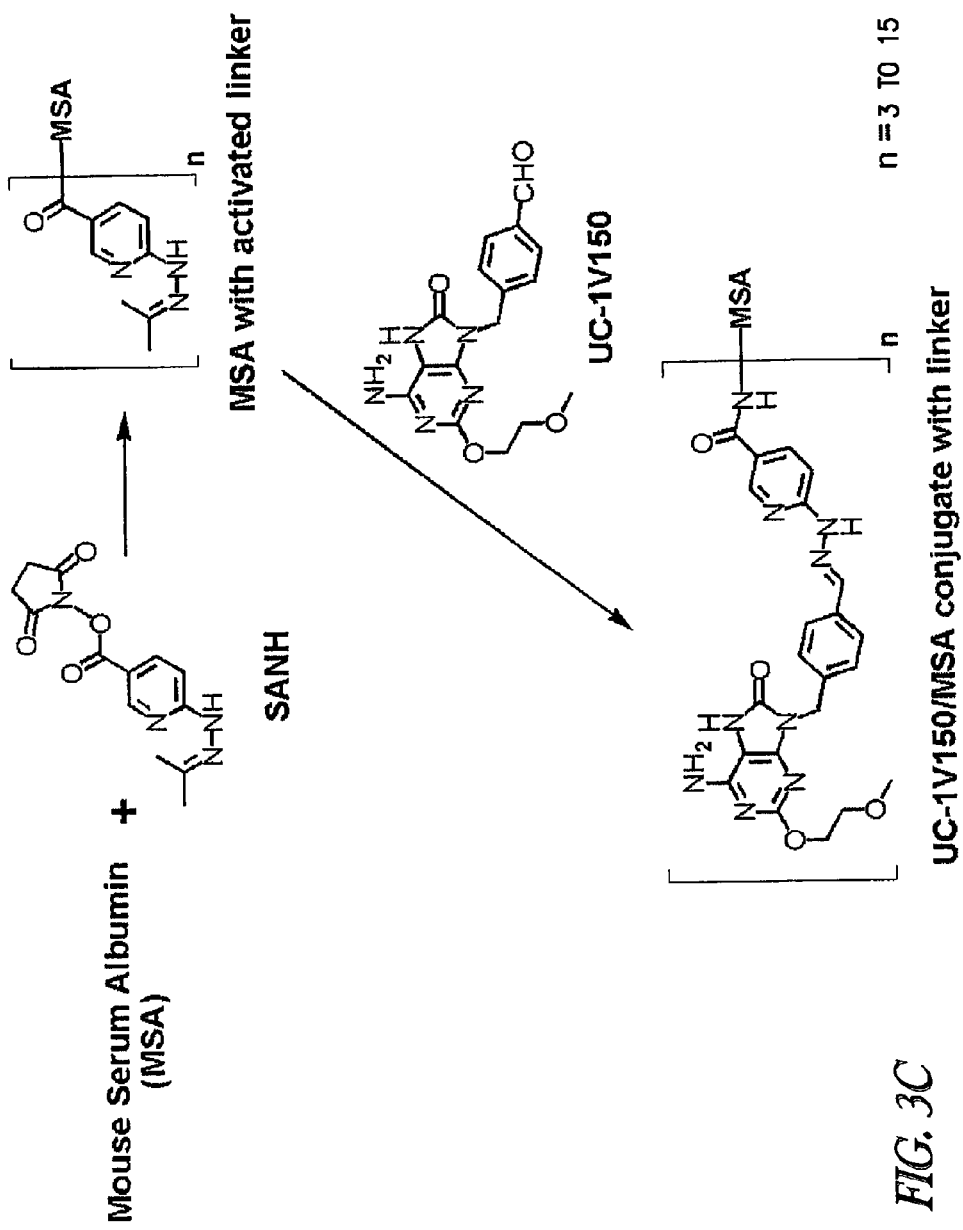
FIG. 3C illustrates conjugation of UC-1V150 to MSA. 200 μL of MSA (25 mg/mL) is mixed with 100 μL of conjugation buffer (1M phosphate, pH=7.2) and 690 μL of PBS. 844 μg of SANH in 10 μL of DMF (40-fold molar excess to MSA) is added to protein solution (Final concentration of NP in reaction mixture is 5 mg/mL). After gentle mixing, reaction is allowed to proceed at room temperature for 2 hours. To remove excess of SANH the reaction mixture is loaded on a microcon spin filter device (YM-3, Millipore) and concentrated to about 70 μL. 460 μg of UC-1V150 dissolved in 10 μL of DMF was added to MSA modified with SANH and the reaction mixture was incubated at RT overnight. To remove excess UC-1V150 the reaction mixture was first concentrated to 50 μL using a microcon spin filter device (Millipore: YM-3) and loaded on a G25 micro-spin column (GE Healthcare).
Figure 4:
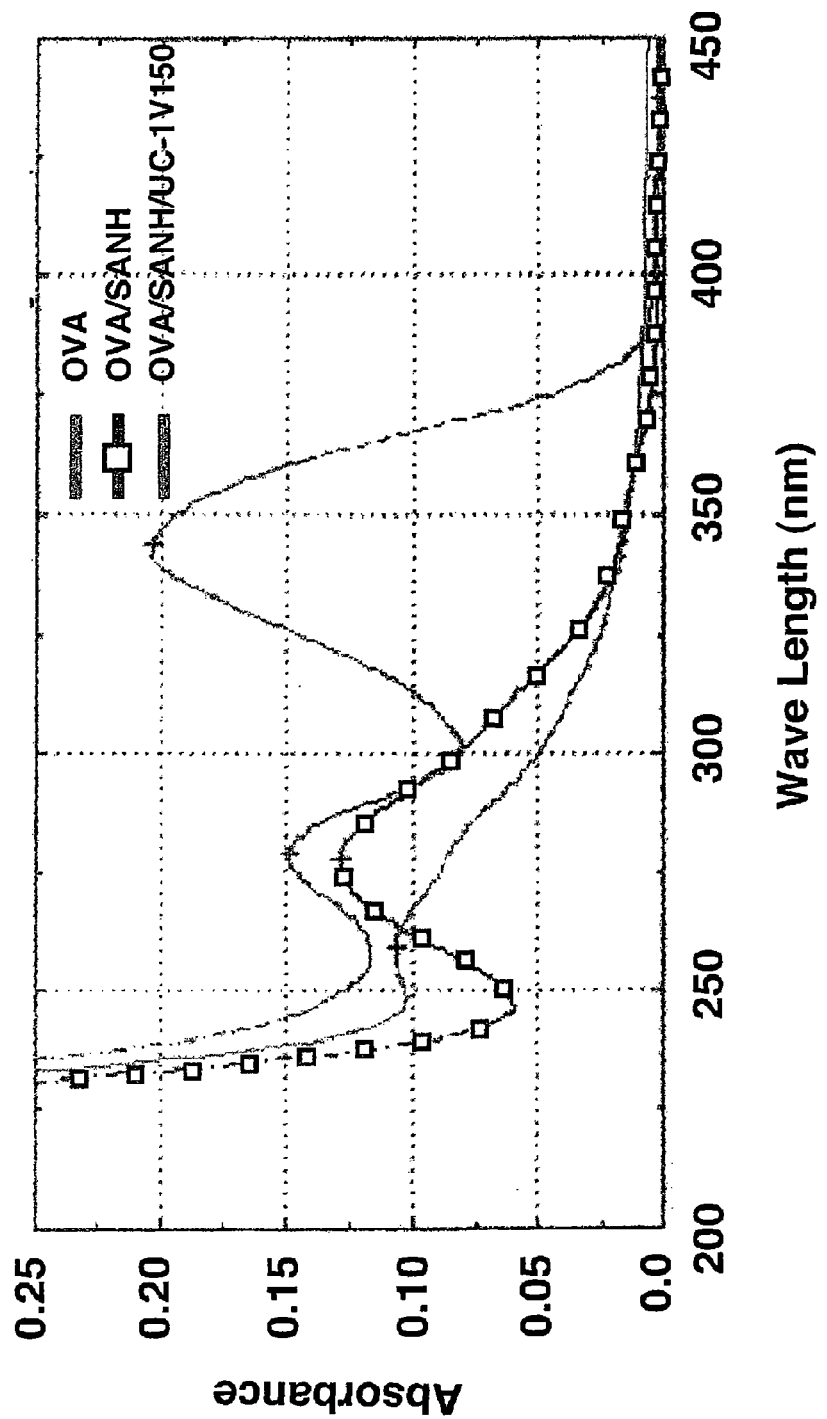
FIG. 4 is a graphic illustration of the absorption profile (at about 350 nm) of a compound of formula I (an OVA/SANH/UC-1V150 conjugate).
Figure 5:
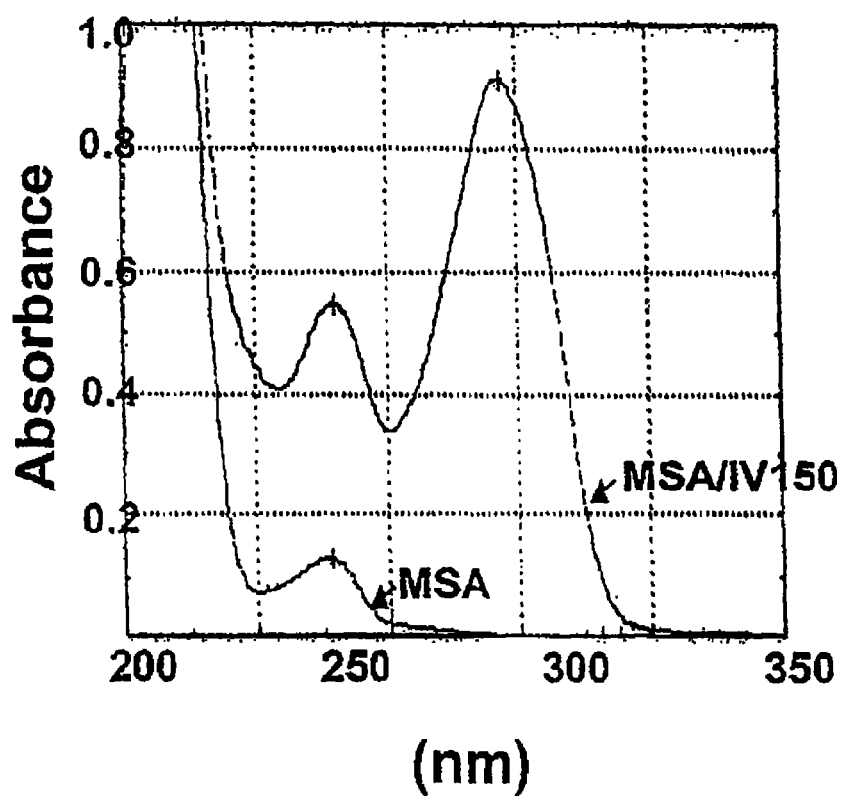
FIG. 5 illustrates the absorbance profile of a conjugation reaction of a synthetic TLR7 agonist, UC-1V150, to mouse serum albumin (MSA). The UC-1V150 to MSA ratio is approximately 5:1.

An adenine based TLR7 pharmacore may need to be covalently tied to an "auxiliary group" (macromolecule) to promote uptake into the endosomes of dendritic cells, where TLR7 is expressed, and to retain the TLR agonist. Accordingly, the TLR7 agonist UC-1V150 was prepared and coupled via its aldehyde function and a linker to free amino groups on various proteins, including mouse albumin (MSA) (FIG. 3). The conjugates were 100-fold more potent in vitro and in vivo than the uncoupled adenine analog. Moreover, intrapulmonary administration of the albumin conjugate (UC-1V150/MSA) to mice induced local cytokine production in the bronchial alveolar lavage fluid (BALF) without systemic cytokine release. In marked contrast, the delivery of the untethered drug to the airways quickly triggered cytokine release in the bloodstream.

Figure 6:
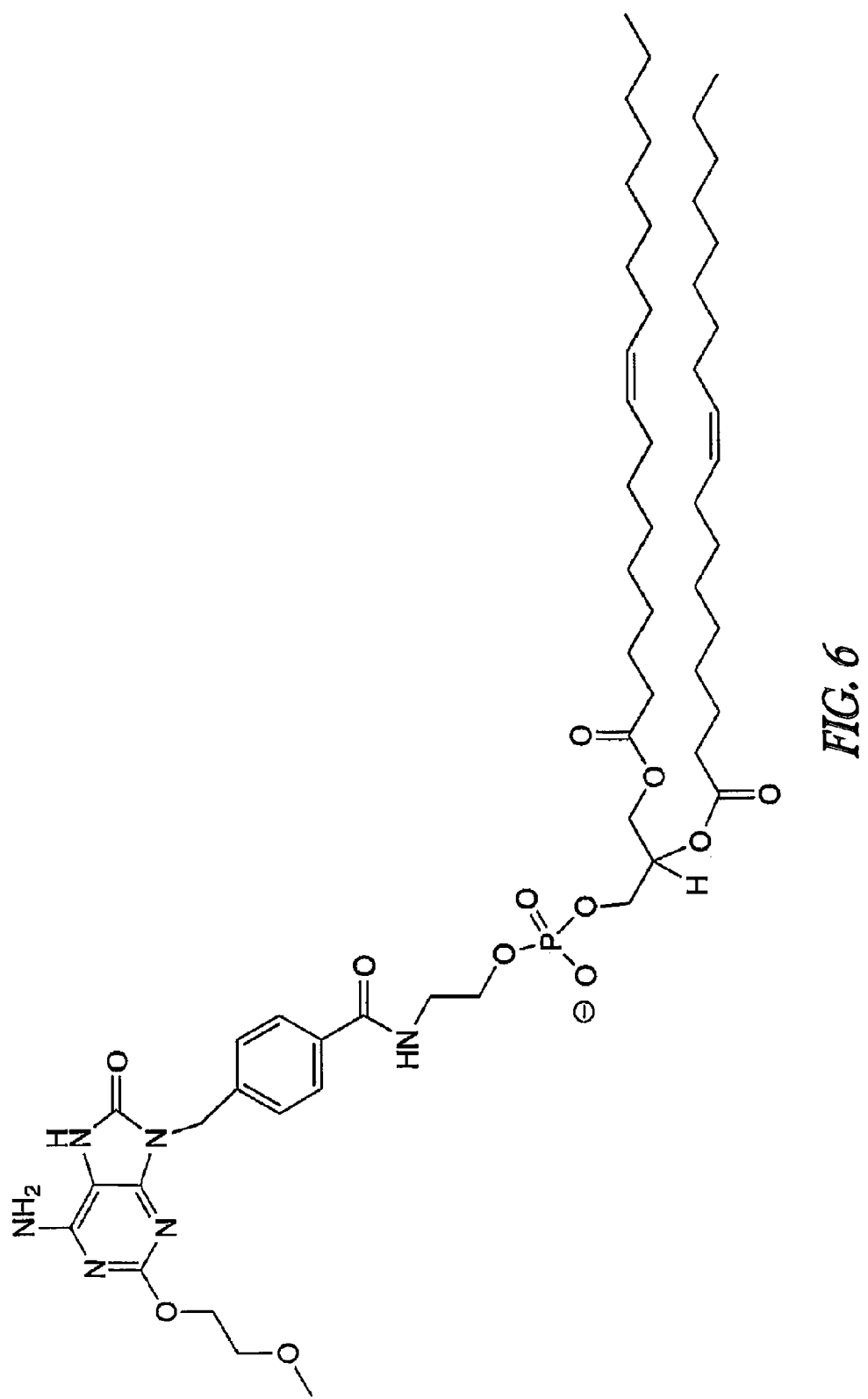
FIG. 6 illustrates a TLR agonist/phospholipid conjugate.
Figure 7:
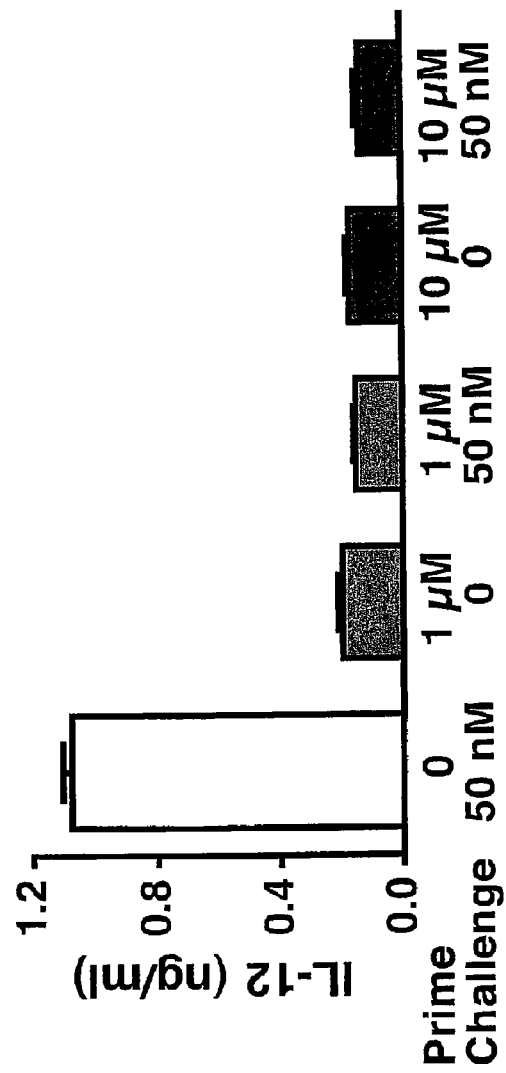
FIG. 7 shows the effect of UC-1V199/lipid administration at different doses and timing.
Figure 8A:
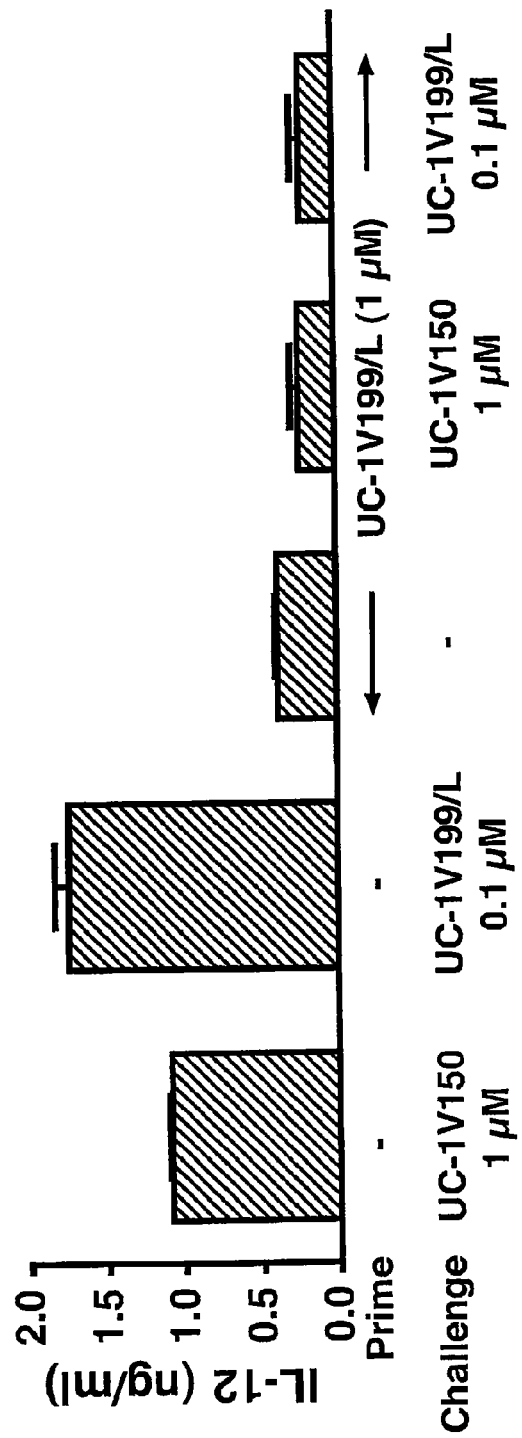
FIGS. 8A-B show that UC-1V199/lipid inhibits TLR7 and TLR2 signaling.
Figure 8B:
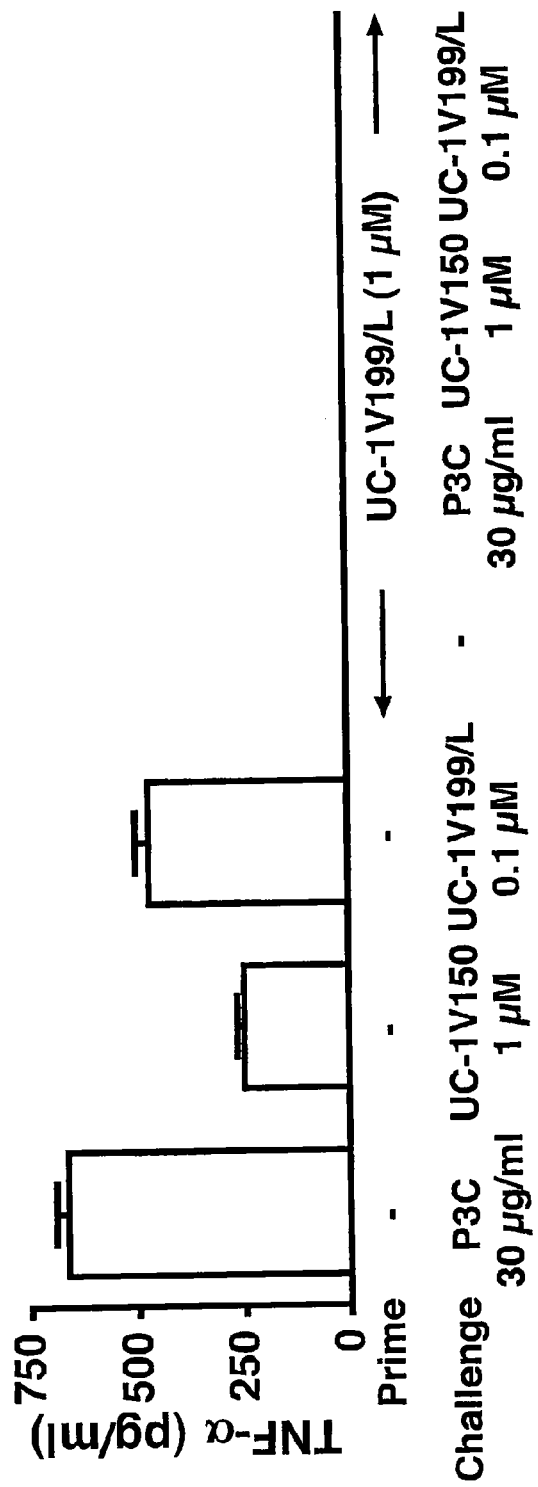

In one embodiment, a TLR7 agonist maximizes the production of Th1 stimulating cytokines (interferons and IL-12) compared to TNFα and IL-1. TLR7 is localized on the inner surfaces of the endosomal vesicles that are constantly synthesized and undergo maturation in DC. For example, to prevent asthma, a stable and potent TLR agonist that traffics to the early endosomes of dendritic cells and induces primarily Type I interferons is preferred. A TLR agonist was covalently attached to a phospholipid auxiliary group with the expectation that the conjugate, UC-1V199/L (FIG. 6), would quickly and stably insert into lipid membranes of cells, including endosomal vesicles. Remarkably, as little as 30 picomolar UC-1V199/L induced cytokine synthesis in bone marrow derived mouse mononuclear cells. FIGS. 7-8 show data for IL-12 synthesis.

Figure 9:
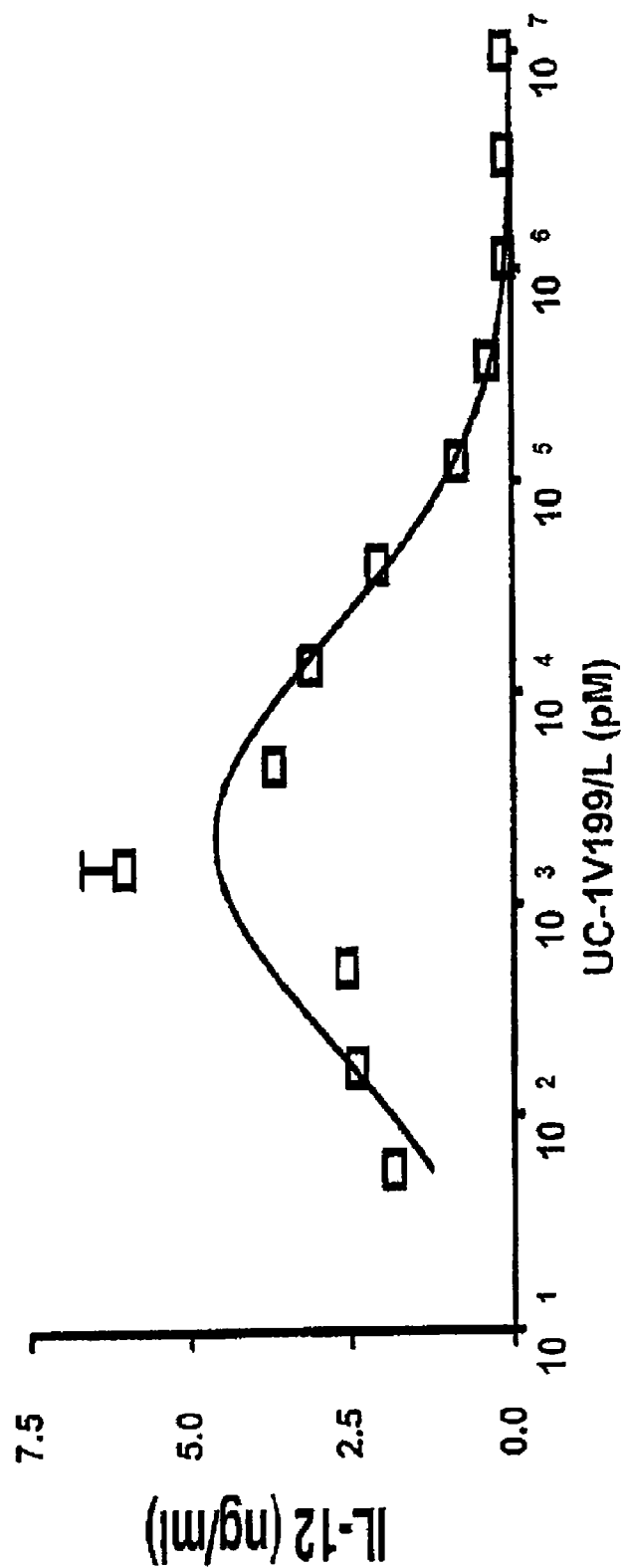
FIG. 9 illustrates biphasic dose-response to an ultrapotent TLR7 agonist (a pico/nanomolar agonist and micromolecular antagonist).

The TLR7 ligands that are purines or imidazoquilolines have a peculiar property, i.e., a biphasic dose response curve. At high concentrations, the drug fails to induce cytokine synthesis. The biphasic effect is observed in highly purified dendritic cells, and appears to be cell autonomous. However, the remarkable potency of UC-1V199/L enabled re-examination of the phenomenon, using pharmacologically acceptable drug concentrations (FIG. 9). Maximal cytokine production was observed with 10 nM UC-1V199/L while higher concentrations induced progressively less IL-12 (and TNF) release.

High and sustained concentrations of TLR7 agonists are known to induce refractoriness to TLR re-stimulation that can last 24 hours or more. Such a complex system of regulation is apparently part of a fail-safe mechanism that prevents cells and tissues from self-destruction during inflammatory responses. Thus, it was of interest to determine if concentrations of UC-1V199/L that failed to induce significant cytokine synthesis could nonetheless induce "TLR tolerance." Indeed, when bone marrow derived mononuclear cells were exposed to a non-activating concentration UC-1V199/L (1 µM), and then re-stimulated 24 hours later with the same compound, with UC-1V150 or with pam3Cys (P3C, a TLR2 activator), they displayed a markedly diminished cytokine response. In contrast, the UC-1V199/L treated cells retained responsiveness to ligands of TLR3 and TLR4, which go through the TRIF pathway (results not shown). Preliminary experiments indicated that non-responsiveness was also induced in vivo. Thus, daily administration of UC-1V199/L, and related drugs, may suppress inflammation induced by MyD88-dependent stimuli, without the systemic side effects associated with TLR activation.

In one embodiment, the conjugates of the invention may be useful for preventing, inhibiting or treating asthma. Asthma is characterized by episodes of intermittent reversible airway constriction, bronchial smooth muscle hyperplasia and chronic inflammation. Atopic disease predisposes to asthma but up to half of the affected patients are not atopic. Other environmental risk factors for asthma include tobacco smoke and air pollutants. Moreover, disease flares in affected asthmatic patients may be triggered not only by allergens but also by airway irritants, temperature changes and infections.

The initial development of an allergic response is partly regulated by a balance between Th1 and Th2 lymphocytes, and their respective cytokines, especially the interferons and IL-4. Vaccination of animals with an allergen in conjunction with a TLR7 or TLR9 agonist preferentially expands allergen-specific Th1 memory cells. Consequently, subsequent immunization with antigen in conjunction with a Th2 biased adjuvant does not readily elicit an IgE response. Mice that were vaccinated with antigen and TLR7 or TLR9 agonists were resistant to experimental asthma.

A different approach is needed for the treatment of asthma with TLR agonists versus the prevention of asthma. In affected patients, the airways and pulmonary tissues are already infiltrated with a diverse population of inflammatory cells, including many subsets of lymphocytes, macrophages, dendritic cells, mast cells, eosinophils, and neutrophils. In this situation, TLR agonists can potentially exacerbate disease, by augmenting the release of inflammatory mediators such as TNF-alpha and IL-1. Indeed, the ability of various microbial agents to activate TLRs may explain why they trigger asthmatic attacks.

A TLR agonist for the prevention of asthma preferably is confined to the lungs but also maximizes the production of Th1 stimulating cytokines (interferons and IL-12), compared to TNF-alpha and IL-1. Both TLR7 and TLR9 are localized on the inner surfaces of the endosomal vesicles that are constantly synthesized and undergo maturation in dendritic cells. TLR9 activating oligonucleotides that are aggregated phosphodiester oligonucleotides stay longer in early endosomal vesicles and therefore induce more type I interferons than nonaggregated phosphorothioate oligonucleotides, which go to mature vesicles. The results imply that the spatial organization of the TLR agonist governs its trafficking and its pattern of induced cytokine synthesis. To prevent asthma, a stable, potent and molecularly characterized TLR agonist that trafficks to the early endosomes of dendritic cells and induces primarily Type I interferons is preferred.

To study the effect of conjugates of the invention on allergic asthma, airway inflammation is induced by sensitizing mice via subcutaneaous injection of 20 µg of ovalbumin absorbed with 500 µg alum per mouse in saline on day 0 and day 7. On days 16 and 21, mice are challenged i.n. with 5 µg ovalbumin per mouse. Conjugates are administered i.n., p.o. or i.v. at different time points prior to the first ovalbumin challenge on day 16. Twenty-four hours after the last challenge (day 22), airway responsiveness is measured, mice are sacrificed and BALF cells, lung and spleen samples collected. Naïve mice and ovalbumin/alum-sensitized mice serve as controls. The total number of cells in BALF are counted and stained with Wright-Giemsa to determine numbers of eosinophils, lymphocytes, neutrohils and last cells. Cytokine levels in the BALF are determined by Luminex assays. Airway responsiveness to methacholine is assessed 24 hours after the last challenge using a single chamber, whole body plethysmograph. The Penh, a dimensionless value that correlates well with pulmonary resistance measured by conventional two chamber plethysmography in ventilated mice, is used to monitor airway responsiveness.

The compounds of this invention are administered in a therapeutically effective amount to a subject in need of treatment. Administration of the compositions of the invention can be via any of suitable route of administration, particularly parenterally, for example, intravenously, intra-arterially, intraperitoneally, intrathecally, intraventricularly, intraurethrally, intrasternally, intracranially, intramuscularly, or subcutaneously. Such administration may be as a single bolus injection, multiple injections, or as a short- or long-duration infusion. Implantable devices (e.g., implantable infusion pumps) may also be employed for the periodic parenteral delivery over time of equivalent or varying dosages of the particular formulation. For such parenteral administration, the compounds are preferably formulated as a sterile solution in water or another suitable solvent or mixture of solvents. The solution may contain other substances such as salts, sugars (particularly glucose or mannitol), to make the solution isotonic with blood, buffering agents such as acetic, critric, and/or phosphoric acids and their sodium salts, and preservatives.

The compounds of the invention can be formulated as pharmaceutical compositions and administered to a mammalian host, such as a human patient in a variety of forms adapted to the chosen route of administration, i.e., orally or parenterally, by intravenous, intramuscular, topical or subcutaneous routes.

Thus, the present compounds may be systemically administered, e.g., orally, in combination with a pharmaceutically acceptable vehicle such as an inert diluent or an assimilable edible carrier. They may be enclosed in hard or soft shell gelatin capsules, may be compressed into tablets, or may be incorporated directly with the food of the patient's diet. For oral therapeutic administration, the active compound may be combined with one or more excipients and used in the form of ingestible tablets, buccal tablets, troches, capsules, elixirs, suspensions, syrups, wafers, and the like. Such compositions and preparations should contain at least 0.1% of active compound. The percentage of the compositions and preparations may, of course, be varied and may conveniently be between about 2 to about 60% of the weight of a given unit dosage form. The amount of active compound in such therapeutically useful compositions is such that an effective dosage level will be obtained.

The tablets, troches, pills, capsules, and the like may also contain the following: binders such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, fructose, lactose or aspartame or a flavoring agent such as peppermint, oil of wintergreen, or cherry flavoring may be added. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac or sugar and the like. A syrup or elixir may contain the active compound, sucrose or fructose as a sweetening agent, methyl and propylparabens as preservatives, a dye and flavoring such as cherry or orange flavor. Of course, any material used in preparing any unit dosage form should be pharmaceutically acceptable and substantially non-toxic in the amounts employed. In addition, the active compound may be incorporated into sustained-release preparations and devices.

The active compound may also be administered intravenously or intraperitoneally by infusion or injection. Solutions of the active compound or its salts can be prepared in water, optionally mixed with a nontoxic surfactant. Dispersions can also be prepared in glycerol, liquid polyethylene glycols, triacetin, and mixtures thereof and in oils. Under ordinary conditions of storage and use, these preparations contain a preservative to prevent the growth of microorganisms.

The pharmaceutical dosage forms suitable for injection or infusion can include sterile aqueous solutions or dispersions or sterile powders comprising the active ingredient which are adapted for the extemporaneous preparation of sterile injectable or infusible solutions or dispersions, optionally encapsulated in liposomes. In all cases, the ultimate dosage form should be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions or by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars, buffers or sodium chloride. Prolonged absorption of the injectable compositions can be brought about by the use in the compositions of agents delaying absorption, for example, aluminum monostearate and gelatin.

Sterile injectable solutions are prepared by incorporating the active compound in the required amount in the appropriate solvent with various of the other ingredients enumerated above, as required, followed by filter sterilization. In the case of sterile powders for the preparation of sterile injectable solutions, the preferred methods of preparation are vacuum drying and the freeze drying techniques, which yield a powder of the active ingredient plus any additional desired ingredient present in the previously sterile-filtered solutions.

For topical administration, the present compounds may be applied in pure form, i.e., when they are liquids. However, it will generally be desirable to administer them to the skin as compositions or formulations, in combination with a dermatologically acceptable carrier, which may be a solid or a liquid.

Useful solid carriers include finely divided solids such as talc, clay, microcrystalline cellulose, silica, alumina and the like. Useful liquid carriers include water, alcohols or glycols or water-alcohol/glycol blends, in which the present compounds can be dissolved or dispersed at effective levels, optionally with the aid of non-toxic surfactants. Adjuvants such as fragrances and additional antimicrobial agents can be added to optimize the properties for a given use. The resultant liquid compositions can be applied from absorbent pads, used to impregnate bandages and other dressings, or sprayed onto the affected area using pump-type or aerosol sprayers.

Thickeners such as synthetic polymers, fatty acids, fatty acid salts and esters, fatty alcohols, modified celluloses or modified mineral materials can also be employed with liquid carriers to form spreadable pastes, gels, ointments, soaps, and the like, for application directly to the skin of the user.

In addition, in one embodiment, the invention provides various dosage formulations of the conjugates for inhalation delivery. For example, formulations may be designed for aerosol use in devices such as metered-dose inhalers, dry powder inhalers and nebulizers.

Examples of useful dermatological compositions which can be used to deliver the compounds of the invention to the skin are known to the art; for example, see Jacquet et al. (U.S. Pat. No. 4,608,392), Geria (U.S. Pat. No. 4,992,478), Smith et al. (U.S. Pat. No. 4,559,157) and Wortzman (U.S. Pat. No. 4,820,508).

Useful dosages of the compounds of the invention can be determined by comparing their in vitro activity, and in vivo activity in animal models. Methods for the extrapolation of effective dosages in mice, and other animals, to humans are known to the art; for example, see U.S. Pat. No. 4,938,949. The ability of a compound of the invention to act as a TLR agonist may be determined using pharmacological models which are well known to the art, including the procedures disclosed by Lee et al., *Proc. Natl. Acad. Sci. USA*, 100: 6646 (2003).

Generally, the concentration of the compound(s) of the invention in a liquid composition, such as a lotion, will be from about 0.1-25 wt-%, preferably from about 0.5-10 wt-%. The concentration in a semi-solid or solid composition such as a gel or a powder will be about 0.1-5 wt-%, preferably about 0.5-2.5 wt-%.

The active ingredient may be administered to achieve peak plasma concentrations of the active compound of from about 0.5 to about 75 µM, preferably, about 1 to 50 µM, most preferably, about 2 to about 30 µM. This may be achieved, for example, by the intravenous injection of a 0.05 to 5% solution of the active ingredient, optionally in saline, or orally administered as a bolus containing about 1-100 mg of the active ingredient. Desirable blood levels may be maintained by continuous infusion to provide about 0.01-5.0 mg/kg/hr or by intermittent infusions containing about 0.4-15 mg/kg of the active ingredient(s).

The amount of the compound, or an active salt or derivative thereof, required for use in treatment will vary not only with the particular salt selected but also with the route of administration, the nature of the condition being treated and the age and condition of the patient and will be ultimately at the discretion of the attendant physician or clinician. In general, however, a suitable dose will be in the range of from about 0.5 to about 100 mg/kg, e.g., from about 10 to about 75 mg/kg of body weight per day, such as 3 to about 50 mg per kilogram body weight of the recipient per day, preferably in the range of 6 to 90 mg/kg/day, most preferably in the range of 15 to 60 mg/kg/day.

The compound is conveniently administered in unit dosage form; for example, containing 5 to 1000 mg, conveniently 10 to 750 mg, most conveniently, 50 to 500 mg of active ingredient per unit dosage form.

The desired dose may conveniently be presented in a single dose or as divided doses administered at appropriate intervals, for example, as two, three, four or more sub-doses per day. The sub-dose itself may be further divided, e.g., into a number of discrete loosely spaced administrations; such as multiple inhalations from an insufflator or by application of a plurality of drops into the eye. The dose, and perhaps the dose frequency, will also vary according to the age, body weight, condition, and response of the individual patient. In general, the total daily dose range for a compound or compounds of formula (I), for the conditions described herein, may be from about 50 mg to about 5000 mg, in single or divided doses. Preferably, a daily dose range should be about 100 mg to about 4000 mg, most preferably about 1000-3000 mg, in single or divided doses, e.g., 750 mg every 6 hr of orally administered compound. This can achieve plasma levels of about 500-750 uM, which can be effective to kill cancer cells. In managing the patient, the therapy should be initiated at a lower dose and increased depending on the patient's global response.

As described above, compositions that contain a compound of the invention, are useful in the treatment or prevention of a disease or disorder in, for example, humans or other mammals (e.g., bovine, canine, equine, feline, ovine, and porcine animals), and perhaps other animals as well. Depending on the particular compound, the composition will, for example, be useful for treating cancer, an infection, enhancing adaptive immunity (e.g., antibody production, T cell activation, etc.), as vaccines, and/or stimulating the central nervous system.

The invention will be further described by the following non-limiting examples.

Example 1

Processes for preparing compounds of formula (I) are provided as further embodiments of the invention and are illustrated by the following procedures in which the meanings of the generic radicals are as given above unless otherwise qualified.

General Chemistry.

Reagents and solvents were acquired from Aldrich, Milwaukee, Wis. Uncorrected melting points were determined on a Laboratory Device Mel-Temp II capillary melting point apparatus. Proton nuclear magnetic resonance spectra were recorded on a Varian Unity 500 NMR spectrophotometer at 499.8 MHz or on a Varian Mercury NMR spectrophotometer at 400.06 MHz. The chemical shifts were reported in ppm on the scale from the indicated reference. Positive and negative ion loop mass spectra were performed by Department of Chemistry UCSD, San Diego, Calif. Elemental analyses were performed by NuMega Resonance Labs, San Diego, Calif. Column chromatography was conducted on E Merck silica gel (230-400 mesh) with the indicated solvent system. Analytical thin layer chromatography (TLC) was conducted on silica gel 60 F-254 plates (EM Reagents).

Preparation of
4-(2,6-dichloropurin-9-ylmethyl)benzonitrile 2,6-dichloro-9H-purine (16 mmol) is dissolved in DMF (50 mL) and potassium carbonate (50 mmol) is added. α-Bromo-p-tolunitrile (22 mmol) is then added and the mixture is stirred at ambient temperature for 16 hours. After filtration to remove insoluble inorganic salts, the filtrate is poured into water (1500 mL) and extracted with ethyl acetate (2×400 mL), dried over magnesium sulfate and evaporated to yield a residue which is subjected to flash silica gel chromatography using 1:2:10 ethyl acetate/acetone/hexanes. Yield 3.33 g (69%). UV, NMR and MS were consistent with structure assignment.

Preparation of
4-(6-amino-2-chloropurin-9-ylmethylbenzonitrile

The product above (1.9 g) is placed in a steel reaction vessel and methanolic ammonia (80 mL, 7 N) is added. The sealed vessel is heated at 60° C. for 12 hours, cooled in ice and the solid product filtered off. Yield 1.09 g. UV, NMR and MS were consistent with assigned structure.

Preparation of 4-[6-amino-2-(2-methoxyethoxy)purin-9-ylmethyl]benzonitrile

Sodium salt of 2-methoxyethanol is generated by dissolving sodium metal (81 mg) in 2-methoxyethanol (30 mL) with heat. To this solution is added the product of example 2 (1.0 g) dissolved in methoxyethanol (300 mL, with heat). The reaction mixture is heated for 8 hours at 115° C. bath temperature, concentrated in vacuo to near dryness and the residue partitioned between ethyl acetate and water. Flash silica gel chromatography of the organic layer using 5% methanol in dichloromethane gave 763 mg product. NMR is consistent with structure assignment.

Preparation of 4-[6-amino-8-bromo-2-(2-methoxyethoxy)purin-9-ylmethyl]benzonitrile The product immediately above (700 mg) is dissolved in dichloromethane (400 mL) and bromine (7 mL) is added dropwise. The mixture is stirred overnight at room temperature and extracted with aqueous sodium thiosulfate (2 L of 0.1 M) solution and then with aqueous sodium bicarbonate (500 mL, saturated). The residue from the organic layer is chromatographed on silica gel using 3% methanol in dichloromethane) to yield 460 mg of bromo product. NMR, UV and MS are consistent with structure assignment.

Preparation of 4-[6-amino-8-methoxy-2-(2-methoxyethoxy)purin-9-ylmethyl]benzonitrile Sodium methoxide is generated by reaction of sodium metal (81 mg) in dry methanol (30 mL). The product immediately above (700 mg) is dissolved in dry dimethoxyethane and the temperature raised to 100° C. After overnight reaction, the mixture is concentrated in vacuo and the residue is chromatographed on silica using 5% methanol in dichloromethane. Yield 120 mg. NMR is consistent with structure assignment.

Preparation of Lithium
N,N'-(dimethylethylenediamino)aluminum hydride

This reducing agent used to convert the nitrile to the aldehyde function is prepared essentially as described in *Bull. Korean Chem. Soc.*, 23:1697 (2002). A 0.5 M solution in dry THF is prepared.

Preparation of 4-[6-amino-8-methoxy-2-(2-methoxyethoxy)purin-9-ylmethyl]benzaldehyde 4-[6-amino-8-methoxy-2-(2-methoxyethoxy)purin-9-ylmethyl]benzonitrile (100 mg) is dissolved in dry THF (3 mL) and cooled to 0° C. under argon. The aluminum hydride reagent generated above (0.72 mL) is added to the reaction flask and the mixture is stirred at 0-5° C. for 1 hour and then quenched by addition of 3 M HCl. The mixture is then extracted with ethyl acetate and then dichloromethane and concentrated in vacuo to yield 85 mg. NMR is consistent with structure assignment.

Preparation of 4-[6-amino-8-hydroxy-2-(2-methoxyethoxy)purin-9-ylmethyl]benzaldehyde (UC-1V150)

The product immediately above (800 mg) is combined with sodium iodide (504 mg) and acetonitrile (40 mL), and then chlorotrimethylsilane (0.5 mL) is slowly added. The mixture is heated at 70° C. for 3.5 hours, cooled and filtered. The solid product is washed with water, then ether to yield 406 mg. NMR, UV, MS are consistent with structure assignment. This material is suitable for conjugation reactions between linkers and macromolecules.

Preparation of methyl 4-[6-amino-8-methoxy-2-(2-methoxyethoxy)purin-9-ylmethyl]benzoate The procedure is as described by Jayachitra, et al., *Synth. Comm.*, 33:3461 (2003)). 4-[6-amino-8-methoxy-2-(2-methoxyethoxy)purin-9-ylmethyl]benzonitrile (1 mmol) is dissolved in dry methanol (5 mL) and freshly distilled $BF_3$ etherate (4 mmol) is added to the solution. The resulting mixture is refluxed under argon for 20 hours. The solvent is removed in vacuo and the residue is taken up in dichloromethane (10 mL) and extracted with dilute aqueous sodium bicarbonate (2×10 mL) and the organic layer is dried over magnesium sulfate. After evaporation the product is purified by silica gel column chromatography using 5% methanol in dichloromethane to yield 0.8 mmol.

Preparation of 4-[6-amino-8-hydroxy-2-(2-methoxyethoxy)purin-9-ylmethyl]benzoic acid 4-[6-amino-8-methoxy-2-(2-methoxyethoxy)purin-9-ylmethyl]benzoate (100 mg) is combined with sodium iodide (63 mg) and acetonitrile (10 mL), and then chlorotrimethylsilane (120 mL) is slowly added. The mixture is heated at 70° C. for 6 hours, cooled and filtered. The solid product is washed with water, then ether to yield 51 mg.

Preparation of 2,5-dioxopyrrolidin-1-yl 4-[6-amino-8-hydroxy-2-(2-methoxyethoxy)purin-9-ylmethyl]benzoate 4-[6-amino-8-methoxy-2-(2-methoxyethoxy)purin-9-ylmethyl]benzoate (2 mmol) is dissolved in dichloromethane or dioxane (10 mL) and EDC (2 mmol) is added. To this solution is added N-hydroxysuccinimide (2 mmol) and resulting mixture is stirred at room temperature for 1 hour. The mixture is taken to dryness in vacuo and the crude product is purified by silica gel chromatography to yield 2 mmol of product that is suitable for conjugation reactions involving primary amines.

Example II

UC-1V150 was covalently coupled to MSA first modified with a succinimidyl 6-hydrazino-nicotinamide acetone hydrazone (SANH) linker to yield a stable molecule with a characteristically altered UV spectrum. The UC-1V150/MSA conjugate was identified by a UV absorption peak at 342 nm due to hydrazone formation, whereas SANH alone absorbed at 322 nm. Quantification of UC-1V150 molecules conjugated per MSA was extrapolated from a standard curve of UC-1V150-SANH (FIG. 1). Consistently the UC-1V150/MSA conjugates were obtained at a ratio of about 5:1. The biological studies reported here were done by using 5:1 UC-1V150/MSA.

Modification of MSA with SANH.

200 μL of MSA (25 mg/mL) was mixed with 100 μL of conjugation buffer (1M NaPi, pH=7.2) and 690 μl of PBS. 844 μg of SANH in 10 μL of DFM (40-fold molar excess to MSA) was added to protein solution (final concentration of MSA in reaction mixture is 5 mg/mL). After gentle mixing reaction was proceeded at room temperature for 2 hours. To remove excess of SANH the reaction mixture was loaded on NAP-10 column equilibrated with PBS and modified MSA was eluted with 1.5 mL of PBS.

Attachment of IV 150 to MSA Modified with SANH.

460 μg of IV 150 dissolved in 10 μL of DMF was added to MSA modified with SANH and the reaction mixture was incubated at RT overnight. To remove excess of IV 150 the reaction mixture was firstly concentrated to 1 mL using micro-spin column (Millipore: BIOMAX 5K) and loaded on NAP-10 column as mentioned above.

TLR7 agonists were also conjugated to oligodeoxynucleotides (ODNs) (FIGS. 20-21), a virus (FIGS. 18-19), and to a lipid component which can then be incorporated into a liposome (FIGS. 24-25).

Synthesis of Spatially Regulated TLR7 Agonist.

Each conjugate is prepared by standard techniques well known in bioconjugation chemistry. Characterization of each by quantitative UV, LC/MS, and PAGE methods determines the "valence" or ratio of TLR agonist to its auxiliary group (macromolecule). From this information, the size and shape of the conjugates are easily estimated by modeling techniques. The diversity in size, shape, and valence of the conjugates is introduced through the selection of the macromolecule, represented in the structure scheme as R3. For example, when R3 is a dendrimer, such as of the common poly(amidoamine) variety, the number of surface functional groups for attachment of the TLR agonist is precisely defined based on the number of branching points or generations of that particular dendrimer. A first generation (G1) has 8 surface amino groups, a G2 has 16, and so on, thus resulting in a high level of control over valence and size of the conjugates (see FIG. 2). Additionally, some dendrimer nanoparticles may contain both a targeting ligand and the TLR7 agonist. The TLR7 agonist-lipid conjugates may also have a variety of "valences" depending on the selection of the lipids. For example, the potent conjugate UV-1V199/L (FIG. 6) was prepared by coupling a carboxy derivative of the TLR7 agonist (UC-1V199) to the ethanolamino group of the commercially available dioleanylphosphatidylethanolamine (DOPE).

These lipid conjugates are formulated into various liposome nanoparticles by combining with cholesterol, DOPE, and other lipids to produce particles having a hydrodynamic diameter of about 100 nm (FIGS. 24-25). The hexagons in the figure represent UC-1V199/L and related TLR7 agonist with phospholipid tails.

TLR7 agonists and dimers, as well as TLR conjugates have been shown to have cytokine releasing and/or cytokine activity in vivo as determined by assays such as those disclosed herein. For instance, imiquimod, bropirimine, UC-1V138, UC-1V136, UC-1V150, UC-1X105, UC-1V199, UC-1W236, UC-1X51, UC-1W247, UC-1X113, UC-1V199/L, UC-1V150/BSA, conjugates of UC-1V150 with or without a linker and MSA, OVA, virions, and/or ODN, conjugates of UC-1V199 and DOPE, silica, lipid, or irradiated spores, and conjugates of UC-1V1043 and UC-1V1018 with OVA all have shown activity.

Example III

Materials and Methods

Compound Evaluation In Vitro.

The ability of TLR7 conjugates to stimulate and/or to inhibit cytokine production is assessed in murine bone marrow derived mononuclear cells (BMDM) that are highly enriched in dendritic cells, as well as in human peripheral blood mononuclear cells (PBMC) cells. BMDM are plated in 96 well plates and treated in triplicate with vehicle or various doses starting from 10 µM diluted in 3-fold increments down to picomolar concentrations. After 24 hours the supernatants are harvested and assayed for up to 30 different cytokines, chemokines and other mediators, using a Luminex bead assay system, and commercially available reagents. The cytokine/chemokine ELISA results are supplemented with quantitative mRNA expression measurements and with two-dimensional phosphoprotein analyses, to gain insight into the scope and mechanism of tolerance induction. At the time of supernatant harvest, media are replaced in the wells with MTT, as a colorimetric assessment of cell survival. Human PBMC are isolated from commercial blood packs and treated similarly.

To assess the trafficking of the TLR agonist-conjugated nanoliposomes and dendrimers, the respective nanoparticles are loaded or modified with a fluorochrome. Subcellular localization is determined microscopically, in some cases in cells that have been treated with inhibitors of endosomal maturation.

To compare the anti-inflammatory activities of the TLR7 conjugates with different auxiliary groups, BMDM are treated first with the most potent compounds, at previously determined concentrations that had minimal effects on pro-inflammatory cytokine stimulation (TNFα, IL-1). After 24 hours, the medium is replaced, and the cells are challenged with activating ligands of different TLR family members (Pam3Cys for TLR2, poly(I:C) for TLR3, LPS for TLR4, flagellin for TLR5, Malp-2 for TRL6, UC-1V150 for TLR7, R848 for TLR7/8, CpG oligonucleotides for TLR9, and the like) at concentrations that effectively induce cytokine production in mock treated cells. The cells are assessed by multiplex immunoassay, quantitative PCR and phosphoprotein blotting. To better understand the kinetics of induction and maintenance of tolerance, TLR7 conjugate-primed cells are also challenged at different time intervals and analyzed for the pattern of cytokine production.

Compound Evaluation In Vivo.

Production of bronchoalveolar lavage fluid (BALF) versus systemic cytokines after administration to the airways of mice is assessed. Anesthetized female age-matched C57BL/6 mice are administered nasally (i.n.) orally (p.o.), or intravenously (i.v.), with various amounts of the TLR7 conjugates as previously described, or with the liposomes or dendrimers in appropriate vehicles. After recovery and at different time points, sera and BALF are collected and analyzed for cytokines and chemokines by Luminex assay. The weights, temperatures, and fluid intake patterns of the treated animals are recorded, as a clinical surrogate for a systemic "cytokine syndrome."

Subsequent experiments assess the ability of the different agents to produce local and systemic refractoriness (TLR tolerance) to TLR activation after high dose administration i.n., p.o. or i.v., as determined by sera and BALF cytokines High doses of the various TLR7 conjugates, which do not induce significant cytokines in vivo, nor clinical signs of a cytokine syndrome, are selected. Mice are treated with the selected high doses given by the different routes of administration, and then challenged with activators of different TLRs at various time points. Serum and BALF are collected and analyzed and clinical symptoms are recorded. The anti-inflammatory activities of the conjugates are confirmed with a lethal shock model previously used to study LPS and CpG. In this model, Balb/c mice that have been previously injected i.p. with D-galactosamine succumb after systemic challenge with different TLR activators, due to cytokine stimulation and liver damage. Active anti-inflammatory drugs fail to induce clinical symptoms in sensitized animals, and will also prevent shock caused by other TLR ligands. With a defined endpoint, this model is especially useful for determining the kinetics and duration of TLR tolerance.

Example IV

Materials and Methods

Mice.

Female C57BL/6 mice (5-6 weeks of age) were obtained from Harlan West Coast (Germantown, Calif.), and female A/J mice (6-8 weeks of age) were purchased from The Jackson Laboratories (Bar Harbor, Me.). A/J mice were used for infection with the Sterne strain of *B. anthracis* (Kenney et al., *J. Infect. Dis.*, 190:774 (2004)). The mice were bred and maintained under standard conditions in the University of California at San Diego Animal Facility, which is accredited by the American Association for Accreditation of Laboratory Animal Care. All animal protocols received prior approval by the Institutional Review Board. For the H1N1 influenza study, female BALB/c mice (16-18 g) were obtained from Charles River Laboratories (Wilmington, Mass.) and maintained in the American Association for Accreditation of Laboratory Animal Care-accredited Laboratory Animal Research Center of Utah State University.

In Vitro Stimulation of BMDM.

BMDM were isolated from various strains of mice were seeded in 96-well plates at a density of $5 \times 10^4$ cells per well. Compounds were added to 10-day-old cultures at a final concentration ranging from 0.01 to 10 µM or as otherwise indicated. After 24 hours of incubation, culture supernatants were collected and assayed for cytokine inductions by either sandwich ELISA (BD Pharmingen, San Diego, Calif.) or multiplex Luminex (Austin, Tex.) assay using the Beadlyte Mouse MultiCytokine customized kit (Upstate, Charlottesville, Va., and eBiosciences, San Diego, Calif.), according to the manufacturer's instructions.

Administration of Compounds to Mice.

Female age-matched C57BL/6 mice were injected with 100 µL of saline solution containing UC-1V150 or UC-1V150/MSA, each containing the equivalent of 0.38-38 nmol of the pharmacore via the tail vein. For intrapulmonary administration, mice were anesthetized with i.p. Avertin solution and shaved around the neck area. The trachea were exposed with a small incision and injected with 50 µL of saline solution containing various amounts of UC-1V150/MSA or the unconjugated drug. After recovery and at different time points, serum and BALF were collected and analyzed for IL-6, IL-12p40, IFN-γ, RANTES, and MCP-1 by Luminex assay. In other experiments, mice were anesthetized with an intramuscular ketamine/xylene solution and administered the same amount of UC-1V150/MSA in i.t. doses of 50 µl or i.n. doses of 20 µL. Because similar cytokine levels were observed in the BALF 24 hours after administration by either method, the more convenient i.n. route was used in infectious model studies.

Infection of A/J Mice with *B. anthracis* Spores.

Spores were prepared from the Sterne strain of *B. anthracis* (pXO1$^+$pXO2$^-$) as previously described (Sabet et al., *FEMS Immunol. Med. Microbiol.*, 47:369 (2006); Guidi-Rontani et al., *Mol. Microbiol.*, 42:931 (2001)). Purified spores were stored in PBS at $1 \times 10^8$ to $4 \times 10^8$ cfu/mL at 4° C. Before infection, the spores were heated to 65° C. for 30 minutes to initiate germination. A/J mice were anesthetized intramuscularly with ketamine/xylene solution and administered i.n. with 0.75 nmol of UC-1V150 or UC-1V150/MSA per mouse 1 day before anthrax infection. Control mice received saline only or saline containing MSA at equivalent amounts as in UC-1V150/MSA. Infection was carried out i.n. with $2 \times 10^5$ to $8 \times 10^5$ spores of *B. anthracis* in a 20 µL volume. Survival was observed for 13 days, because the majority of the saline-treated mice died within 3-6 days. Results were obtained from eight mice per group.

Infection of Balb/c Mice with Influenza Virus.

Influenza A/New Caledonia/20/99 (H1N1) virus was obtained from the Centers for Disease Control and Prevention (Atlanta, Ga.). The virus was propagated twice in Madin Darby canine kidney (MDCK) cells, further passaged 7 times in mice to make it virulent followed by another passage in cell culture to amplify it. Mice were anesthetized i.p. with ketamine (100 mg/kg) and infected i.n. with virus at approximately $10^{5.0}$ cell culture infectious doses per mouse in a 50 µL inoculum volume. A single intranasal dose of 75 µL in either saline alone or containing UC-1V150/MSA to 5 nmole per mouse was given 24 hours prior to virus exposure. Ten infected mice per treated group and 20 placebo control animals were followed for survival for 21 days.

Statistics.

Cytokine levels were compared by the Mann Whitney U-test with p≤0.05 to determine statistical significance. Kaplan-Meier survival curves and log rank tests were performed using GraphPad Prism software version 4.0c (San Diego, Calif.) to compare differences in survival.

Results

Potent In Vitro and In Vivo Cytokine Release in Response to UC-1V150/MSA Conjugates.

Figure 10B:
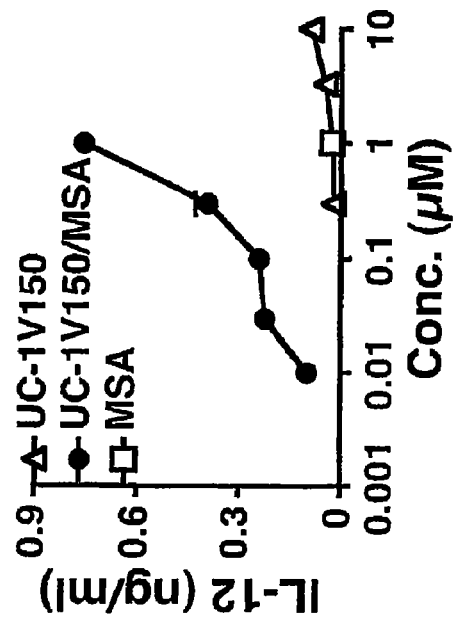
FIGS. 10A and B illustrate that the UC-1V150/MSA conjugates activate both murine bone marrow-derived macrophages (panel A) and human peripheral blood mononuclear cells (panel B). Cells were incubated with various concentrations of the conjugates from 0.5 nM to 10 μM with BMDM or from 0.1 to 10 μM with PBMC. Culture supernatants were harvested after 24 hours and cytokine levels were analyzed by Luminex.
Figure 10A:
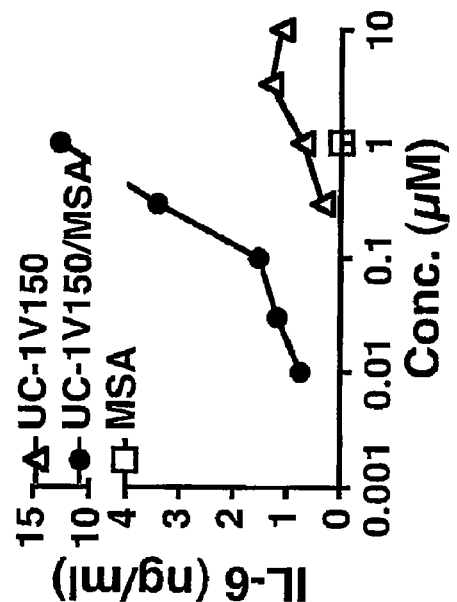
Figures 11A, 11B, 11C:
FIGS. 11A, B, and C illustrate the in vivo efficacy of a TLR7 agonist conjugate. C57BL/6 mice were injected (i.v. via the tail vein) with various amounts of UC-1V150 (aldehyde-modified SM-360320) or UC-1V150/MSA per mouse. Serum samples were collected and cytokine levels were analyzed by Luminex. The effect from the unconjugated synthetic TLR7 agonist, SM-360320, lasted for only 2 hours whereas UC-1V150/MSA extended the effect to at least 6 hours.

Incubation of bone-marrow-derived macrophages (BMDM) with UC-1V150 alone stimulated cytokine release (FIG. 10). When conjugated to MSA, similar or higher levels of cytokines were detected with a 10-fold lower equivalent concentration of the TLR7 agonist. Experiments with TLR transformants, performed as described previously, confirmed that UC-1V150, similar to the compound lacking the aldehyde modification (UC-1V136), was a specific TLR7 agonist (Lee et al., *Proc. Natl. Acad. Sci. USA*, 103:1828 (2006)). After i.v. injection into mice, UC-1V150 induced serum cytokine levels that peaked at about 2 hours after injection and then quickly declined to near background levels (data not shown). Comparison of the cytokine production profiles of UC-1V150 versus the UC-1V150/MSA 2 hours after i.v. injection at various dosages demonstrated that the MSA conjugate enhanced the potency by 10- to 100-fold (FIG. 11). Sera from saline or MSA control groups revealed little or no detectable cytokine levels (data not shown).

UC-1V150/MSA Conjugates Provide Prolonged and Localized Pulmonary Activity.

Figure 12:
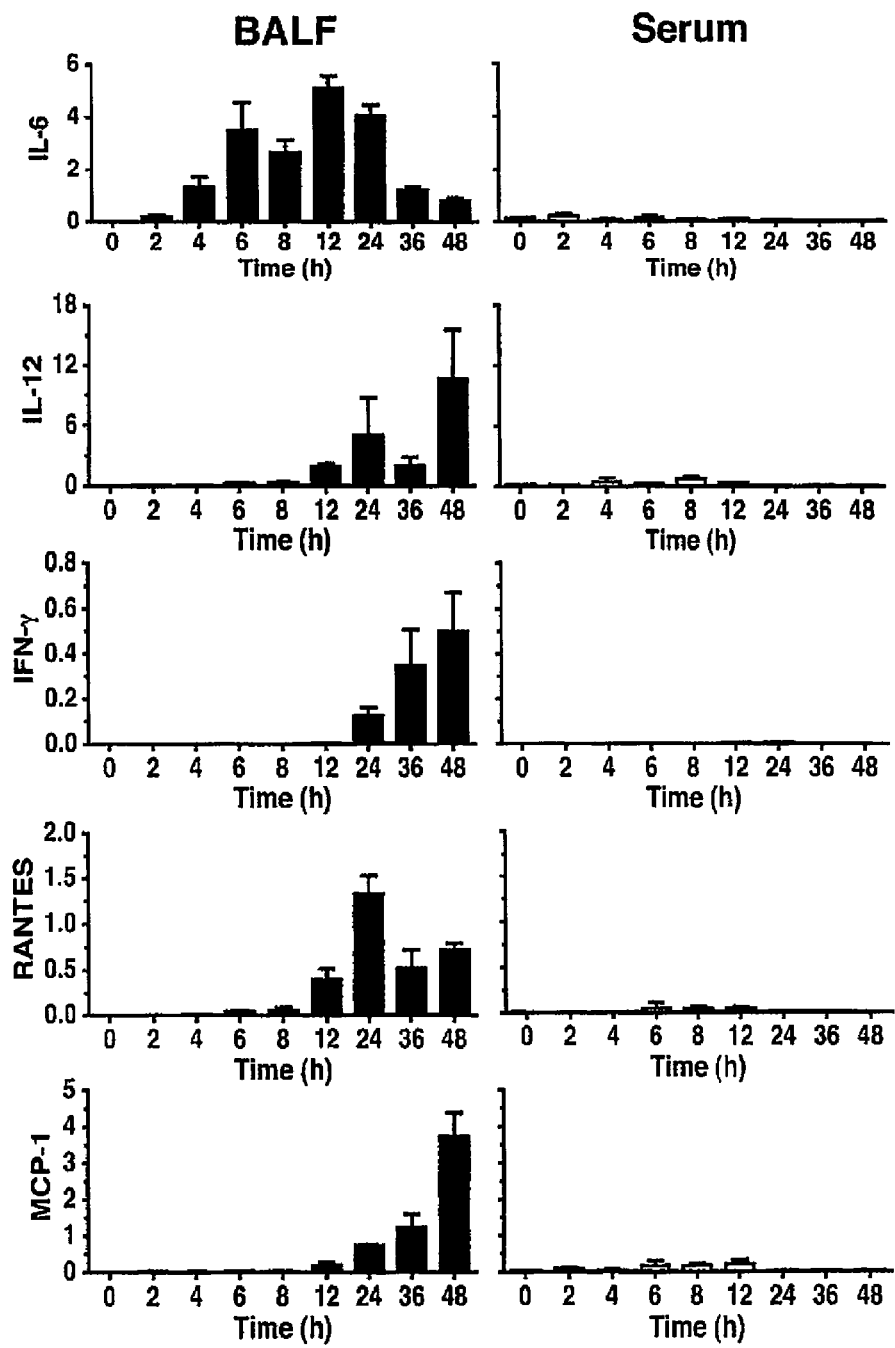
FIG. 12 shows sustained in vivo local activity of a UC-1V150/MSA conjugate without a systemic effect. C57BL/6 mice were anesthetized and administered (i.t.) with 3 nmol of UC-1V150/MSA. At the indicated time points, mice were sacrificed, and BALF and sera collected. The data were combined from two separate experiments with at least six mice per group. The results show the mean values±SEM.
Figure 14A:
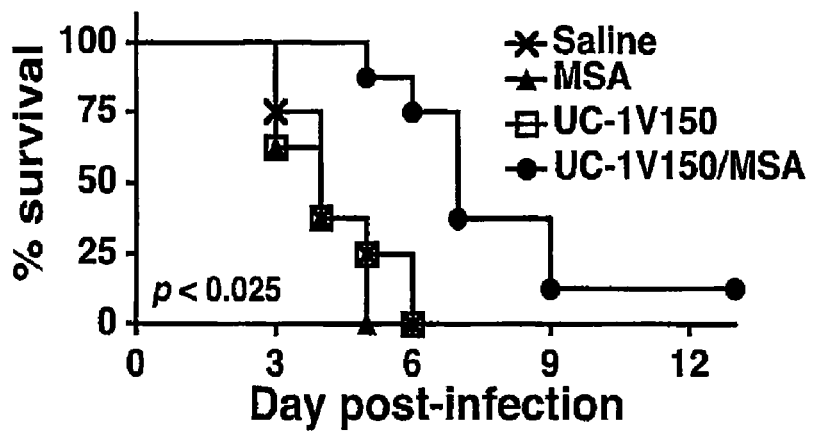
FIGS. 14A-B provide survival graphs after immunization of female A/J mice (panel A) or Balb/c mice (Panel B) with UC-1V150/MSA and challenge with spores. A) Age matched female A/J mice were administered i.n. saline only or saline containing MSA (an amount equivalent to UC-1V150/MSA), UC-1V150 or UC-1V150/MSA at 0.75 nmole/mouse 1 day before *B. anthracis* infection, and survival was assessed up to 13 days. B) Balb/c mice were administered i.n. saline or UC-1V150/MSA at 5 nmole/mouse 1 day before influenza virus infection, and survival followed for 21 days. In each model, Kaplan-Meier survival curves and log-rank tests were performed to determine significance. At least 8 mice were tested in each group.

To ensure adequate delivery of the TLR7 agonists to the respiratory system, the drugs were initially directly into the trachea. Substantial cytokine induction was found in bronchial alveolar lavage fluid (BALF) extracted from mice treated intratracheally (i.t.) with UC-1V150/MSA, whereas serum cytokines were very low and near background levels in the same animals (FIG. 12). In marked contrast, similar levels of cytokine were observed in both BALF and sera of mice injected i.t. with small-molecule TLR7 agonists, which sometimes induced behavioral changes, such as hair standing on end and shivering, suggestive of a cytokine syndrome (Table 2). Subsequent studies with UC-1V150 showed that intranasal (i.n.) delivery also induced selective cytokine production in the BALF, probably due to drug aspiration. Accordingly, i.n. administration was used to evaluate the UC-1V150 conjugates in two infectious animal models of pneumonitis. Mice pretreated i.n. with UC-1V150/MSA one day before infection with *B. anthracis* spores had an extended mean survival of 7.5 days compared with 5 days in control mice (P<0.025) (FIG. 14A). In contrast, no significant difference was observed in mice treated with either saline, the equivalent amount of MSA, or with UC-1V150 alone. These data confirmed that the UC-1V150 conjugate, but not the free drug, had intrapulmonary immunotherapeutic activity. Thus, conjugation of the TLR7 agonist to MSA enhanced its potency and reduced its toxicity after local delivery to the respiratory tract.

Figure 14B:
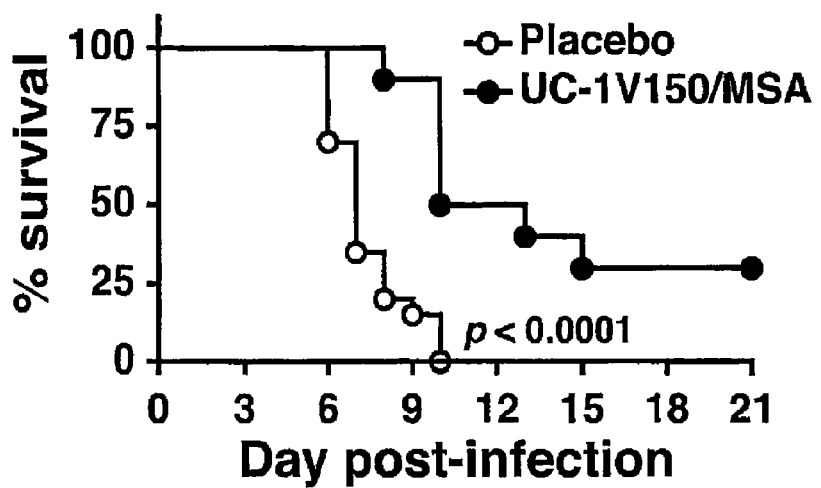
Figure 16:
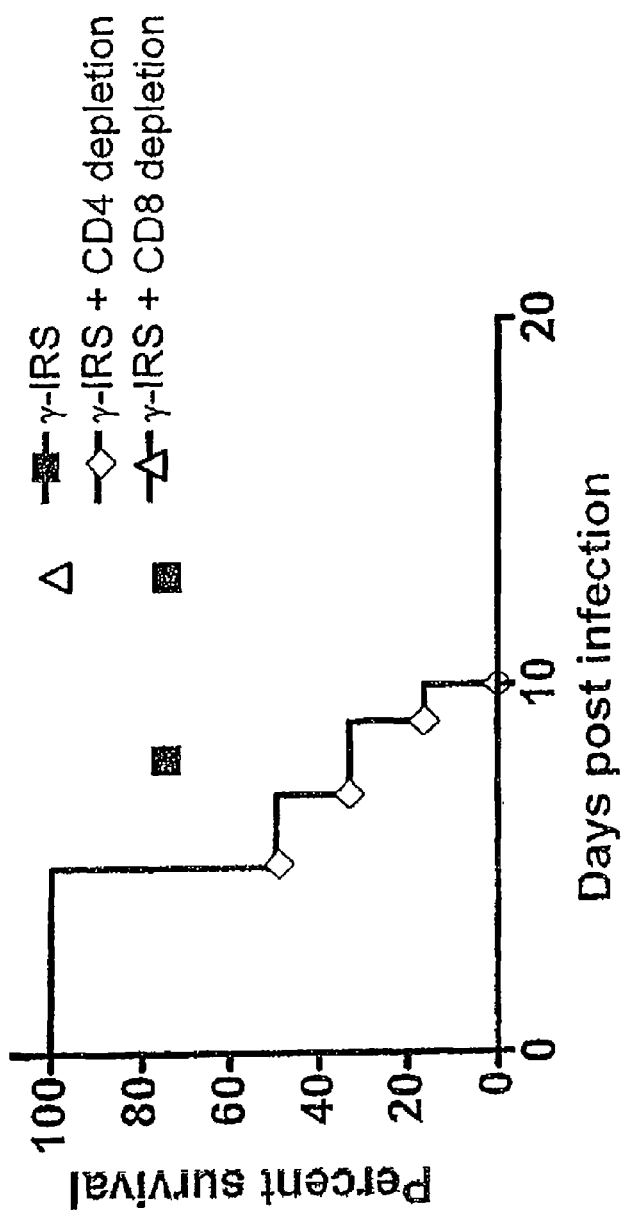
FIG. 16 illustrates that protection against anthrax spore exposure depends on CD4+ cells.
Figure 18:
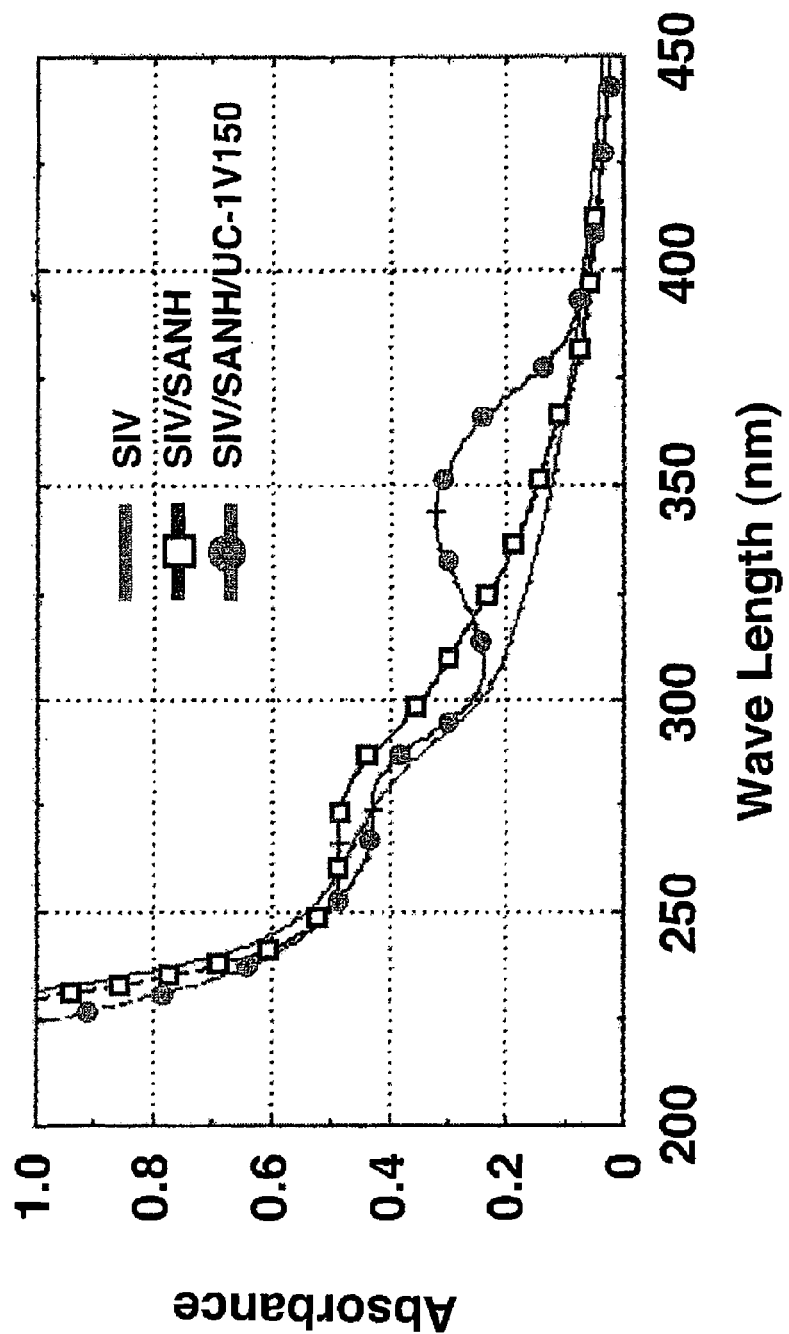
FIG. 18 illustrates the absorbance spectrum for direct conjugation of SIV particles to UC-1V150.
Figure 19:
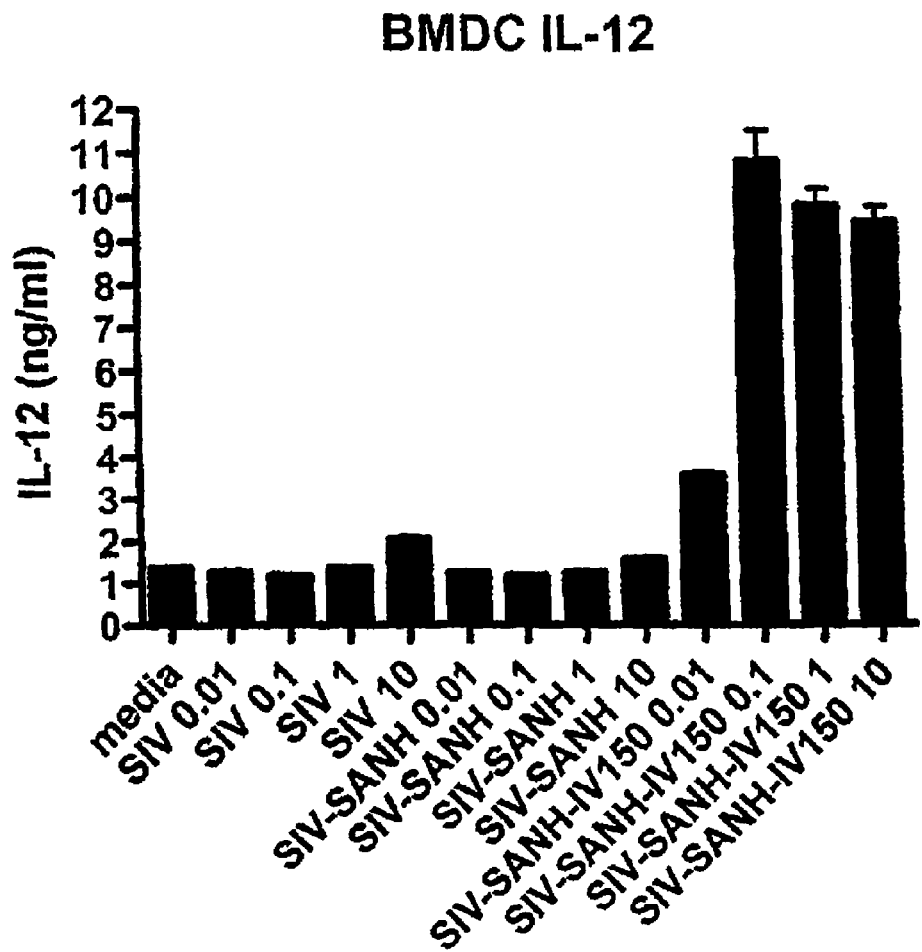
FIG. 19 illustrates the cytokine induction in BMDC by a conjugate of a synthetic TLR7 agonist and virus particles.
Figure 20A:
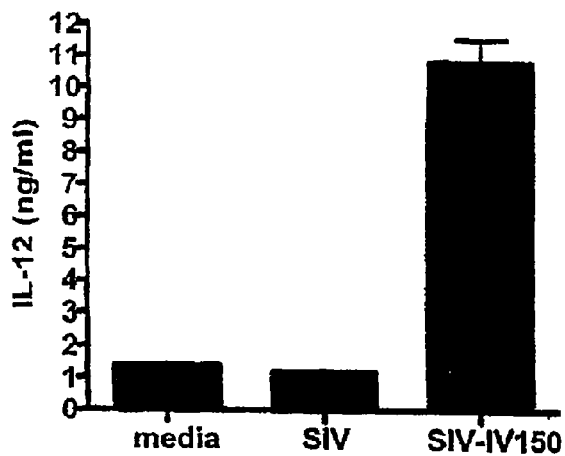
FIGS. 20A-B illustrate the effects of a UC-1V150/inactivated SIV conjugate (panel A) or UC-1V150/OVA/ODN (panel B) on IL-12 production. Myeloid BMDC were incubated for 24 hours under various conditions with 0.1 μg/mL as indicated. IL-12 levels in the cell supernatant were measured by ELISA.
Figure 20B:
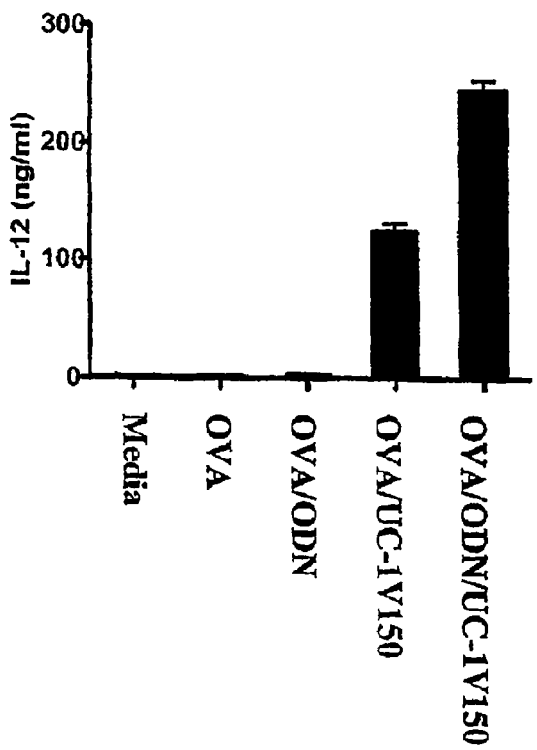
Figure 21:
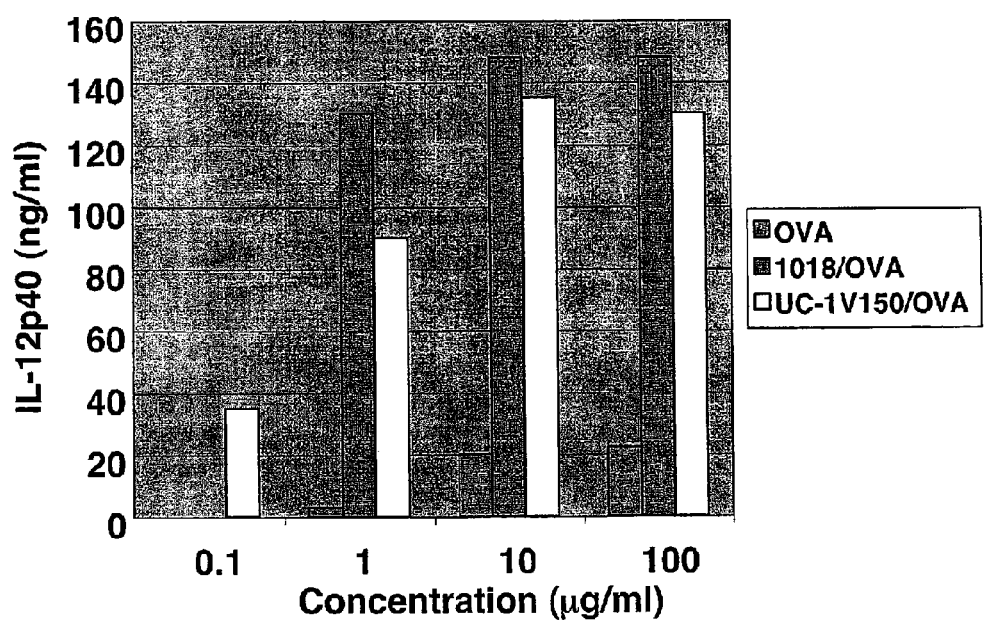
FIG. 21 is a graphic illustration of the stimulation of bone marrow derived dendritic cells (BMDC) with OVA/UC-1V150 or OVA/ODN (ODN=oligodeoxynucleotide).
Figure 22:
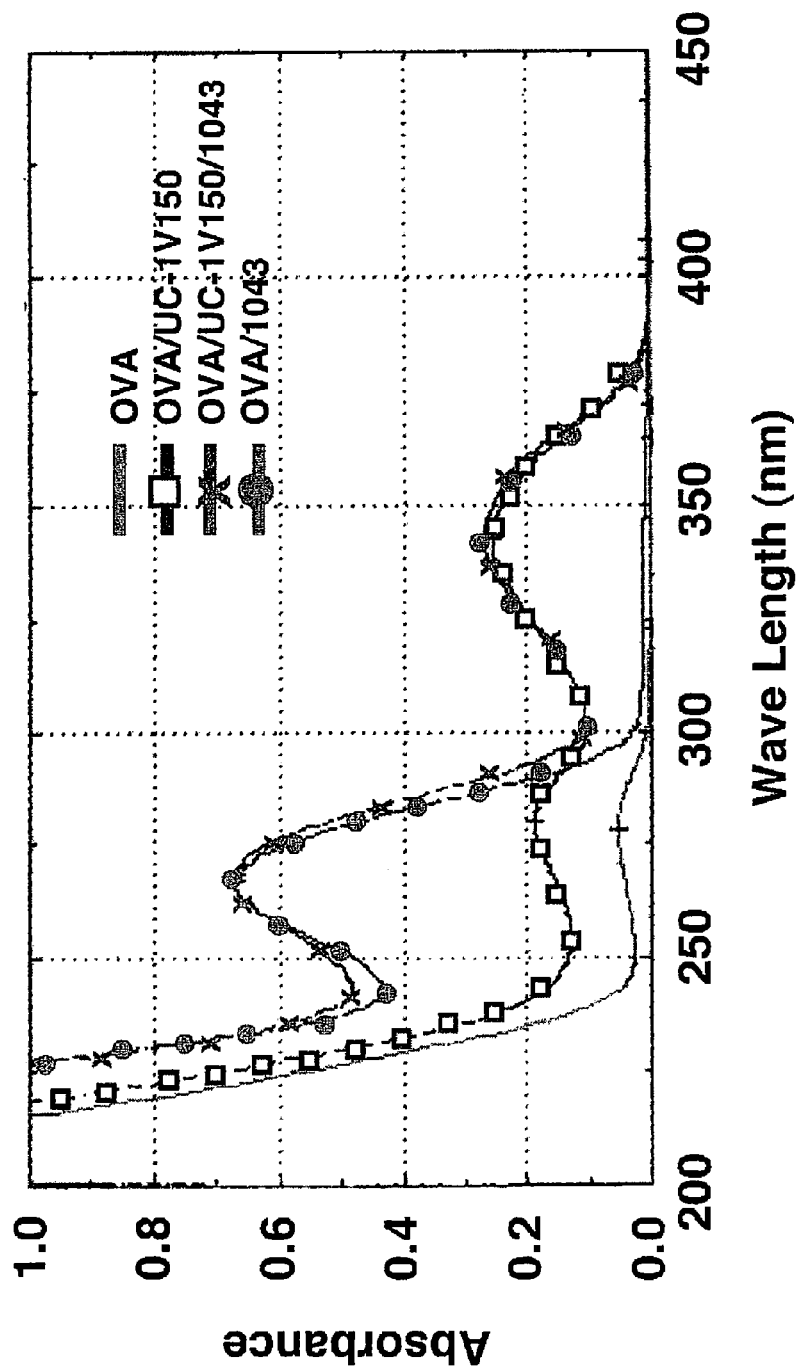
FIG. 22 is an illustration of the UV spectrum of a double-conjugate, (OVA/UC-1V150/ODN 1043).
Figure 23:
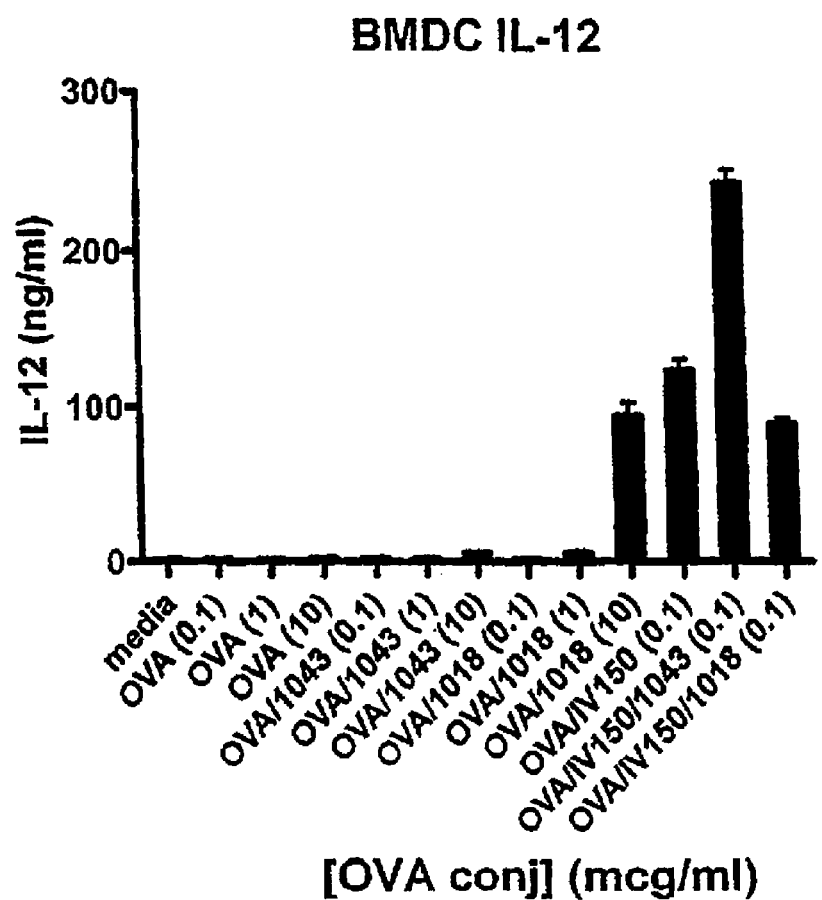
FIG. 23 is an illustration of the induction of IL-12 in BMDC using OVA/ODN/UC-1V150 conjugates. OVA/1043 and OVA/1018 are ODN conjugates.
Figure 24:
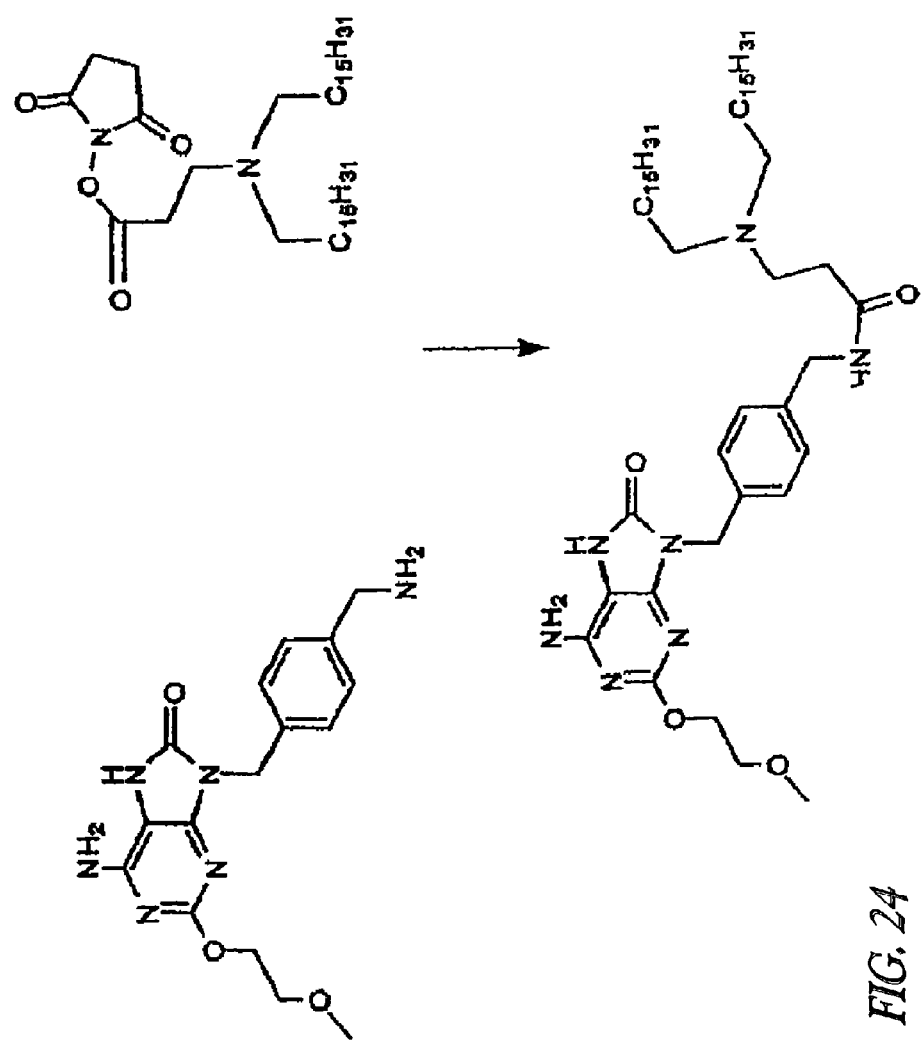
FIG. 24 illustrates conjugation of a synthetic TLR agonist to a lipid component of a liposome. Self-assembly of the TLR conjugate coupled via spacer-linker to a C-15 lipid, resulted in the formation of 100 nM nanoparticles. TLR agonist and an NHS-ester of the lipid were reacted in equimolar amounts in DMF and 1 equivalent of triethylamine for 6 hours. The reaction mixture was purified by preparing HPLC under isocratic conditions in 50:50 acetonitrile/water.
Figure 25:
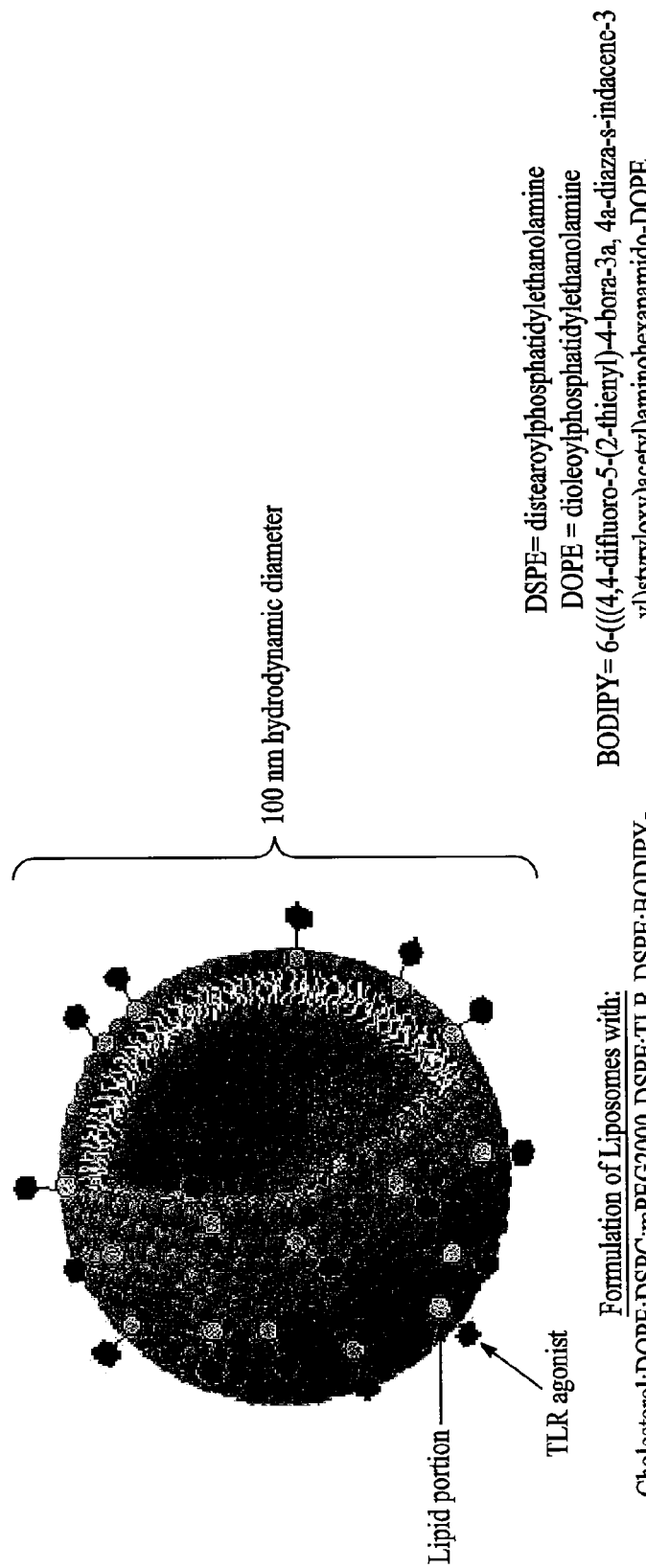
FIG. 25 shows a schematic of a TLR agonist/liposome conjugate. Liposomes are formed with cholesterol:DOPE:DSPC:mPEG2000-DSPE:TLR-DSPE:BODIPY-DOPE 30:30:30:5:5:1.5;
DSPE=distearoylphosphatidylethanolamine;
DOPE=dioleoylphosphatidylethanolamine; BODIPY=6-(((4-4-difluoro-5-(2-thienyl)-4-bora-3a,4a-diaza-s-indacene-3-yl)styryloxy)acetyl)aminohexanamido-DOPE.
Cholesterol:DOPE:DSPC:DSPE-TLRagonist:DSPE-mPEG (in 1:1:1:0.16:0.16 molar ratio) in chloroform were taken in 30 mL glass culture tubes, dried under a stream of nitrogen gas and vacuum-dessicated for a minimum of 6 h to remove any residual organic solvent. The dried lipid film was hydrated in sterile deionized water in a total volume of 1 mL for a minimum of 12 hours. Liposomes were vortexed for 2-3 minutes to remove any adhering lipid film and sonicated in a bath sonicator (ULTRAsonik 28X) for 2-3 minutes at room temperature to produce multilamellar vesicles (MLV). MLVs were then sonicated with a Ti-probe (using a Branson 450 sonifier at 100% duty cycle and 25 W output power) in an ice bath for 1-2 minutes to produce small unilamellar vesicles (SUVs) as indicated by the formation of a clear translucent solution. The solution was pressure filtered in sequence though 200 and then 100 nm nucleopore polycarbonate membranes to obtain liposome nanoparticles of 100 nm with a polydispersity factor of less than 0.1.
Figure 26:
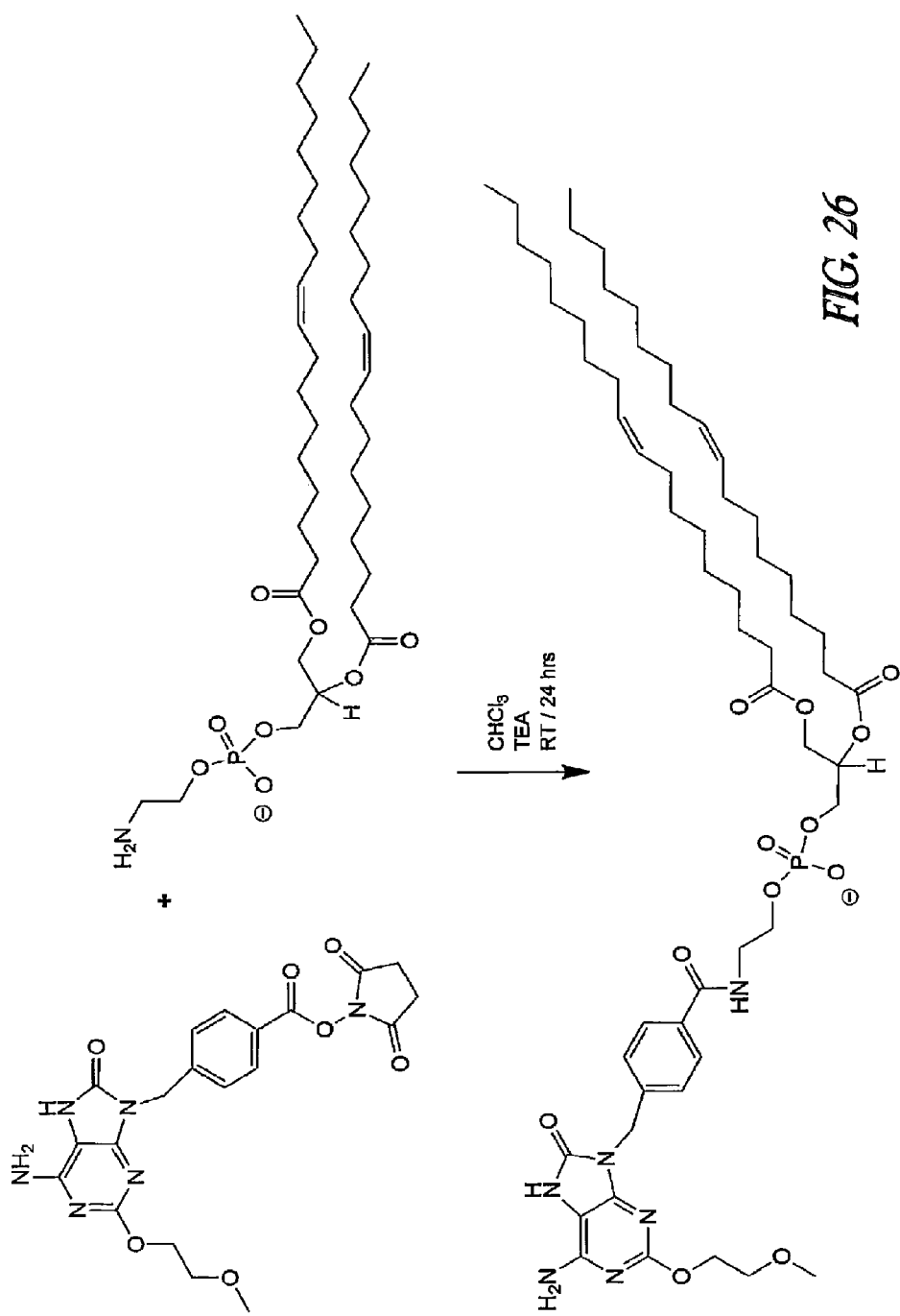
FIG. 26 shows synthesis of lipid conjugate WW-109. 0.45 mg (1 µmole) of IV-199 was added to 100 µL of a 10 mM solution of DOPE in chloroform. To this solution was added 0.1 mg of triethylamine from a chloroform stock. The mixture was reacted at room temperature for 24 hours and the chloroform was rotavaped. The white solid residue was washed three times in 60%/methanol/hexane and centrifuged to obtain a white solid. The m/z by Mass spec was 1086 and the compound had a uv max absorption at 268 nm. Fatty acid moieties of various chain lengths can be used to prepare the analogous compounds, including $C_{14}$-$C_{22}$ carboxylic acids with one, two, three, or four sites of unsaturation, epoxidation, hydroxylation, or a combination thereof, at any feasible locations of the carboxylic acid carbon chain. In one specific embodiment, the fatty acid moieties are $C_{17}$ carboxylic acids with a site of unsaturation at $C_8$-$C_9$. In another specific embodiment, the fatty acid moieties are $C_{18}$ carboxylic acids with a site of unsaturation at $C_9$-$C_{10}$. The carboxylic acid moieties of each fatty acid moiety can be the same, or they can be different (see, e.g., FIG. 6).
Figure 27:
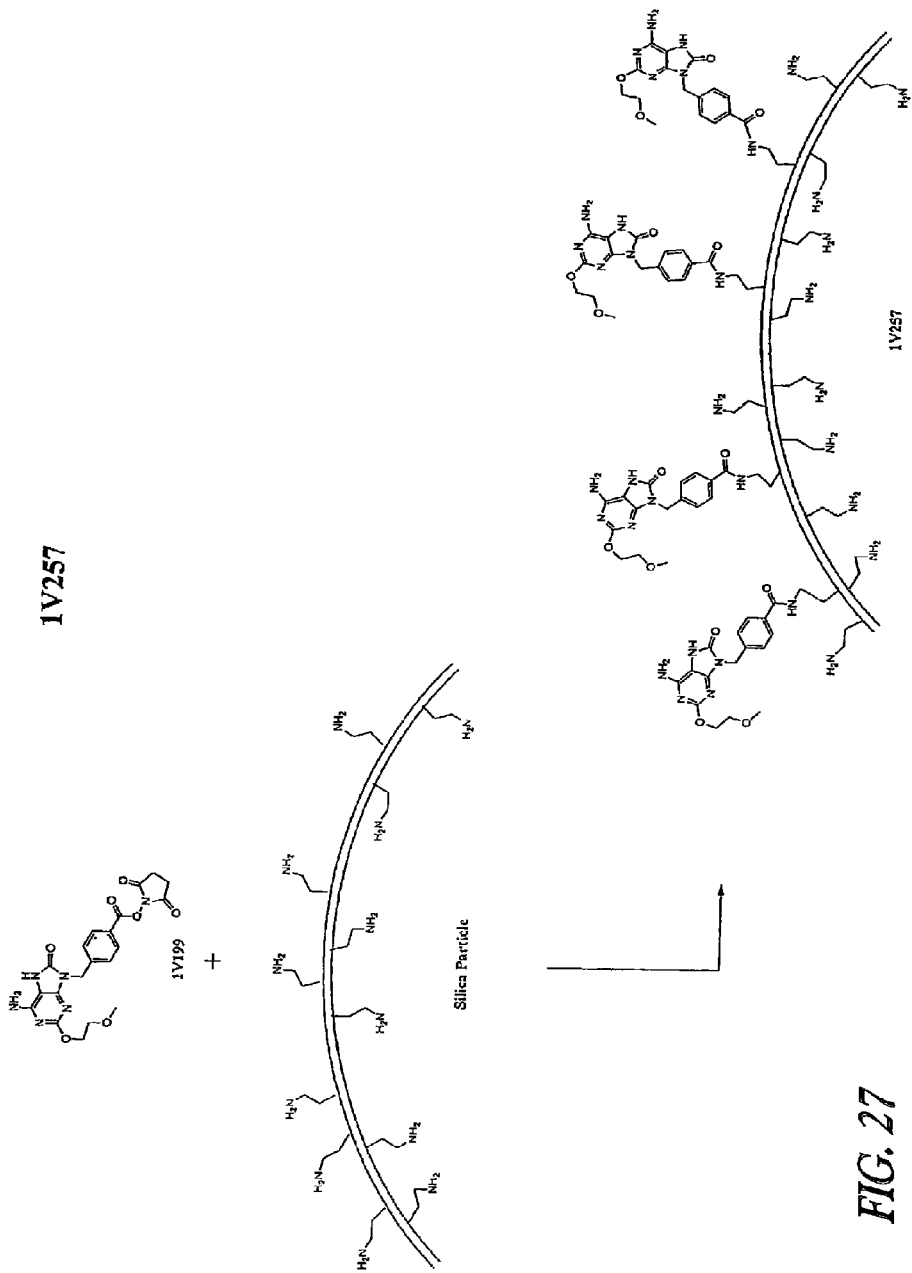
FIG. 27 illustrates a schematic of a silica particle with TLR agonists covalently bonded thereto.
Figure 28A:
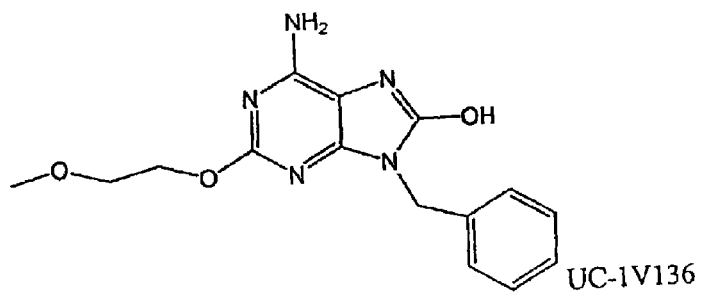
Figure 28A:
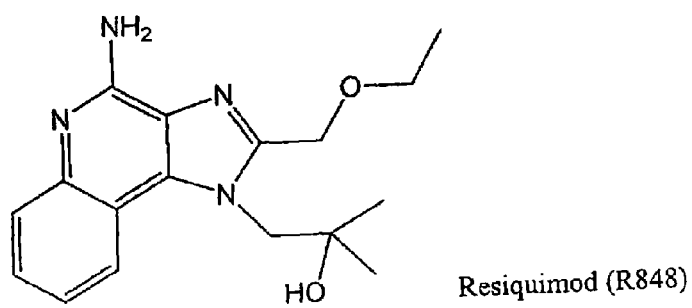
Figure 28A:
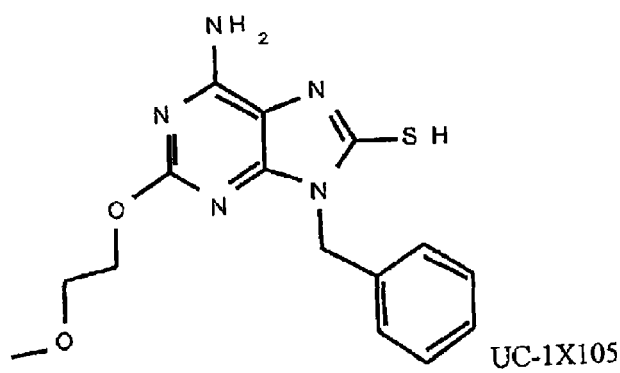
Figure 28A:
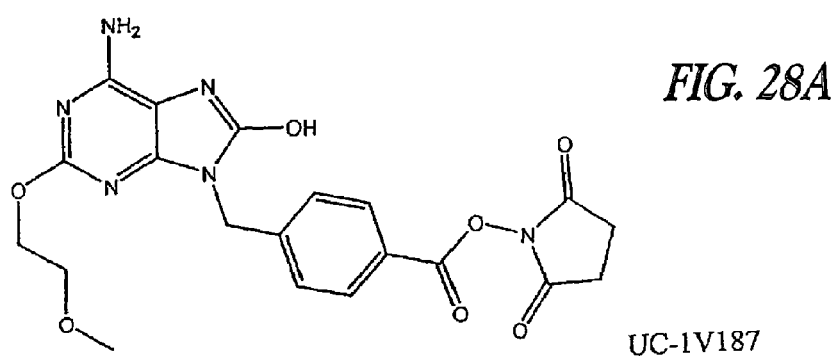
Figure 28C:
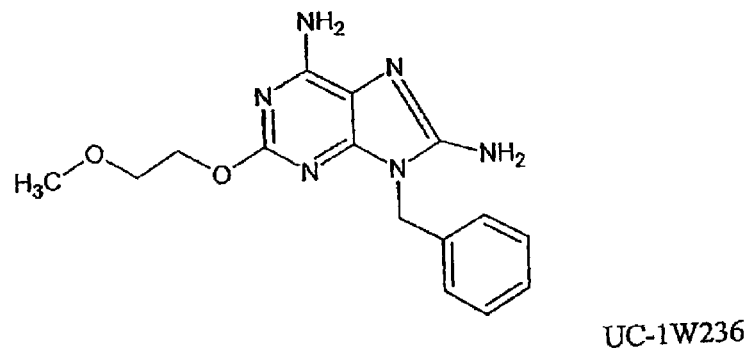
Figure 28C:
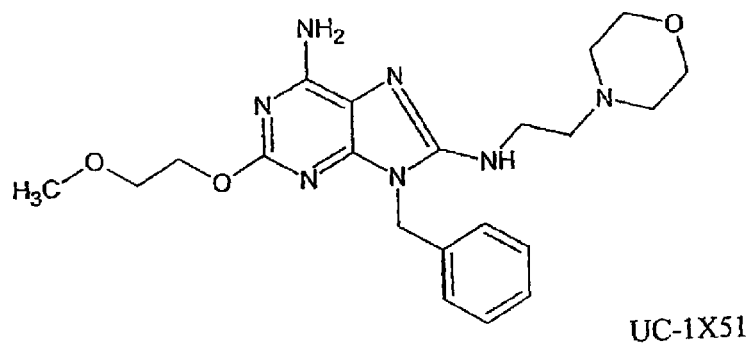
Figure 28C:
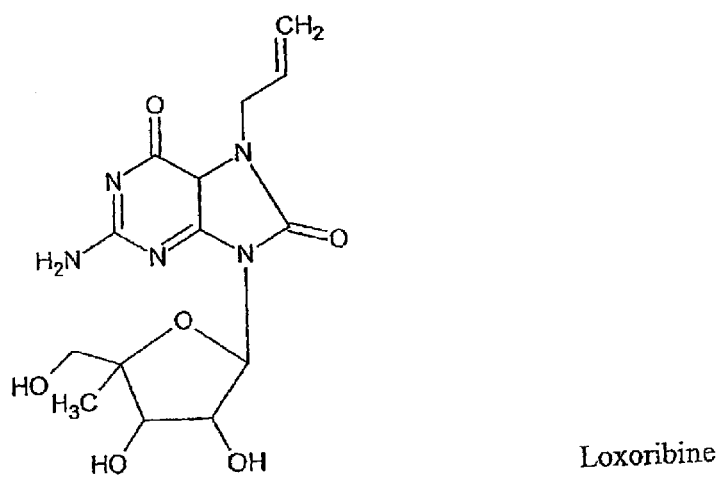
Figure 28D:
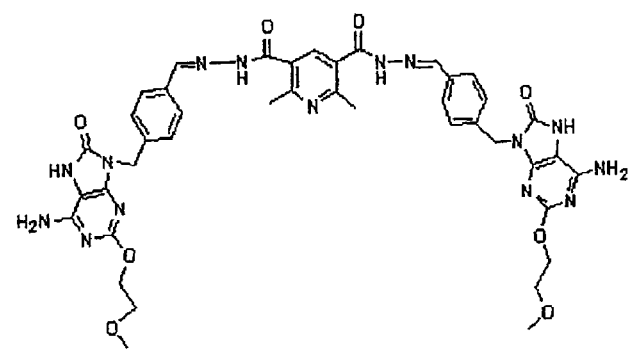
Figure 28D:
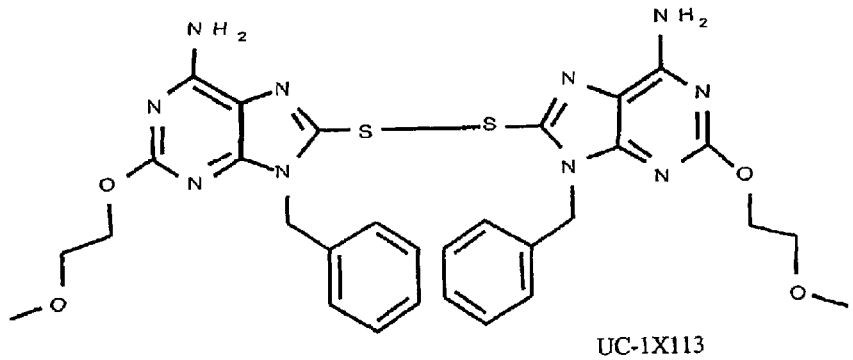
Figure 28D:
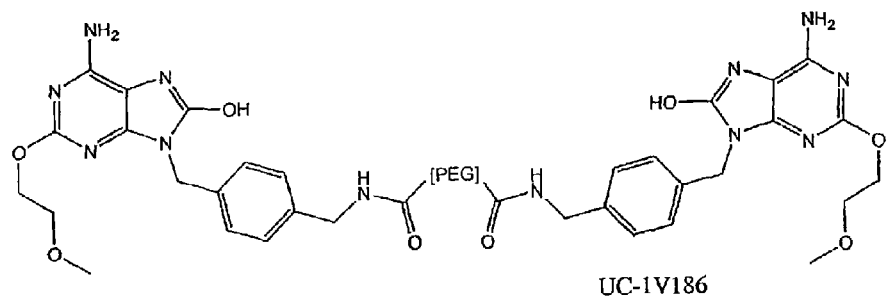

In another study, BALB/c mice were pretreated i.n. with the UC-1V150/MSA conjugate 1 day before influenza virus infection (H1N1 strain). The mean survival of the treated mice was extended to 11.5 days compared with 7 days in untreated controls (P<0.0001) (FIG. 14B). Together these results suggest that conjugation of the TLR7 agonist to MSA enhanced its potency and reduced its toxicity after local delivery to the respiratory tract.

UC-1V150/MSA was administered i.n. prior to anthrax infection followed by treatment with ciprofloxacin (25 mg/kg) on day 4. Placebo treatment followed by ciprofloxacin treatment resulted in about 15-25% survival, while treatment with a conjugate and ciprofloxacin resulted in about 90% survival. Thus, the conjugate is particularly useful as a coadjuvant with an anthrax vaccine.

Discussion

The compound UC-1V150 is one of the most potent and versatile synthetic small-molecule TLR7 ligands yet discovered because (i) it is active at nanomolar concentrations; (ii) it can be coupled to a variety of macromolecules with enhancement of activity in some cases; and (iii) its pharmacokinetic properties can be changed by modification of the auxiliary groups. The TLR7-protein conjugate UC-1V150/MSA was characterized as having approximately five small molecules covalently linked to each MSA protein molecule. The conjugate retained TLR7 agonist activity and indeed was both more potent and had a longer duration of action, compared with the free monomeric drug. Moreover, this conjugate could be delivered effectively to the respiratory system by i.n. or i.t. administration. Drug delivery by i.n. proved to be effective in a mouse model of a bacterial infection. When considering delivery to the respiratory system, a potentially important advantage of preparing the TLR7 agonists as conjugates of macromolecules is that systemic side effects may be avoided by confining the immunostimulatory activity to the local mucosal environment.

The macromolecular conjugate would be expected to be absorbed into the systemic circulation more slowly than the free drug and, indeed, may be avidly scavenged by resident macrophages and dendritic cells expressing TLR7. Accordingly, the conjugate should mitigate the type of severe side effects that have been associated with systemic delivery of TLR7/8 agonists. The UC-1V150/MSA conjugate may also provide beneficial immunotherapeutic activity when administered to mucosal sites, such as the genitourinary and gastrointestinal tracts, for the control of infectious, allergic, or malignant diseases. The macromolecular carrier of the TLR7 agonist may also provide an improved approach for selective delivery of the immunotherapeutic to a specific organ or tissue. For example, the lipid conjugates of UC-1V150 can be incorporated into liposomes of different size and composition, whereas protein conjugates of the TLR7 agonist may target different dendritic cell subsets. Differences in the intracellular trafficking of the UC-1V150 conjugate may induce distinct patterns of cytokine production, analogous to the effects observed with TLR9-activating oligonucleotides (Rothenfusser et al., *Hum. Immunol.*, 63:111 (2002)).

One potential problem that has been observed with drugs conjugated to proteins is the development of antibodies against the low-molecular-weight hapten-like portion of the molecule. However, UC-1V150, unlike the TLR7/8 vaccine conjugates studied earlier, has a simple adenine-like structure that is unlikely to induce hypersensitivity reactions. Indeed, anti-UC-1V150 antibodies were not observed after administration of the protein conjugates, except after repeated administration of a keyhole limpet hemocyanin carrier in complete Freud's adjuvant (unpublished data).

New agents for the prevention and treatment of influenza virus infections are being sought, particularly with the spread of highly pathogenic strains from Asia. Morbidity and mortality from commonly circulating strains is high each year. Treatment of the infection can be accomplished by approved antiviral drugs, which are moderately effective if started early. Enhancement of the immune system is also being investigated as a strategy that could accelerate protective antiviral responses, especially in immune compromised hosts. It is possible that systemic immune activation via TLR signaling does not create a local cytokine and chemokine gradient required to mobilize immune cells to the site of infection. In support of this hypothesis, the unconjugated UC-1V150, which is rapidly absorbed through the mucosa, failed to protect mice from *B. anthracis* infection, whereas the UC-1V150 conjugate was effective.

*B. anthracis* has become an agent of bioterrorism. A rapid response against microbial pathogens is critical for effective biodefense. In general an antibody or cellular immune response may protect against these pathogens; however, generating these protective responses quickly requires prior exposure to specific antigens for each organism. Although it is known that influenza virus engages TLR7 (Barchet et al., *Eur. J. Immunol.*, 35:360 (2005)), bacterial anthrax most likely can engage TLR2, TLR4, and TLR9. In addition to being a common signaling intermediary for the TLRs, MyD88 has also been shown to be necessary for resistance to infection in a mouse model of anthrax (Hughes et al., *Infect. Immun.*, 73:7535 (2005)). Because the UC-1V150 conjugate works effectively as an adjuvant against infections that use different pathways, it can be applied as a biodefense strategy that would not need be specific to the antigens of a particular microbe and that would be useful in mixed as well as single agent attacks.

Example V

There is no known SA vaccine that is potent enough or that can act quickly enough to prevent SA infections in "at-risk" patients prior to hospitalization. A single injection of a potent TLR7 agonist and killed gram-positive bacteria, e.g., SA, or a subunit thereof, may boost protective immunity to the bacteria within one week of administration. The injection may include, for example, 1) a TLR7 agonist such UC-IV199 conjugated directly to free amino groups on killed gram-positive bacteria, 2) a TLR7 agonist such as UC-IV199 conjugated to albumin in combination with killed gram-positive bacteria, 3) a TLR7 agonist such as UC-IV199 conjugated to a recombinant gram-positive bacterial protein, or 4) a TLR7 agonist such as UC-IV199 conjugated to gram-positive bacterial polysaccharides (e.g., via a linker known to the art, such as that used the StaphVax®).

As described hereinabove, a TLR7 agonist was conjugated to lethally irradiated spores of the Sterne vaccine strain of *Bacillus anthracis* (BA). Like SA, BA is a gram-positive bacteria. Compared to spores alone, the conjugated bacterium was a potent activator of mouse bone marrow derived macrophages (BMDM) as measured by cytokine (IL-12 and IL-6) secretion. In another experiment, a single injection into mice of lethally irradiated spores of the Sterne strain of BA, mixed with a TLR7 agonist conjugated to mouse albumin (MSA), protected the animals against lethal intra-pulmonary BA challenge given only six days later. In contrast, injection of the animals with BA spores alone, or with BA plus a conventional adjuvant, cholera toxin (CT), did not protect the animals. Thus, a TLR7-agonist albumin/irradiated spore vaccine induced protective immunity to *Bacillus anthracis* within 6 days. This rapidity of response in a naïve animal was totally unexpected. The same vaccine technology will likely protect humans from hospital-acquired SA infection.

All publications, patents, and patent documents cited in the specification are incorporated by reference herein, as though individually incorporated by reference. In the case of any inconsistencies, the present disclosure, including any definitions therein will prevail. The invention has been described with reference to various specific and preferred embodiments and techniques. However, it should be understood that many variations and modifications may be made while remaining within the spirit and scope of the invention.

What is claimed is:

1. A composition comprising a compound of formula A:

[Chemical structure of formula A showing a purine-like ring system with NH$_2$, R$^1$—X$^1$ substituent, OH group, and benzyl group with X$^2$—R$^3$ substituent]

or a pharmaceutically acceptable salt thereof, wherein
X$^1$ is —O—;
R$^1$ is hydrogen, (C$_1$-C$_{10}$)alkyl, or, (C$_1$-C$_{10}$)alkyl substituted with (C$_1$-C$_6$)alkoxy;
X$^2$ is C(O); and
R$^3$ is a phosphatidyl ethanolamine comprising two C$_{14}$-C$_{22}$ carboxylic acid groups each having one, two, three, or four sites of unsaturation, epoxidation, hydroxylation, or a combination thereof, each at a location of the respective carboxylic acid group carbon chain.

2. The composition of claim 1 wherein X$^2$-R$^3$ is bonded to a carbon atom para to the methylene carbon bonded to the heteroaryl nitrogen atom.

3. The composition of claim 1, wherein the two carboxylic acid groups of the phosphatidyl ethanolamine of the compound of Formula A are the same.

4. The composition of claim 1, wherein either or both carboxylic acid groups of the phosphatidyl ethanolamine of the compound of Formula A is a $C_{17}$ carboxylic acid group with a site of unsaturation at C8-C9.

5. The composition of claim 1, wherein either or both carboxylic acid groups of the phosphatidyl ethanolamine of the compound of Formula A is a $C_{18}$ carboxylic acid group with a site of unsaturation at C9-C10.

6. The composition of claim 1, wherein $R^1$ of the compound of Formula A is a $(C_1-C_{10})$alkyl substituted with $(C_1-C_6)$alkoxy.

7. The composition of claim 1, wherein for the compound of Formula A, $R^1$ is —$(CH_2)_2$—$OCH_3$.

8. The composition of claim 1, which further comprises a liposome.

9. A composition comprising an amount of a compound of Formula A of claim 1 effective as an adjuvant.

10. A vaccine comprising an antigen and a compound of Formula A of claim 1.

11. The composition of claim 1, wherein the two carboxylic acid groups of phosphatidyl ethanolamine of the compound of Formula A are different.

* * * * *